United States Patent
Griffith et al.

(10) Patent No.: US 10,876,088 B2
(45) Date of Patent: Dec. 29, 2020

(54) MODULAR ORGAN MICROPHYSIOLOGICAL SYSTEM WITH INTEGRATED PUMPING, LEVELING, AND SENSING

(71) Applicant: Massachusetts Institute of Technology, Cambridge, MA (US)

(72) Inventors: Linda Griffith, Cambridge, MA (US); David Trumper, Plaistow, NH (US); Collin Edington, Cambridge, MA (US); Gaurav Rohatgi, Boston, MA (US); Duncan Freake, Boston, MA (US); Luis Soenksen, Boston, MA (US); Mohan Brij Bhushan, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 370 days.

(21) Appl. No.: 15/425,858

(22) Filed: Feb. 6, 2017

(65) Prior Publication Data

US 2017/0227525 A1    Aug. 10, 2017

Related U.S. Application Data

(60) Provisional application No. 62/291,102, filed on Feb. 4, 2016, provisional application No. 62/359,567, filed on Jul. 7, 2016.

(51) Int. Cl.
*C12M 1/32* (2006.01)
*C12M 1/12* (2006.01)
(Continued)

(52) U.S. Cl.
CPC ......... *C12M 23/12* (2013.01); *B01L 3/50273* (2013.01); *B01L 3/502715* (2013.01);
(Continued)

(58) Field of Classification Search
CPC ...... C12M 23/12; C12M 29/10; C12M 24/14; F04B 43/043; F04B 43/12; F04B 19/006;
(Continued)

(56) References Cited

U.S. PATENT DOCUMENTS

| | | | | |
|---|---|---|---|---|
| 6,103,199 A | * | 8/2000 | Bjornson | B01J 19/0046 204/450 |
| 6,197,575 B1 | | 3/2001 | Griffith | |

(Continued)

FOREIGN PATENT DOCUMENTS

| | | | | |
|---|---|---|---|---|
| GB | 2147100 A | * | 5/1985 | ............ B01L 3/0203 |
| WO | 2005123950 | | 12/2005 | |
| WO | 2011071772 | | 6/2011 | |

OTHER PUBLICATIONS

Anna, "Droplets and Bubbles in Microfluidic Devices", Annu. Rev. Fluid Mech. 48:285-309 (2016).
(Continued)

*Primary Examiner* — Michael L Hobbs
(74) *Attorney, Agent, or Firm* — Pabst Patent Group LLP

(57) ABSTRACT

Fluidic multiwell bioreactors are provided as a microphysiological platform for in vitro investigation of multi-organ crosstalks for an extended period of time of at least weeks and months. The disclosed platform is featured with one or more improvements over existing bioreactors, including on-board pumping for pneumatically driven fluid flow, a redesigned spillway for self-leveling from source to sink, a non-contact built-in fluid level sensing device, precise control on fluid flow profile and partitioning, and facile reconfigurations such as daisy chaining and multilayer stacking. The platform supports the culture of multiple organs in a microphysiological, interacted systems, suitable for a wide range of biomedical applications including systemic toxicity studies and physiology-based pharmacokinetic and pharma- (Continued)

codynamic predictions. A process to fabricate the disclosed bioreactors is also provided.

36 Claims, 18 Drawing Sheets

(51) Int. Cl.
F04B 23/04 (2006.01)
F04B 43/12 (2006.01)
B01L 3/00 (2006.01)
C12M 1/00 (2006.01)
F04B 43/04 (2006.01)
F04B 23/06 (2006.01)
F04B 19/00 (2006.01)

(52) U.S. Cl.
CPC ....... *B01L 3/502738* (2013.01); *C12M 25/14* (2013.01); *C12M 29/10* (2013.01); *F04B 19/006* (2013.01); *F04B 23/04* (2013.01); *F04B 23/06* (2013.01); *F04B 43/043* (2013.01); *F04B 43/12* (2013.01); *B01L 2200/0621* (2013.01); *B01L 2300/0829* (2013.01); *B01L 2300/0887* (2013.01); *B01L 2400/0406* (2013.01); *B01L 2400/0457* (2013.01); *B01L 2400/0487* (2013.01); *B01L 2400/0655* (2013.01); *B01L 2400/086* (2013.01)

(58) Field of Classification Search
CPC .... F04B 23/06; F04B 23/04; B01L 3/502715; B01L 3/502738; B01L 3/50273; B01L 2400/0406; B01L 2400/086; B01L 2400/0457; B01L 2400/0487; B01L 2400/0655; B01L 2300/0829; B01L 2300/0887; B01L 2200/0621
See application file for complete search history.

(56) References Cited

U.S. PATENT DOCUMENTS

| | | | |
|---|---|---|---|
| 8,318,479 B2 | 11/2012 | Domansky | |
| 9,249,387 B2 | 2/2016 | Cuiffi | |
| 9,528,082 B2 | 12/2016 | Cuiffi | |
| 9,632,076 B2 | 4/2017 | Achyuta | |
| 2001/0036672 A1 | 11/2001 | Anderson | |
| 2004/0228770 A1* | 11/2004 | Gandhi | B01L 3/5085 422/504 |
| 2005/0244932 A1 | 11/2005 | Harding | |
| 2005/0260745 A1 | 11/2005 | Domansky | |
| 2008/0166786 A1 | 7/2008 | Nishiyama | |
| 2010/0230613 A1 | 9/2010 | Pieprzyk | |
| 2013/0020386 A1 | 1/2013 | Yoshida | |
| 2014/0196560 A1 | 7/2014 | Lai | |
| 2015/0140581 A1 | 5/2015 | Achyuta | |
| 2015/0167863 A1 | 6/2015 | Mescher | |
| 2015/0301027 A1 | 10/2015 | Charest | |
| 2016/0003229 A1 | 1/2016 | Mescher | |
| 2016/0040112 A1 | 2/2016 | Coppeta | |
| 2016/0047832 A1 | 2/2016 | Gumbrecht | |
| 2016/0129440 A1 | 5/2016 | Borenstein | |
| 2016/0145553 A1 | 5/2016 | Cuiffi | |
| 2016/0151778 A1* | 6/2016 | McClelland | B01L 3/502 435/309.1 |
| 2016/0220961 A1 | 8/2016 | DiBiasio | |
| 2016/0220997 A1 | 8/2016 | Mescher | |
| 2016/0244727 A1 | 8/2016 | Borenstein | |

OTHER PUBLICATIONS

Berthier, et al., "Metastable capillary filaments in rectangular cross-section open microchannels", AIMS Biophysics, 1(1):31-48 (2014).
Brakke, et al., "The surface evolver", Exp Math, 1(2):141-65 (1992).
Brown, et al, "Physiological parameter values for physiologically based pharmacokinetic models", Toxicol Ind Health, 13(4):407-84 (1997).
Chitcholtan, et al., "Differences in growth properties of endometrial cancer in three dimensional (3D) culture and 2D cell monolayer", Exp Cell Research, 319(1):75-87 (2013).
Clark, et al., "A liver microphysiological system of tumor cell dormancy and inflammatory responsiveness", Lab Chip, 17(1):156-68 (2016).
Cook, et al., "Lessons learned from the fate of AstraZeneca's drug pipeline: a five-dimensional framework", Nat Rev Drug Discov., 13(6):419-31 (2014).
Coppeta, et al., "A portable and reconfigurable multi-organ platform for drug development with onboard microfluidic flow control", Lab Chip, 17:134-44 (2017).
Cosgrove, et al, "Synergistic drug-cytokine induction of hepatocellular death as an in vitro approach for the study of inflammation-associated idiosyncratic drug hepatotoxicity", Toxicol Appl Pharmacol., 237(3):317-330 (2009).
Danese, et al., "The CD40/CD40L costimulatory pathway in inflammatory bowel disease", Gut, 53(7):1035-43 (2004).
Denayer, et al., "Animal models in translational medicine: Validation and prediction", New Horizons Transl Med., 2(1):5-11 (2014).
Deng, et al., "Inflammatory stress and idiosyncratic hepatotoxicity: hints from animal models", Pharma Rev., 61(3):262-82 (2009).
Ding, et al., "Bile acid nuclear receptor FXR and digestive system diseases", Acta Pharm Sin B 5(2):135-44 (2015).
Domansky, et al., "Perfused multiwell plate for 3D liver tissue engineering", Lab Chip 10:51-8 (2010).
Ebrahimkhani, et al., "Bioreactor technologies to support liver function in vitro", Adv Drug Deily Rev, Apr(69-70):132-57 (2014).
Esch, et al., "Body-on-a-chip simulation with gastrointestinal tract and liver tissues suggests that ingested nanoparticles have the potential to cause liver injury", Lab Chip 14(16):3081-92 (2014).
Fink, "Animal models of sepsis", Virulence, 5(1):143-53 (2014).
Frey, et al., "The ErbB4 growth factor receptor is required for colon epithelial cell survival in the presence of TNF", Gastroenterology, 136(1):217-26 (2009).
Giese, et al., "Human immunity in vitro—solving immunogenicity and more", Adv Drug Deliver Rev., 69:103-22 (2014).
Guo, et al, "Lipopolysaccharide causes an increase in intestinal tight junction permeability in vitro and in vivo by inducing enterocyte membrane expression and localization of TLR-4 and CD14", Am J Pathol., 182(2):375-87 (2013).
Halldorsson, et al., "Advantages and challenges of microfluidic cell culture in polydimethylsiloxane devices", Biosens. Bioelectron., 63:218-31 (2015).
Huang, et al., "Therapeutic protein-drug interactions and implications for drug development", Clin Pharmacol Ther., 87(4):497-503 (2010).
Huebsch, et al., "Miniaturized iPS-Cell-Derived Cardiac Muscles for Physiologically Relevant Drug Response Analyses.", Sci Rep., 6:24726 (2016).
Huh, et al., "Microengineered physiological biomimicry: organs-on-chips", Lab Chip, 12(12):2156-64 (2012).
Inman, et al, "Design, modeling and fabrication of a constant flow pneumatic micropump", J Micromech Microeng., 17(5):891-9 (2007).
Jang, et al., "On-chip three-dimensional cell culture in phaseguides improves hepatocyte functions in vitro", Biomicrofluidics, 9 034113 1-12 (2015).
Khovidhunkit, et al., "Effects of infection and inflammation on lipid and lipoprotein metabolism: mechanisms and consequences to the host", J Lipid Res., 45(7):1169-96 (2004).
Kim, et al., "Role of Kupffer cells in pathogenesis of sepsis-induced drug metabolizing dysfunction", Fabs J., 278(13):2307-17 (2011).
Kubinyi, "Drug research: myths, hype and reality", Nat Rev Drug Discov 2(8):665-8 (2003).
Leblond, et al., "Regulation of the proprotein convertase subtilisin/kexin type 9 in intestinal epithelial cells", Am J Physiol Gastrointest Liver Physiol., 296(4):G805-15 (2009).

(56) References Cited

OTHER PUBLICATIONS

Liaskou, et al "Innate immune cells in liver inflammation", Mediators Inflamm., 2012:949157 (2012).
Livingston, et al., "Facilitating the commercialization and use of organ platforms generated by the microphysiological systems (Tissue Chip) program through public-private partnerships", Comput Struct Biotechnol J., 14:207-10 (2016).
Long, et al., "Modeling Therapeutic Antibody-Small Molecule Drug-Drug Interactions Using a Three-Dimensional Perfusable Human Liver Coculture Platform", Drug Metab Dispos., 44(12):1940-8 (2016).
Loskill, et al., "μOrgano: A Lego®-Like Plug & Play System for Modular Multi-Organ-Chips", Plos One, 10(10):e0139587 (2015).
Marx, "Organs from the lab", Nature, 522:373-7 (2015).
Maschmeyer, et al., "A four-organ-chip for interconnected long-term co-culture of human intestine, liver, skin and kidney equivalents", Lab Chip, 15(12):2688-99 (2015).
Materne, et al., "A multi-organ chip co-culture of neurospheres and liver equivalents for long-term substance testing", J Biotechnol., 205:36-46 (2015a).
Materne, et al, "The Multi-organ Chip—a Microfluidic Platform for Long-term Multi-tissue Coculture", J. Vis. Exp., 98:52526 (2015b).
Mestas, et al., "Of mice and not men: differences between mouse and human immunology", J Immunol. 172(5):2731-8 (2004).
Morgan, "Regulation of cytochrome p450 by inflammatory mediators: why and how", Drug Metab Dispos., 29(3):207-12 (2001).
Nesseler, et al., "Clinical review: The liver in sepsis", Crit Care, 16(5):235 (2012).
Ng, et al., "A Comparative Study of Transmembrane Diffusion and Permeation of Ibuprofen across Synthetic Membranes Using Franz Diffusion Cells", Pharmaceutics, 2:209-23 (2010).
Oleaga., et al., "Multi-Organ toxicity demonstration in a functional human in vitro system composed of four organs", Sci. Rep., 6:20030 (2016).
Pierrakos, et al., "Sepsis biomarkers: a review", Crit Care, 14(1):R15 (2010).
Pillai, et al., "A sensitive and specific CYP cocktail assay for the simultaneous assessment of human cytochrome P450 activities in primary cultures of human hepatocytes using LC-MS/MS", J Pharm Biomed Anal., 74:126-32 (2013).
Powers, et al., "A microfabricated array bioreactor for perfused 3D liver culture", Biotechnol Bioeng., 78:257-69 (2002).
Roth, et al., "The application of 3D cell models to support drug safety assessment: opportunities & challenges", Adv Drug Deliver Rev., 69-70:179-189 (2014).
Rowlands, et al., "The gastrointestinal tract as a barrier in sepsis", Br Med Bull., 55(1):196-211 (1999).
Sarkar, et al., "Metabolite profiling and pharmacokinetic evaluation of hydrocortisone in a perfused three-dimensional human liver bioreactor", Drug Metab Dispos., 43(7):1091-9 (2015).
Seok, et al., "Genomic responses in mouse models poorly mimic human inflammatory diseases", PNAS, 110(9):3507-12 (2013).
Sung, et al., "Microfabricated mammalian organ systems and their integration into models of whole animals and humans", Lab Chip, 13(7):1201-12 (2013).
Sung, et al., "A microfluidic device for a pharmacokinetic-pharmacodynamic (PK-PD) model on a chip", Lab Chip 10:446-55 (2010).
Sung, et al., "A micro cell culture analog (microCCA) with 3-D hydrogel culture of multiple cell lines to assess metabolism-dependent cytotoxicity of anti-cancer drugs", Lab Chip 9:1385-94 (2009).
Sweeney, et al., "A cell culture analogue of rodent physiology: Application to naphthalene toxicology", Taxied. Vitr. 9:307-16 (1995).
Toepke, et al., "PDMS absorption of small molecules and consequences in microfluidic applications", Lab Chip 6:1484-6 (2006).
Trietsch, et al., "Microfluidic titer plate for stratified 3D cell curture", Lab Chip 13:3548-54 (2013).
Tsamandouras, et al., "Wuantitative assessment of population variability in hepatic drug metabolism using a perfused 3D human licer microphysiological", J Pharma Exp Thera., DOI: 10.1124/jpet.116.237495 (2016).
van Midwoud, et al., "A microfluidic approach for in vitro assessment of interorgan interactions in drug metabolism using intestinal and liver slices", Lab Chip 10(20):2778-86 (2010).
Vulto, et al., "Selective sample recovery of DEP-separated cells nd particles by phaseguide-controlled laminar flow", J Micromech Microeng., 16:1847-53 (2006).
Wikswo, et al., "The relevance and potential roles of microphysiological systems in biology and medicine", Exp Biol Med (Maywood) 239(9):1061-72 (2014).
Yamaoka, et al., "Transactivation of EGF receptor and ErbB2 protects intestinal epithelial cells from TNF-induced apoptosis", PNAS, 105(33):11772-7 (2008).
Yates, et al., "Novel three-dimensional organotypic liver bioreactor to directly visualize early events in metastatic progression", Adv. Cancer Res. 97, 225-46 (2007).
Yu, et al., "Three dimensional human small intestine models for ADME-Tox studies", Drug Discovery Today, 19(10):1587-94 (2014).
Zhang, et al., "ErbB2 and ErbB3 regulate recovery from dextran sulfate sodium-induced colitis by promoting mouse colon epithelial cell survival", Lab Invest 92(3):437-50 (2012).
Zhu, et al., "A vertical-flow bioreactor array compacts hepatocytes for enhanced polarity and functions", Lab Chip, 16(20):3898-908 (2016).
Busek, et al., "Design, characterization, and modeling of microcirculations systems with integrated oxygenators", Journal of Sensors and Sensor Systems, 5(1):221-228 (2016).
International Search Report PCT/US2019/022887 dated Jul. 25, 2019.
Berthier, et al., "A general condition for spontaneous capillary flow in uniform cross-section microchannels", Microfluid Nanofluid, 16:77-785 (2014).
Busek, et al., "Hypoxia-on-a-chip", Current Directions in Biomedical Engineering, 2(1):71-75 (2016a).
Concus, et al., "On the behavior of a capillary surface in a wedge", PNAS, 63:292-9 (1969).
Gimbel, et al., "Development of a biomimetic microfluidic oxygen transfer device", Lab Chip, 16:3227-34 (2016).
Heckele, et al., "Review on micro molding of thermoplastic polymers", J. Micromech. Microeng. 14:R1-R14 (2004).
Hoganson, et al., "Lung assist device technology with physiologic blood flow developed on a tissue engineered scaffold platform", Lab Chip, 11 :700-7 (2011).
Lam, et al., "A microfluidic oxygenator for biological cell culture", Transducers and Eurosensors, 2489-2492 (2007).
Liston, et al., "Plasma surface modification of polymers for improved adhesion: a critical review", J Adhesion Sci Tech, 7:1091-1127 (1993).
Low, et al., "Microphysiological Systems ("Organs-on-Chips") for Drug Efficacy and Toxicity Testing", Clin Transl Sci, 10:237-9 (2017).
Minuth, et al., "Supportive development of functional tissues for biomedical research using the Minusheet perfusion system", Clinical and Translational Medicine, 1 (1): (2012).
Oliver, et al., "Resistance to spreading of liquids by sharp edges", J Colloid Interface Sci, 59:568-81 (1977).
Oomen, et al., "Implementing oxygen control in chip-based cell and tissue culture systems", Lab Chip, 16:3394-414 (2016).
Sander, "Compilation of Henry's law constants (Version 4.0) for water as solvent", Atmospheric Chemistry and Physics, 15(8):4399-981 (2015).
Sonntag, et al., "Universallab-on-a-chip platform for complex, perfused 3D cell cultures", Progress in Biomedical Optics and Imaging, SPie—Interntional Society for Optical Engineering, 9705 (2016).
Tao, et al., "Microparticle, nanoparticle, and stem cell-based oxygen carriers as advanced blood substitutes", Trends Biotechnol, 32:466-73 (2014).

(56) References Cited

OTHER PUBLICATIONS

Tygstrup, et al., "Determination of the hepatic arterial blood flow and oxygen supply in man by clamping the hepatic artery during surgery", J Clin Invest, 41 :447-54 (1962).

Volmer, et al., "Development of an integrated microfluidic platform for dynamic oxygen sensing and delivery in a flowing medium", Lab Chip, 5(10):1059-66 (2005).

Walker, et al., "Design, modeling and fabrication of a constant flow pneumatic micropump", J Micromechanics and Microengineering 17(5):891 (2007).

Wang, et al., "A novel in vitro flow system for changing flow direction on endothelial cells", J Biomech, 45:1212-8 (2012).

Wenger et al., "Frequently asked questions in hypoxia research", Hypoxia, 3:3-435 (2015).

Wijs, et al., "Wetting Forces and Meniscus Pinning at Geometrical Edges", Separations: Materials, Devices and Processes, 62(12):4453-65 (2016).

Wu, et al., "Lung assist device: development of microfluidic oxygenators for preterm infants with respiratory failure", Lab Chip, 13:2641-50 (2013).

Xia, et al., "Soft Lithography", Ann. Rev. Mater. Sci., 28:153-84 (1998).

Young, et al., "Contoured elastic-membrane microvalves for microfluidic network integration", J. Biomech. Eng., 121:2-6 (1999).

Domansky, et al., "Multiwell cell culture plate format with integrated microfluidic perfusion system", Proceedings vol. 6112, Microfluidics, BioMEMS, and Medical Microsystems IV; 61120F (2006).

Domansky, et al., "Perfused Microreactors for Liver Tissue Engineering", Proceedings of the 2005 IEEE, Engineering in Medicine and Biology 27th Annual Conference (2005).

\* cited by examiner

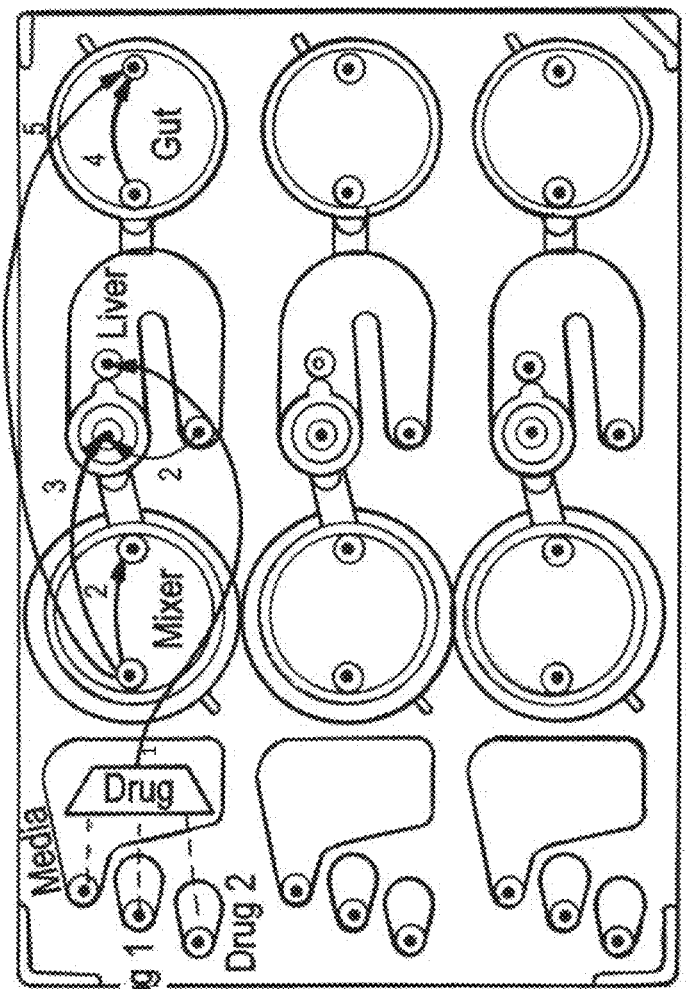
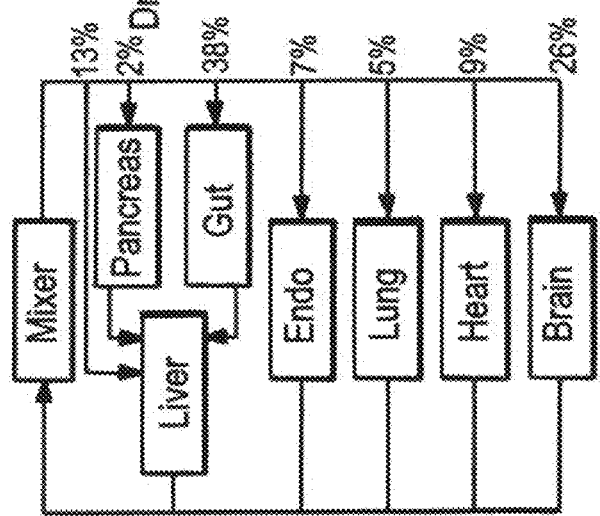
FIG. 11
FIG. 10

|  | Rounded | Knife Edge | V-cut |
|---|---|---|---|
| Inlet | 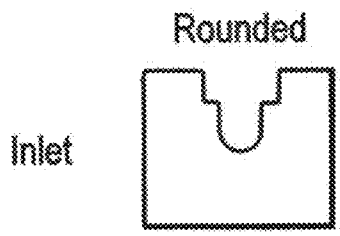<br>FIG. 26A | 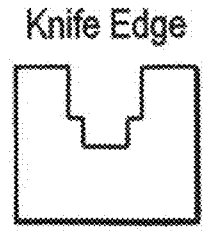<br>FIG. 27A | 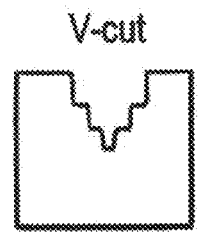<br>FIG. 28A |
| Diagonal | 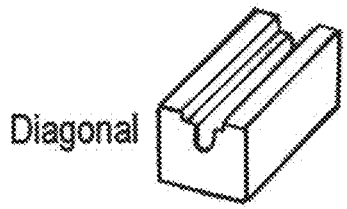<br>FIG. 26B | 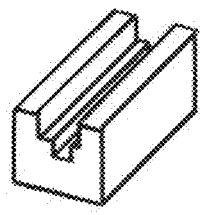<br>FIG. 27B | 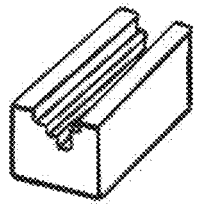<br>FIG. 28B |
| Section | 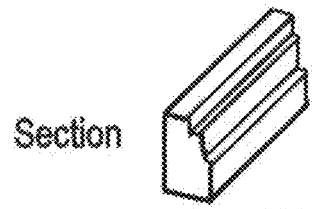<br>FIG. 26C | 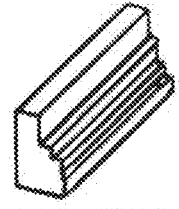<br>FIG. 27C | 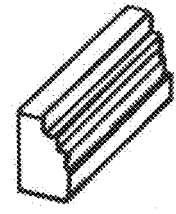<br>FIG. 28C |
| Outlet | 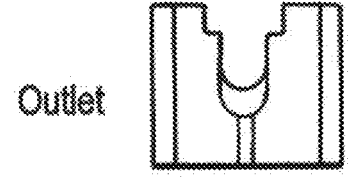<br>FIG. 26D | 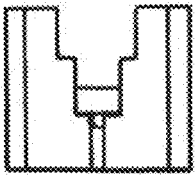<br>FIG. 27D | <br>FIG. 28D |
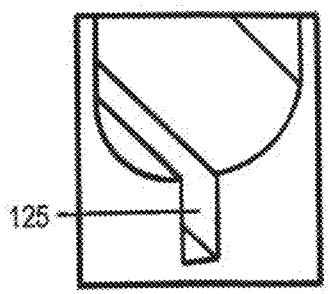
FIG. 29

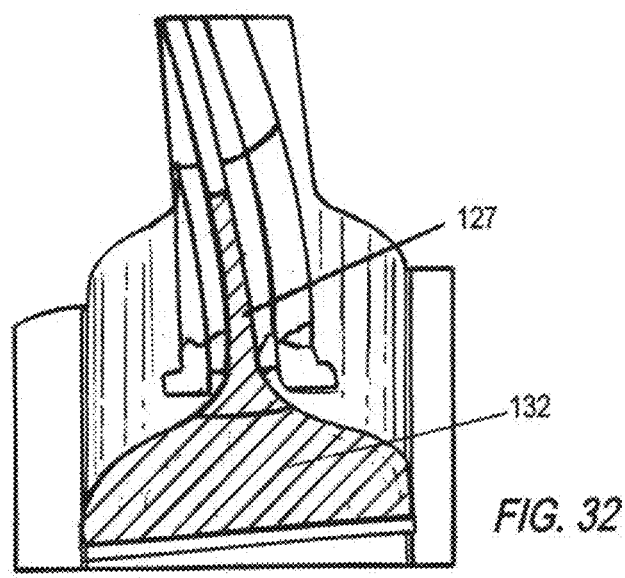
FIG. 32
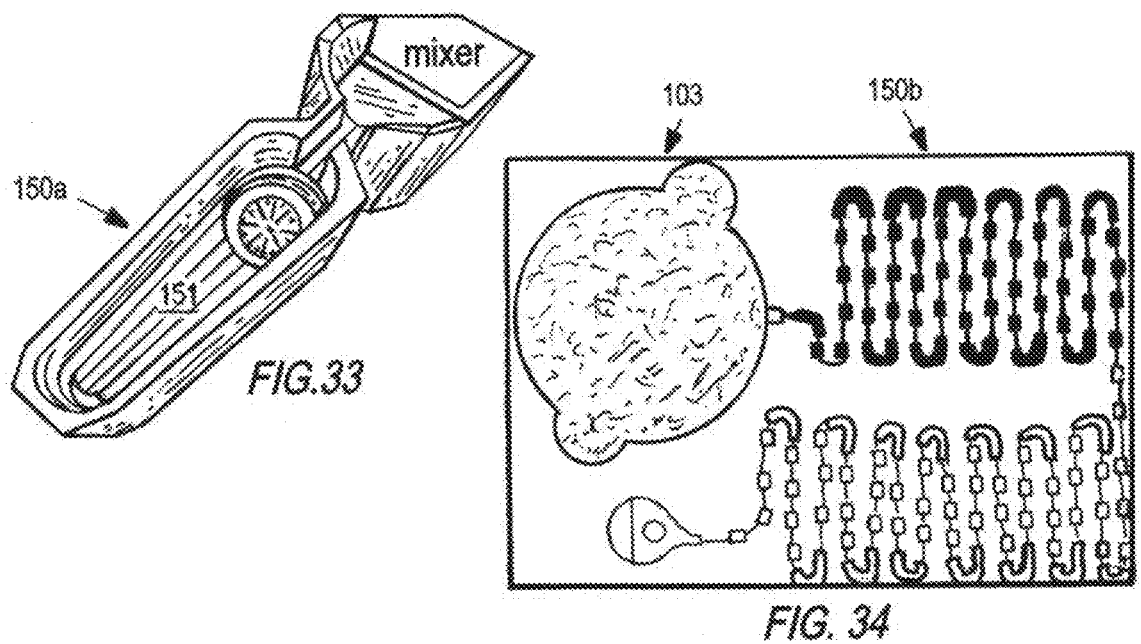
FIG. 33
FIG. 34
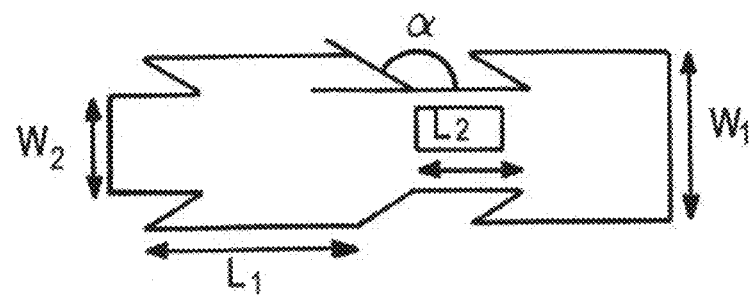
FIG. 35

MODULAR ORGAN MICROPHYSIOLOGICAL SYSTEM WITH INTEGRATED PUMPING, LEVELING, AND SENSING

CROSS-REFERENCE TO RELATED APPLICATIONS

This application claims priority to and benefit of U.S. Provisional Application No. 62/291,102 filed Feb. 4, 2016 and U.S. Provisional Application No. 62/359,567 filed Jul. 7, 2016, which are hereby incorporated herein by reference in its entirety.

STATEMENT REGARDING FEDERALLY SPONSORED RESEARCH OR DEVELOPMENT

This invention was made with government support under Contracts W911NF-12-2-0039 and UH3TR000496 awarded by the Defense Advanced Research Projects Agency Microphysiological Systems Program and National Institutes of Health, respectively. The government has certain rights in the invention.

BACKGROUND OF THE INVENTION

Improving the effectiveness of preclinical predictions of human drug responses is critical to reducing costly failures in clinical trials. Complex diseases often arise from dysregulation of systemic regulatory networks, including across multiple organs, resulting from integration of local and systemic perturbations. Incomplete understanding of inter-tissue communication can undermine the accurate diagnosis and treatment of disease conditions. Although the study of human pathophysiology has relied on genetically tractable animal models such as murine models, these animal models may be inadequate for recapitulating polygenic and multifactorial human diseases with diverse clinical phenotypes.

Recent advances in cell biology, microfabrication and microfluidics have enabled the development of micro engineered models of the functional units of human organs—known as organs-on-a-chip (OCC)—that could provide the basis for preclinical assays with greater predictive power. For example, U.S. Pat. No. 6,197,575 to Griffith, et al., describes a micromatrix and a perfusion assembly suitable for seeding, attachment, and culture of complex hierarchical tissue or organ structures. U.S. Pat. No. 8,318,479 to Inman, et al., describes a system that facilitates perfusion at the length scale of a capillary bed suitable for culture and assaying in a multiwell plate format.

These platforms, termed microphysiological systems (MPSs), are designed to mimic physiological functions by integrating tissue engineering principles with microfabrication or micromachining techniques for recapitulating 3D multicellular interactions and dynamic regulation of nutrient transport and/or mechanical stimulation (Huh D, et al., *Lab Chip,* 12(12):2156-2164 (2012); Sung J H, et al. *Lab Chip* 13(7):1201-1212 (2013); Wikswo J P, et al., *Exp Biol Med* (Maywood) 239(9):1061-1072 (2014); Livingston C A, et al., *Computational and Structural Biotechnology Journal* 14:207-210 (2016); Yu J, et al., *Drug Discovery Today,* 19(10):1587-1594 (2014); Zhu L, et al. *Lab Chip,* 16(20): 3898-3908 (2016)). While significant advances have been made in the development of individual MPS (e.g., cardiac, lung, liver, brain) (Roth A, et al., *Adv Drug Deliver Rev,* 69-70:179-189 (2014); Huebsch N, et al. *Scientific Reports,* 6:24726 (2016); Domansky K, et al. *Lab Chip* 10(1):51-58 (2010)), efforts towards the interconnection of MPS are still in their infancy, with most studies primarily focused on basic viability and toxicity demonstrations (Oleaga C, et al. *Sci Rep* 6:20030 (2016); Esch M B, et al., *Lab Chip* 14(16): 3081-3092 (2014); Maschmeyer I, et al., *Lab Chip* 15(12): 2688-2699 (2015); Materne E M, et al. *J Biotechnol* 205: 36-46 (2015); Loskill P, et al., Plos One 10(10):e0139587 (2015)). However, lack of clinical efficacy, rather than toxicity, was identified as the leading cause of drug attrition in Phase II and III clinical trials (the most costly stage) (Kubinyi H, *Nat Rev Drug Discov* 2(8):665-668 (2003); Cook D, et al. Nat Rev Drug Discov 13(6):419-431 (2014); Denayer T, et al., *New Horizons in Translational Medicine,* 2(1):5-11 (2014)). Major contributing factors include incomplete understanding of disease mechanisms, the lack of predictive biomarkers, and interspecies differences. There is an urgent unmet need in drug development due to the need for humanized model systems for target identification/validation and biomarker discovery.

The increasing need for more predictive in vitro systems is not limited to single MPS technologies. The complexity of the human physiology can be better recapitulated at a systemic level in multi-MPS platforms, where multi-organ crosstalk and the physiological responses to therapeutic agents and toxins occur via surrogate signals (e.g. chemokines, cytokines, growth factors) and circulating cells (e.g. immune cells). Shuler et al. demonstrated pharmacological applications of multi-compartmental bioreactor systems (Sweeney L M, et al., *Toxicol. Vitr.* 9, 307-316 (1995)). Sung et al. showed a micro cell culture analog (pCCA), where cells were embedded in 3D hydrogels in separate chambers, could be used for interacting MPS systems (Sung J H, et al., *Lab Chip* 9, 1385 (2009)). Some prototypes use gravitational flow for inter-MPS communication (Sung J H, et al., *Lab Chip* 10, 446-455 (2010)). Some prototypes of the three-MPS system use off-platform pumping with a bubble trap (Sung J H, et al., *Lab Chip* 9, 1385 (2009); Esch M B, et al. *Lab Chip* 14, 3081 (2014)).

While toxicology and pharmacodynamic studies are common applications, pharmacokinetic studies have been limited in multi-MPS platforms. Moreover, current multi-MPS systems generally employ a closed format associated with traditional microfluidic chips for operating with very small fluid volumes (Anna S L, *Annu. Rev. Fluid Mech.* 48, 285-309 (2016)). Current fabrication processes for these systems require the use of castable elastomeric polymers like PDMS mainly for desirable optical properties, but due to fluid-surface interactions such as drug and growth factor adsorption are commonly present (Halldorsson S, et al., *Biosens. Bioelectron.* 63, 218-231 (2015)).

Other practical limitations in the design and fabrication of the hardware also significantly reduce the robustness, long-term reliability, and compatibility of customization in existing multi-MPS devices. Poor hardware designs and constructs often result in a poor of lack of control on the directionality of fluid among wells (inter-well directionality) and within-well recirculation, leaving some wells dry due to breakage of fluid flow, the syphoning effect, and/or evaporation. Media depletion and waste removal at near-physiological scales often require single-pass media flow, making it difficult or impossible to study slow-clearing drugs, effects of drug metabolites, and inter-MPS communications. Removable inserts to fit into the wells of multi-MPS devices may be desirable in culturing some tissues, but their compatibility with fluid in-flow to support perfusion of cultures has been difficult to achieve.

It is therefore an object of the present invention to provide improved apparatus with integrated fluid control means for long-term tissue culture and facile assaying of multiple modular organ models.

It is another object of the present invention to provide methods of integrating fluid pumping, leveling, and sensing with bioreactors.

It is yet another object of the present invention to provide insert devices compatible with open fluid bioreactors, which support perfusion and allow off-platform seeding of cells and biomaterials, simple manipulation, and easy removal from bioreactors without causing damage or contamination.

SUMMARY OF THE INVENTION

Multi-well cell culture systems (or organs-on-a-chip devices, microphysiosome bioreactors) are provided with integrated pumping, spontaneous liquid leveling, and programmable drug/media dosing. A multi-well culture system, i.e., a chip or a bioreactor, contain at least three layers of constructs, which from top to bottom are (1) a multi-well cell culture plate construct with built-in fluid channels (e.g., fluid paths) below and connected to the wells, (2) a barrier membrane as a pump actuator, and (3) a pneumatic plate to present pressure and vacuum. In different embodiments, the membrane layer is bonded on either the fluidic or the pneumatic side, or is a separate component. Bonding the membrane layer to the pneumatic or fluidic side enhances reliability and reduces manufacture time and cost. In a preferred embodiment, the membrane is bonded to the pneumatic side, and the fluidic layer is open faced, making cleaning and sterilization easier. In some embodiments, no bonding on the fluidic side eliminates delamination.

Pneumatic control of vacuum or pressure causes the membrane to actuate, which acts like a valve to control the passage or blockade on the fluid channel, thus the fluid flow, on the fluidic side of the system. Fluid such as cell culture media is flowed in to fill at least one of the wells, and passive self-leveling spillways connecting two or more wells in the upper space allow for transfer of excess fluid from one well to another. Recirculation within a well or between two wells is allowed actively, through additional pumps.

The system combines one or more of the following features to improve the operability and performance of modeled organs on a chip: Spillways having defined geometric arrangements to promote unidirectional flow and anti-siphon capability. One or more features in the entry, the conduit, and/or the exit of the spillway are provided to ensure spontaneous capillary flow across the spillway for unidirectional self-leveling of fluid amount in MPS chambers. Some embodiments provide entry geometry that eliminates a step or V-cut to minimize fluid film disruption; and includes a radial meniscus pinning groove around the source well, the groove being able to "pin" the fluid meniscus, making a specified fluid height energetically favorable.

Some embodiments provide a spillway conduit that has a small-width (e.g., less than 3 mm), high aspect ratio groove at the bottom along the conduit to permit spontaneous capillary flow, thus leveling of excess fluid from the source well to the destination well. Some embodiments provide exit geometry where the groove at the end of the spillway conduit encounters an enlarged, curved area, to thin the fluid film, thereby breaking it into drops which coalesce and fall due to gravity. In another embodiment, at the exit of spillway there is a vertical groove along the wall and toward the bottom of the destination well. Some embodiments additionally provide an undercut into the wall of the destination well, where the cut is at some distance below the exit of the conduit, to prevent back flow due to siphoning effect. These features allow a self-leveling spillway in a unidirectional flow and prevent breakage of flow and over accumulation in the source well or the conduit.

Optionally coupled with an internal humidity reservoir or an evaporation-combatting moat, the multi-organ MPS platforms allow for long-term culture of functional organ-like tissues, e.g., for at least 1, 2, 3, 4, 5, 6 weeks or at least 1, 2, 3 months.

The on-board pumping system (e.g., built-in fluid pumping channels) eliminates the need for tubing, but modular pumping can be configured to drive external flows. Ferrule connections may be used to interface the built-in pump with external tubing, allowing for a pumping manifold to drive a large number of flows simultaneously in a compact package.

A dual pumping system in addition to single multi-chamber unit pumping system permits not only pulsating flow but also a smooth flow volume profile. A triple pumping system or more parallel channels may further increase the smoothness of the flow.

A removable yet perfusion-enabled scaffold to fit into the wells on the platform is provided. Unlike conventional removable inserts that do not allow integrable features to participate in the perfusion process in a bioreactor, the scaffold enables cell culture to be perfused on-platform and processed off-platform. The scaffold may optionally contain a fluid aggregation lid for non-contact oxygen ($O_2$) sensing.

One or more means for non-contact fluid leveling sensing are provided. Capacitors with a symmetrical, front-and-back electrode design provides accurate measurement of fluid level in a well from within the wall of the well, avoiding direct contact, electrochemical reactions, and potential contamination.

Two or more multi-organ bioreactors may be daisy chained due to the pass-through design of internal channels (e.g., air actuation lines) passing through the body of the pneumatic plate of the bioreactor. Two or more bioreactors may also be stacked to save space. Pneumatic line and fluid connection layouts for stacked configuration are provided.

The platform is preferably fabricated from materials that minimize loss of biochemical factors due to adsorption. In some embodiments, the top fluidic plate is fabricated from polysulfone. In some embodiments, the top fluidic plate is fabricated from polystyrene. In some embodiments, the pneumatic plate is fabricated from acrylic material. In some embodiments, the actuation membrane is fabricated from polyurethane; alternatively elastomers are placed on the multi-chamber pumping unit in sections to replace the polyurethane membrane.

The organ-on-chip has on-board pneumatic microfluidic pumping in order to achieve extended 3D culture of functional tissue such as liver tissue. The on-board pumping technology minimizes space, auxiliary equipment, and dead volumes associated with excess tubing. This multi-organ platform features deterministic pumping for precise flow rate control over a wide range of flow rates from 0 to several hundreds of milliliters per day with controlled volume flux such as between 0.1 and 10 microliter per stroke, at frequencies between about 0.01 Hz and 20 Hz, to provide controlled recirculation of medium within each MPS as well as controlled "systemic" circulation.

The platform has a similar footprint to a typical multi-well plate with chambers designed to house different types of micro-tissues. The individual tissue compartments are equipped with their own intra-MPS pumps to provide nutrient recirculation and are fluidically connected to the mixer via passive spillways for level control. Although one-organ culture is feasible with the platform (e.g., with benefits of perfusion and drug addition coming from other wells), the hardware can be reconfigured to accommodate multiple applications including 2-way, 3-way, 4-way and N-way interactions (N>=2), with user-defined control of flow rates and flow partitioning from the mixing chamber to the different tissues, recapitulating physiologically-relevant circulation.

Validations of multi-way MPS interactomes are also provided. "M-W MPS" refers to a configuration whereby each individual micro physiological system has its own internal circulation to control oxygenation and mixing and mechanical stimulation independent of other MPS units on the platform. Each MPS is connected fluidically to other MPS units in a controlled manner via the central circulatory flow circuit, or via direct connections. For example, the gut module has an internal circulation to mix the fluid beneath the transwell membrane and receives flow from the central circulatory flow, then its effluent goes directly to the liver. The liver module has its own internal circulatory flow, and receives flow from the gut, the pancreas, and the central circulatory flow.

BRIEF DESCRIPTION OF THE DRAWINGS

FIG. 10 is a diagram showing the flow directionality, flow partitioning, and cell culture type of each well on a 7-way platform.

FIG. 11 is a diagram of a different configurations of well orientations for drug additions to a 2-way interactome.

FIG. 19 is a schematic of a cross-sectional side view of another embodiment of a spillway geometry. This spillway has a conduit 127 that permits open fluid flow (space above the conduit 126) with a tower conduit 128a entry, and an upward conduit exit 129a.

FIGS. 26A-26D show different views of a rounded bottom spillway conduit at the inlet (FIG. 26A), a diagonal view (FIG. 26B), a section view (FIG. 26C), and at the outlet (FIG. 26D).

FIGS. 27A-27D show different views of a spillway conduit with a knife edge geometry at the inlet (FIG. 27A), a diagonal view (FIG. 27B), a section view (FIG. 27C), and at the outlet (FIG. 27D).

FIGS. 28A-28D show different views of a spillway conduit with a V-cut geometry at the inlet (FIG. 28A), a diagonal view (FIG. 28B), a section view (FIG. 28C), and at the outlet (FIG. 28D).

FIG. 29 is a schematic of the cross-sectional side view of a spillway conduit geometry, i.e., U-shaped with a bottom-located rectangle groove of a high depth-to-width ratio (e.g., greater than 3).

FIG. 32 is a schematic of a top view of a spillway exit geometry where fluid flowing from a small-width groove 127 encounters an enlarged curved area 132 for exit.

FIG. 33 is a schematic of a top view of an oxygenation tail 150a with guiding grooves 151 on the bottom surface of the well.

FIG. 34 is a schematic of a top view of a well 103 connecting to a zig-zag oxygenation tail 150b.

FIG. 35 is a diagram showing the geometry features of the zig-zag oxygenation tail shown in FIG. 34, for a phase-guiding purpose. The tail has a maximum width of $W_1$ and a minimum width of $W_2$, appearing in an alternating order for a length of $L_1$ and $L_2$, respectively. The angle α symbols the direction of an increasing width with respect to the fluid flow direction in the oxygenation tail.

DETAILED DESCRIPTION OF THE INVENTION

I. Definition

Figure 1:
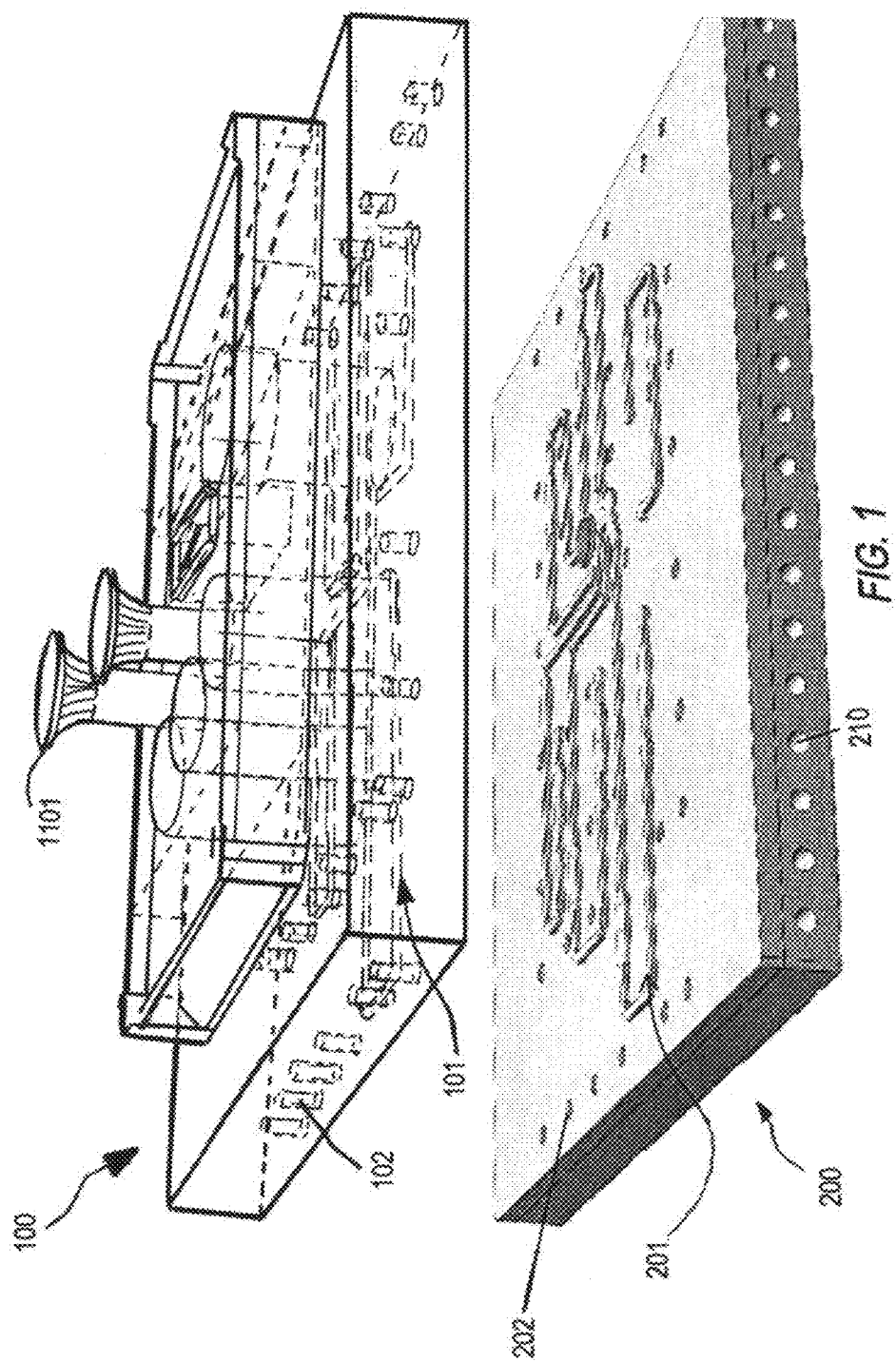
FIG. 1 is an exemplary diagram of components in a multiwell device with on-board pumping system. A fluidic plate 100 contains two or more wells, which can be fitted with inserts such as a transwell 1101, fluid paths 101 providing fluid connectivity between at least two of the wells, and pin holes or slots 102 for attachment with a second plate 200. The second plate 200 (e.g., a pneumatic plate) contains a number of internal channels (i.e., air actuation lines), each with openings 210 (an inlet opening and an outlet opening) on opposing sides of the second plate 200. On the surface of the second plate is one or more protruding features 201 corresponding to the shape, totuosity, and length of the fluid paths 101 of the fluidic plate 100. These protruding features have holes in connection to each of the internal channel, such that compressed air or vacuum is distributed through the internal channels to holes on the surface of the pneumatic plate. The pneumatic plate also has slots 202 for attachment with the fluidic plate. Stainless steel screws fasten the layers together into a single unit that can be handled like a traditional N-well plate.

The terms "organ-on-chip (OOC)", "bioreactor", and "microphysiological system (MPS)", used interchangeably, refer to the platform providing for interactions among single or multiple organ or other tissue types on an in vitro platform which provides for the maintenance of growth of these tissues.

The term "pneumatic" refers to a system which uses air or vacuum pressure for operation.

The term "manifold" refers to an interconnection device for pneumatic or fluid connections.

The term "spillway" refers to a system of fluidic connections between a source well and a destination well to automatically maintain fluid levels in the source well.

The term "leveling" refers to maintaining fluid level.

The term "self-leveling", refers to maintaining level using passive means, i.e., without active means.

The term "undercut" refers to a mechanical detail associated with an overhanging feature.

The term "wetting" refers to the wetting of a solid surface by a liquid in a gas environment, which is determined by the minimum in Gibbs energy of the system. Wetting of a solid surface by a liquid in a gas environment results in an equilibrium contact angle θ across the liquid phase between the solid/liquid (SL) and liquid/gas (LG) interfaces as they emanate from the contact line. Generally the terms "wetting" and "nonwetting" surface refer to cases of θ<90° and θ>90°, respectively. The relationship between the contact angle and the interfacial energies involved is expressed by Young's equation $\gamma_{SV} = \gamma_{SL} - \gamma \cos \theta$, where $\gamma_{SV}$, $\gamma_{SL}$, and $\gamma$ are the Gibbs interfacial energies between solid and gas, solid and liquid, and liquid and vapor, respectively, and where the last quantity is addressed as surface tension. To satisfy the thermodynamic equilibrium requirement, the gas phase is saturated with vapor.

The term "meniscus" refers to the fluid boundary at the intersection of fluid with a solid material and a vapor phase.

The term "meniscus pinning" herein refers to, in a situation of raising the level of a wetting liquid in a vertical well to the top edge, the end of the wetting line with a contact angle θ stays (or "is pinned") at the top edge of the well while the contact angle θ to rise from <90° to >90° at the top edge of the well side wall during further increase of the liquid level, until accumulation of liquid results in spilling over the edge of the well, thus releasing the contact line ("unpinned"). For nonwetting liquid, meniscus pinning occurs at the base edge and the top edge of the side face of a vertical well, and at the top edge the angle for the liquid orientation at the contact line changes from the value θ to the value θ+90°. Details of the term is described in Wijs et al., *Separations: Materials, Devices and Processes*, 62(12): 4453-4465 (2016).

The term "capillary length" refers to a characteristic length scale for an interface between two fluids which is subject both to gravitational acceleration and to a surface force due to surface tension at the interface.

The term "insert" refers to an element which can be mechanically assembled in a well of an MPS.

The term "scaffold" in the relevant sections is an insert or component of the wells which provides support for tissue constructs.

The term "whippletree" refers to a mechanism to distribute force or pressure evenly through linkages. As used herein, it refers to force or pressure applied from one direction at or near the center and distributes to the tips (generally two tips), where each serves as the center for distribution to further tips.

The terms "program" or "software" refer to any type of computer code or set of computer-executable instructions that can be employed to program a computer or other processor to implement various aspects of embodiments as discussed above. Additionally, it should be appreciated that one or more computer programs that when executed perform methods of the present invention need not reside on a single computer or processor, but may be distributed in a modular fashion amongst a number of different computers or processors to implement various aspects of the present invention.

II. Apparatus and Operation of Apparatus

Each multiwell device is generally a three-component construct with an on-board pumping system. A fluidic plate 100 contains multiple wells, some be fitted with inserts such as a TRANSWELL® 1101 (Corning, distributed also by Sigma-Aldrich), and built-in micromachined fluid paths 101 for distribution of culture medium (FIG. 1). A pneumatic plate 200 distributes compressed air and vacuum to the surface of the pneumatic plate through small holes. A barrier membrane 300 (generally translucent) is situated between the fluidic plate 100 and the pneumatic plate 200, which under pressure may flex to expand or contract, thereby obstructing or clearing corresponding portions of the fluid paths of the fluidic plate. This barrier membrane also provides a sterile barrier, acting as the actuation layer of the pumps and valves.

Figure 2:
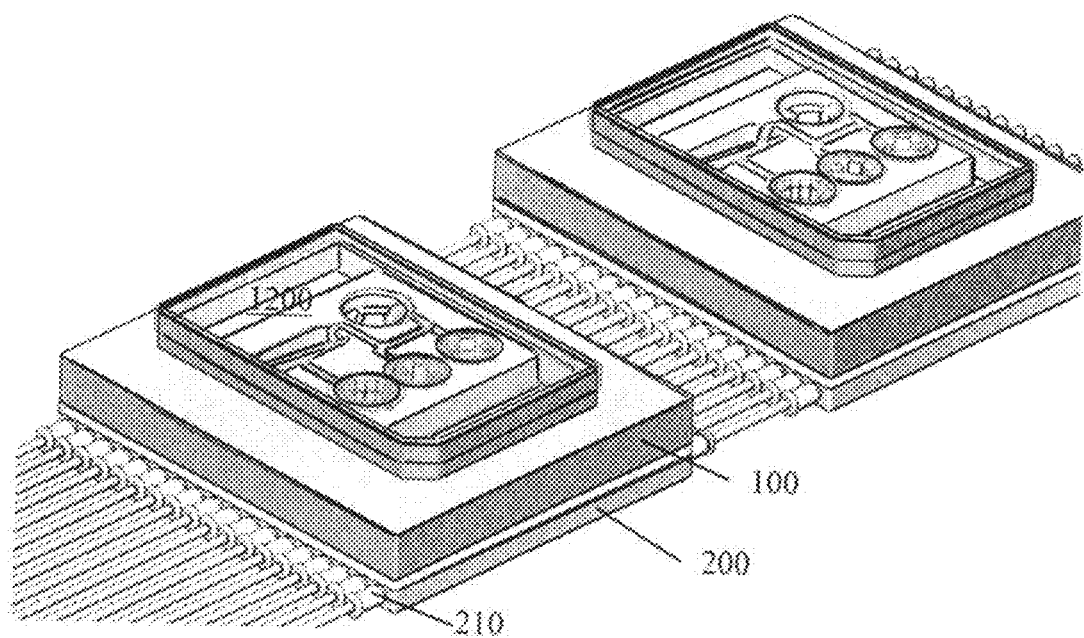
FIG. 2 is a schematic showing two devices daisy-chained at the openings 210 of the internal channels (i.e., air actuation lines) of the pneumatic plate 200. The fluidic plate 100 (with a plate lid 1200) is assembled with the pneumatic plate 200.

Multiple devices can be chained for simultaneous in-phase operation/actuation (FIG. 2). Each device is a bioreactor, which as a platform supports the culture of multiple MPSs mimicking different organs, their interconnections, and interactions as in vivo. The open wells and channels allow users easy access to the cells and culture media to perform measurements requiring direct fluid contact. Up to seven of these MPS have been coupled together, as demonstrated in the examples, although it is understood that the system allows for mixing of more than one of the same type of MPS as well as mixing and integration of a variety of different types, not limited to a total of seven.

The system uniquely incorporates a high degree-of-freedom (DOF) on-board pumping system, effectively configured to support multiple organ culture. While existing devices have compartments linked linearly by a single pump to drive flow through a loop (Materne E M, et al., *J. Vis. Exp.* 1-11 (2015). doi:10.3791/52526) or linked in parallel with channel diameters imposing predefined passive flow rates (Oleaga C., et al., *Sci. Rep.* 6, 20030 (2016)), a high DOF control makes it easy to reconfigure the platform for addition of new MPSs or exclusion of certain compartments.

In some embodiments of 4-way MPS bioreactors, the platform may operate with 18 degrees of freedom ("DOF"), or 18 individual channels of tubing. For example, in a liver-gut-lung-endometrium 4-way MPS, an individually addressable pump requires 3 DOF, while multiple pumps can be run at the same rate by sharing inlets on the pneumatic manifold across multiple pumps. A 4-way MPS platform may have 6 independently programmable flow rates which are used to drive 9 pumps. All four pumps providing mixer-to-MPS flow can be individually addressable. Recirculation pump rates are shared: mixer/liver recirculation are linked, as are gut/lung/endometrium recirculation. It is economically advantageous to link pump rates, as this reduces the number of pneumatic valves and tubing connections required for a platform.

In some embodiments of 7-way MPS bioreactors, the platform has 36 DOFs which operate the functional equivalent of 17 syringe pumps per platform, and can dynamically control intra- and inter-MPS mixing. In this instance, only 12 flow rates can be independently specified, as each requires 3 pneumatic lines.

A. Multi-well Bioreactor

(1) Overview of Directions of Fluid Flow

Figure 3A:
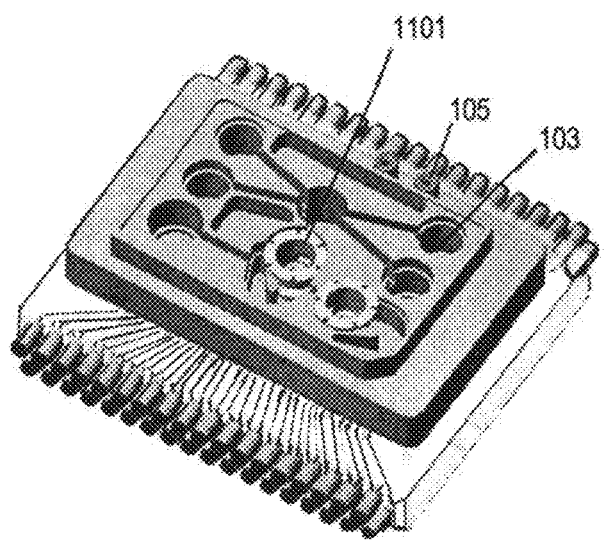
FIG. 3A shows a schematic of an assembled 7-way device, having wells 103 for cell culture and/or mixing medium where a transwell insert 1101 is fitted into a well. Two ports 105 in fluid connectivity with the fluid paths of the fluidic plate may be used to connect with external fluid containers for import and/or export of fluid.
Figure 3B:
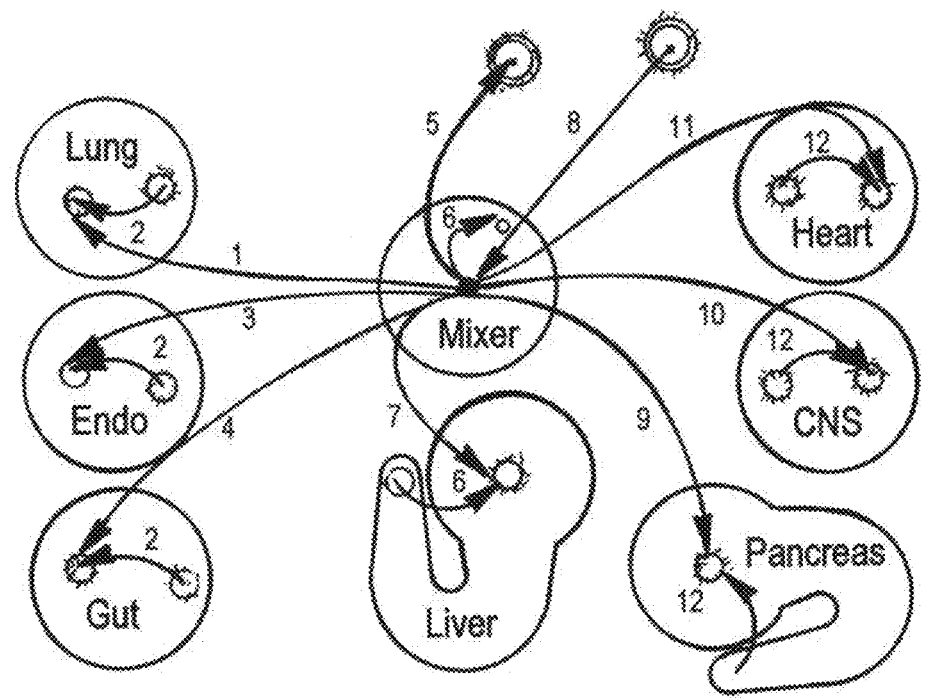
FIG. 3B is a map showing the organs to be placed and flow directionality between organs on a 7-way platform corresponding to FIG. 3A.

FIG. 3A shows a schematic of a 7-organ interactive bioreactor, for which FIG. 3B shows an exemplary map of tissues to be cultured in each well and directions of fluid flow. In an exemplary 7-way bioreactor containing lung, endometrium, gut, liver, heart, central nervous system (CNS), and pancreas, generally active flow of fluid is conducted via built-in fluid channels from the mixer well (Mixer) to lung (arrow 1 in FIG. 3B), from Mixer to endometrium (Endo; arrow 3 in FIG. 3B), from Mixer to gut (arrow 4 in FIG. 3B), from Mixer to liver (arrow 7 in FIG. 3B), from Mixer to pancreas (arrow 9 in FIG. 3B), from Mixer to CNS (arrow 10 in FIG. 3B), from Mixer to heart (arrow 11 in FIG. 3B); and via within-well pumping to recirculate within each of lung, endometrium, gut, heart, CNS, liver, pancreas, and Mixer (arrows 2, 6, and 12 in FIG. 3B). External supply may be imported to Mixer (arrow 8 in FIG. 3B), which through the fluid flow gets distributed to each organ well. Waste from Mixer may be exported to an external collector (arrow 5 in FIG. 3B). In some embodiments, each out-flow from Mixer to an organ has a designated pump for individually controlled flow rates, as well as the external supply import to Mixer and the export of waste to external collector from Mixer. To reduce complexity in some embodiments, the recirculation within each of lung, endometrium, and gut may share one pump control for an identical recirculation flow rate; the recirculation within each of heart, CNS, and pancreas may share another pump control for an identical recirculation flow rate; and the recirculation within Mixer and within liver may share yet another pump control for an identical recirculation flow rate.

Spillways are generally designed between at least one pair of wells, and in one embodiment of the 7-organ platform between lung and Mixer, between endometrium and Mixer, between gut and liver, between liver and Mixer, between heart and Mixer, between CNS and Mixer, and between pancreas and liver, to automatically transfer excess fluid from the former well to the latter.

Figure 4:
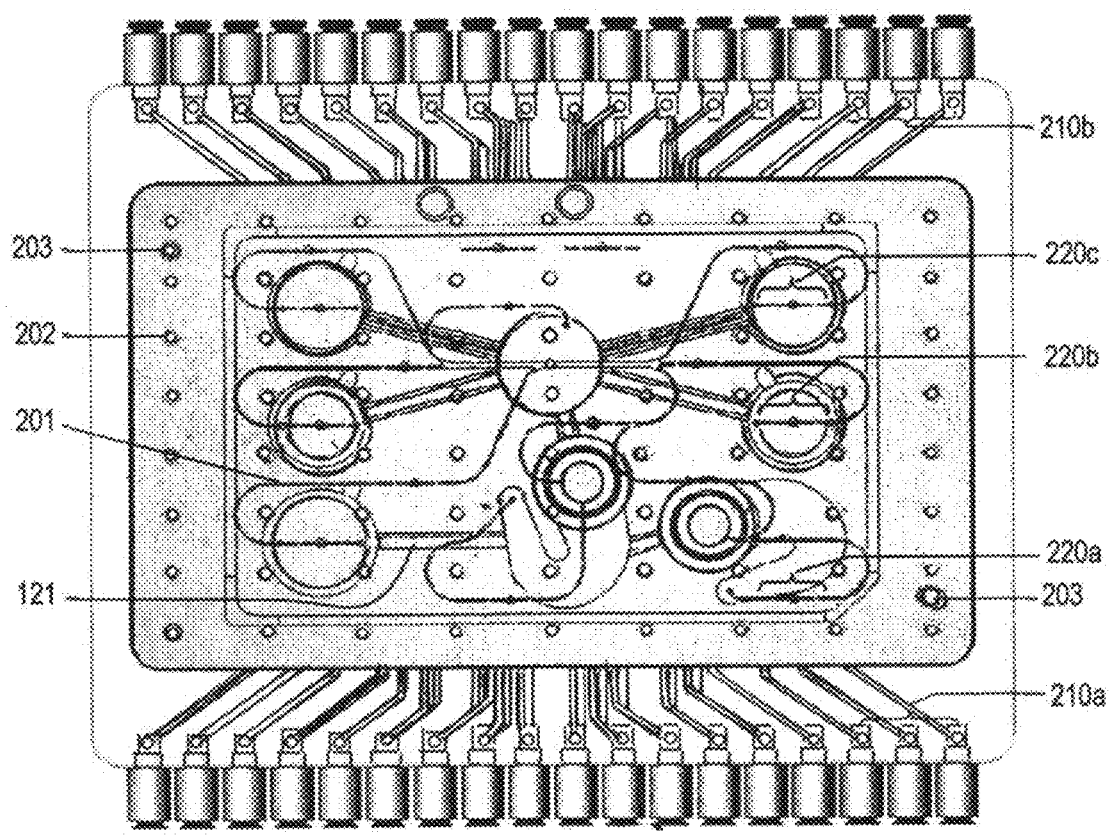
FIG. 4 is a schematic of a top view of a pneumatic plate of a 7-way device. The plate has alignment pins 203 for alignment and slots 202 for attachment with a fluidic plate. The plate has protruding features 201 on the surface which in multiple locations has a set of three holes, representing a set of three-chamber units 220a, 220b, and 220c. These three sets of three-chamber units are in air/pressure connection with three internal channels (i.e., air actuation lines) with inlet and outlet openings 210a and 210b on opposing sides of the pneumatic plate. The middle hole/chamber of each of these three sets of three-chamber units is positioned to share a same internal channel (i.e., air actuation line). The hole/chamber on the same (i.e., left- or right-hand side) of the middle hole/chamber of each of these three sets of three-chamber units is positioned to share another same internal channel (i.e., air actuation line), reducing the complexity of pneumatically actuated flow controls of the device. Corresponding positions of a fluidic plate's wells and spillway conduit 121 are also shown on the pneumatic plate here.

FIG. 4 shows a schematic of the pneumatic bottom plate corresponding to the exemplary 7-way apparatus shown in FIG. 3A for multi-organ culture as mapped out in FIG. 3B. A pneumatic plate may have alignment pins 203, in some embodiments two pins at symmetrical positions about the center, on the side of the pneumatic plate for mating/aligning with corresponding features (e.g., pin holes or slots) on the bottom of the top plate. A pneumatic plate may also have a number of holes 202 throughout the depth of the plate, on multiple locations (not obstructing the air-conducting actuation lines), for corresponding protruding pin features on the bottom of the top fluidic plate to align with. On the pneumatic plate shown in FIG. 4, there are 18 internal channels as air-conducting actuation lines spanning horizontally across the inside of the pneumatic plate. For example, a set of three air-conducting actuation lines with air inlets and air outlets 210a and 210b (entry and exit being relative to the orientation of the plate) controls multiple three-chamber units 220a, 220b, and 220c that are located on the surface of the actuation-side (i.e., the side that through an actuation membrane assembles with the bottom of the fluidic plate) of the pneumatic plate. Each three-chamber unit (e.g., bracketed as 220a, 220b, and 220c) has three chambers, each having an air-conducting hole to the surface connecting with a horizontal air-conducting line below, and three chambers as a whole controls, via pneumatic actuation causing plus and minus deflection of a membrane, the stroke or the peristaltic fluid flow in the fluid channel of a top plate once assembled. The pneumatic plate may also have protruding curved line raised features 201 connecting one or more three-chamber units. These raised features provide the matching sealing surface for the corresponding fluidic channels in the bottom surface of the fluidic plate which conduct fluid in defined fluidic circuits interconnecting the various fluidic MPS modules. These raised features 201 can be seen outlining the positions of fluidic paths in a fluidic plate once the pneumatic plate is assembled with a fluidic plate. Element 121 shows the position of the spillways which carry fluid between the MPS modules in a fluidic plate, once the pneumatic plate is assembled with a fluidic plate.

Figure 5:
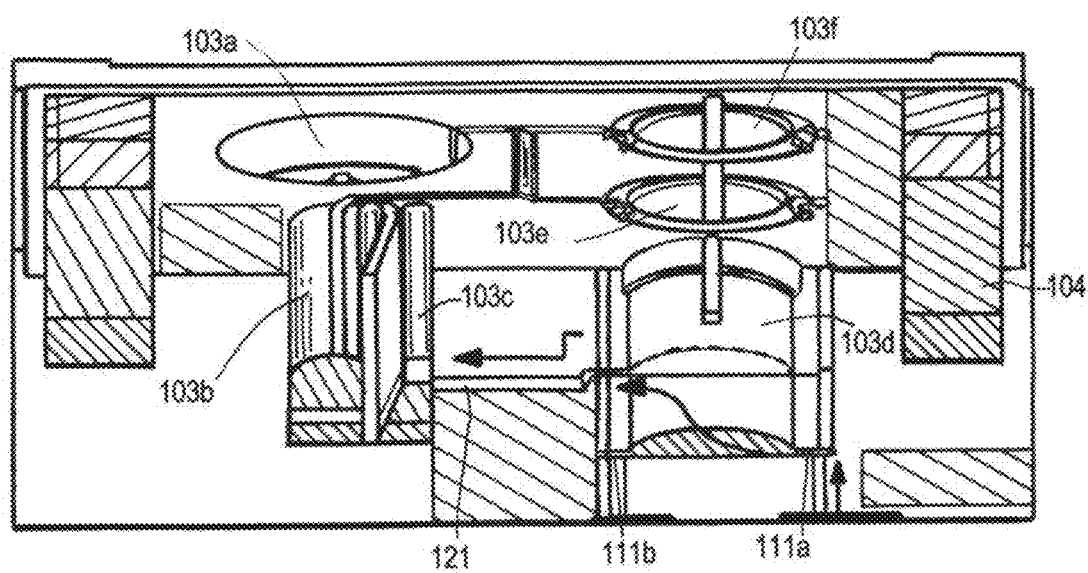
FIG. 5 is a schematic showing a cross-sectional side view of a gut-liver-lung-endometrium 4-way platform. Arrows represent the direction of fluid flow, where fluid is pumped into a gut well 103d via an inlet 111a in the well, and excess fluid above a height is spilled through a spillway conduit 121 to a liver well 103b that contains an oxygenation tail 103c. The gut well also has an outlet 111b in the well for potential same-well recirculation of fluid with inlet 111a. Fluid from a mixer/mixing well 103a flows through fluid paths to cell culture wells including an endometrium well 103e and a lung well 103f. The plate also has a moat 104 to combat evaporation.
Figure 7:
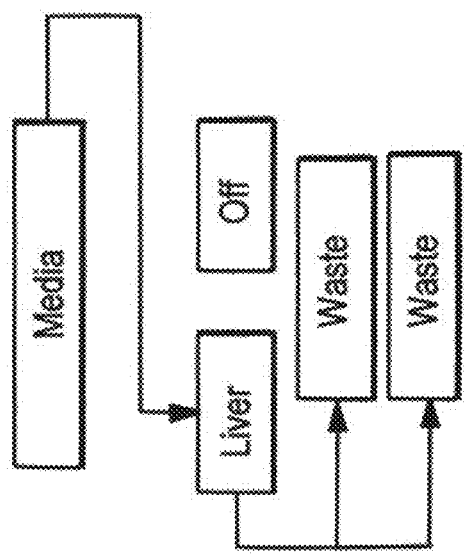
FIG. 7 is a diagram showing of the flow directionality and function of each well on a 4-way platform operating in a one-organ configuration.
Figure 9:
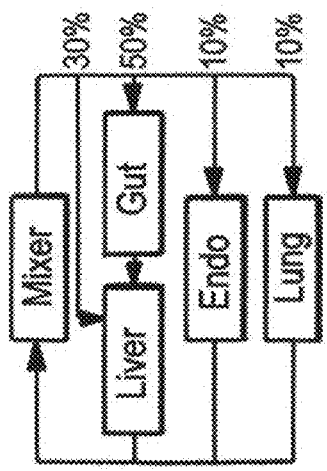
FIG. 9 is a diagram showing the flow directionality, flow partitioning, and cell culture type of each well on another 4-way platform.
Figure 6:
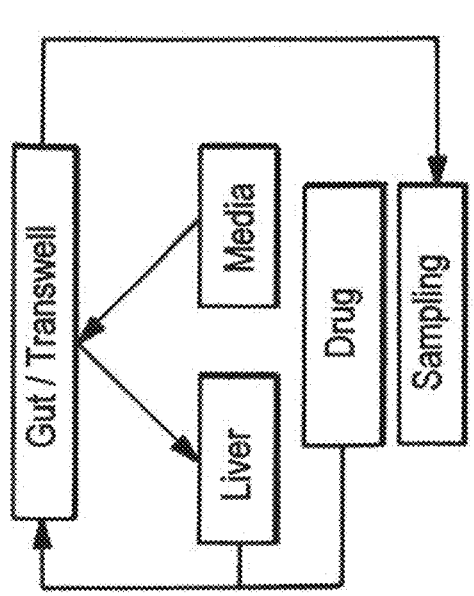
FIG. 6 is a diagram showing the flow directionality and cell culture type of each well on a 4-way platform operating in a two-way configuration.
Figure 8:
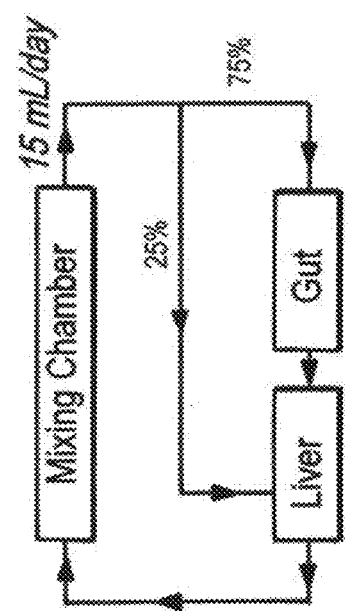
FIG. 8 is a diagram showing the flow directionality, flow partitioning, and cell culture type of each well in a 2-way configuration.

FIG. 5 shows a cross-section of an exemplary 4-way platform showing a built-in channel for fluid flow from mixer to gut, and a general spillway position from gut to liver. The disclosed wells for cell culture on the multi-organ MPS platform generally follow this "flow-in/spill-out" principle of operation.

Operation of the directions of active flow and passive spillover of fluid generally mimic circulation paths in in vivo systems, and the principles as shown in the exemplary 7-organ bioreactor are applicable to platforms of 2-way, 3-way, 4-way, or other numbers of MPS systems. Exclusion of one or more wells from use in a multi-well platform is feasible via alteration in software code for operation, and no hardware change is required. Each well is also reconfigurable for multiple uses. For example, a mixing chamber (Mixer well) may also be used as immune-competent gut MPS well, or be used with a TRANSWELL®. A liver MPS well may be used as a media reservoir or drug reservoir. Exemplary reconfigured use of a multi-well platform is shown in FIGS. 6-10. Flow partitioning is generally achieved by varying the frequency of pumping. Another exemplary configuration of multi-well platform is shown in FIG. 11, where three drugs housed in three wells are delivered to liver well and gut well, while the wells are perfused and in interaction via Mixer well and the spillway between liver and gut.

(2) Means for Controlling Flow Direction and Level Self-Leveling Spillways

Figure 12:
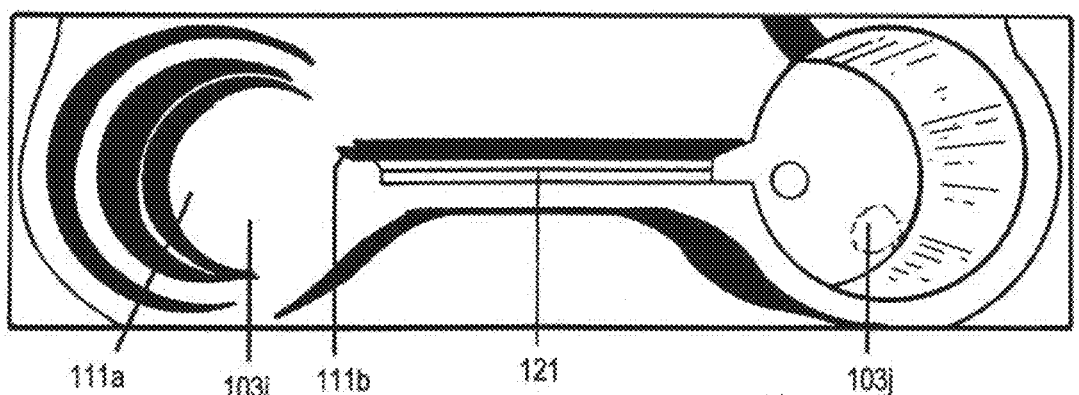
FIG. 12 is a schematic showing a top view of a spillway (containing a spillway conduit 121) providing unidirectional fluid connectivity from a source well 103i to a sink well (or destination well) 103j. The inlet 111a and outlet 111b of the source well 103i are also shown.

The apparatus achieves self-leveling of MPS wells passively and fluid return, generally to Mixer, by a system of spillway channels cut into the top side of the plate to deliver excess fluid back to the mixer. In general, a spillway includes a channel (e.g., open fluid) above certain of the bottom wells, which connects an inlet well to an exit well (FIG. 12). Spillways eliminate the need for return pumps and level sensors for enforcing a balance between influx and efflux, while also allowing return flows to cross over the inlet MPS feed flows. In preferred embodiments, the spillways avoid breakage of fluid flow in the spillway when leveling is needed, and avoid the siphon effect to prevent drying out of wells.

The apparatus uses spontaneous capillary flow (self-wetting) and phase guiding principles to guide flow and wetting in fluid pathways to allow for more robust operation of open fluidic organ-on-chip systems. Unidirectional flow from a source well to a destination well is achieved with meniscus control features, detailed below, and other characteristics including additional groove geometry of the spillway conduit, controlled surface roughness, surface tension, and additional features in the entry and exit of the spillway. These one or more geometric features in fluid containers for the organs-on-chips apparatus allow for pinning of fluid in a radial fashion to limit the meniscus effect created by surface tension. This construction could allow for better passive fluid leveling which could then translate in more deterministic performance and measurement within these systems.

The spillways implement passive leveling in the following fashion. If fluid flow into the inlet well causes a net accumulation of fluid in the inlet well, the level in the inlet well will begin to rise. As the level begins to rise, the fluid will rise at the spillway, and thereby cause increased flow through the spillway into the exit well. If the level in the inlet well decreases, the fluid level at the spillway of the inlet well will drop, thereby decreasing the flow through the spillway. In this manner, the level in the inlet well is passively controlled to be approximately equal to a desired level. Such leveling is passive in that there is not an active process of sensing level and changing some pumping rate in response to this sensing of level. Rather the effects of gravity and surface tension combine to regulate flow in a passive manner not requiring explicit sensing and control.

To achieve proper spilling function, the spillway employs a low resistance flow path in the direction from source to sink, above the designed height of fluid in the source. In some embodiments, the path is impermeable to flow in from the sink to the source and the system, such that as a whole the spillway may be resistant to transient changes in fluid height due to tilting.

Entry Geometry

Various inlet features are useful for stabilizing the source well meniscus, providing an entry into the spillway channel or a way of sealing the volume of the media in the source well.

Figure 16A:
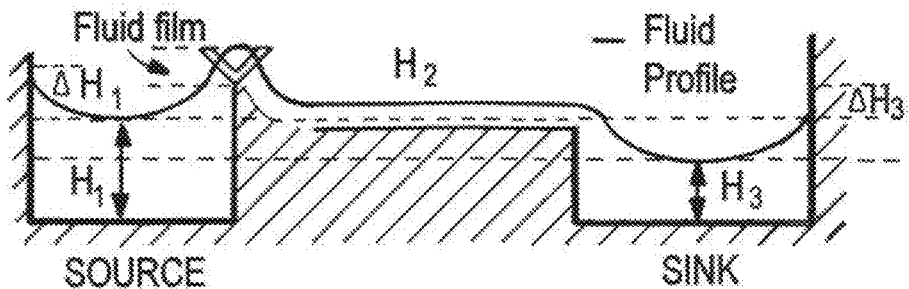
FIG. 16A, FIG. 16B, and FIG. 16C illustrate a successive time-course, potential development of a spillway V-shaped entry geometry of (cross-sectional side view), from initial continuous fluid film across the spillway (FIG. 16A), to breakage of fluid film (FIG. 16B), and finally drying in the sink well and over accumulation in the source (FIG. 16C).
Figure 16B:
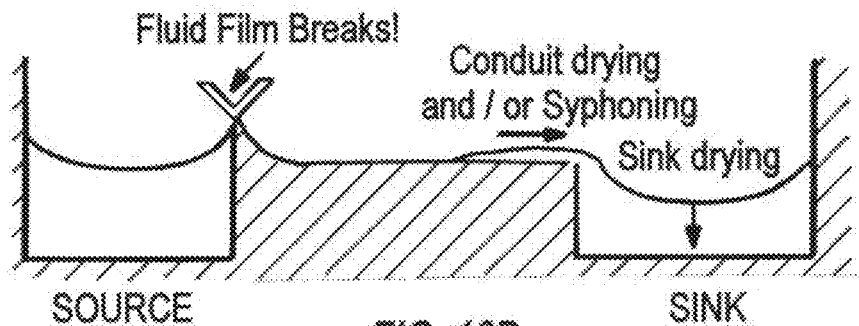
Figure 16C:
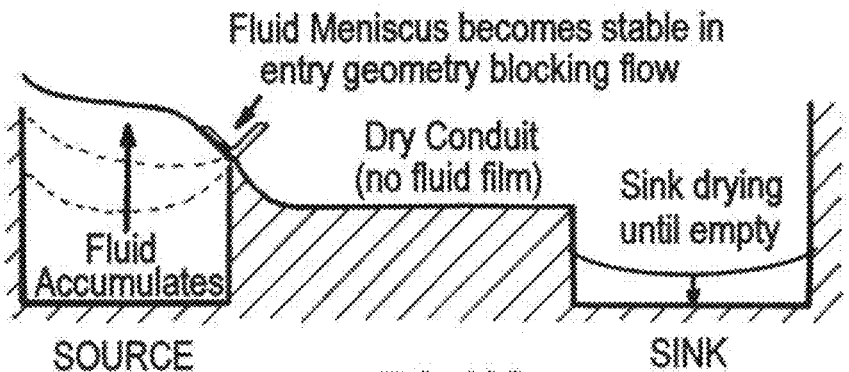

FIGS. 16A-16C show a time-course schematic of how a spillway with a V-cut at the source well (inlet well) experiences discontinuation of the fluid film (e.g., fluid film breaks) and thus the spillway conduit dries, causing fluid to accumulate in the source well and the sink well to dry until empty. This type of spillways start off operating in a meta-stable regime with a connected fluid profile that allows fluid transport. When fluid film breaks (specifically at entry step and V-cut geometries, the fluid finds it more energetically favorable to accumulate in the source well, thus increasing in height, rather than to advance in the spillway entry and spillover into the conduit and sink well (outlet well). When the height increases beyond a certain value, it eventually spills over; but for organs having large surface area, such as pancreas and liver, this increase in height requires a large amount of volume, which was found to be a major reason for the mixer to dry out after 12 hours in incubator in testing of the 7-way platforms using these geometries.

Figure 17:
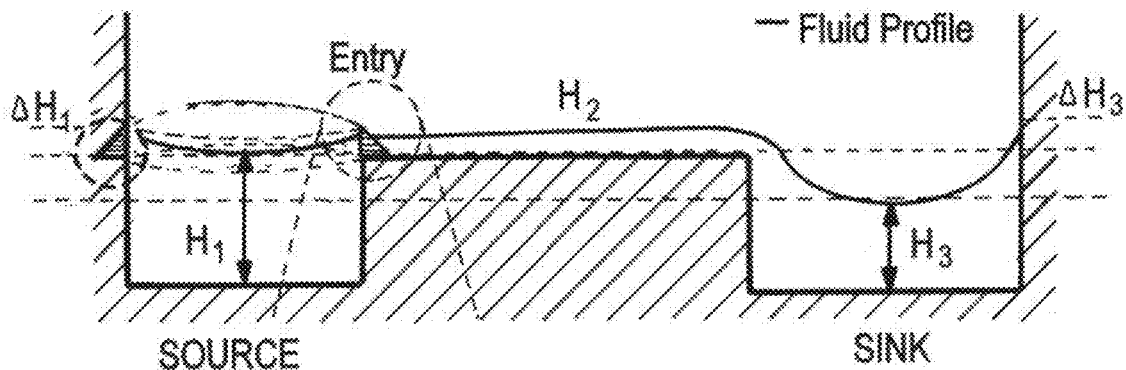
FIG. 17 is a schematic of a cross-sectional side view of another spillway entry geometry without the V-shape in FIG. 16A, for continuous fluid film across the spillway.
Figure 18:
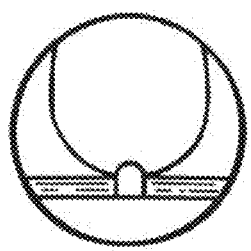
FIG. 18 is a schematic of an enlarged cross-sectional side view of the spillway entry geometry corresponding to FIG. 17, i.e., U-shaped conduit with a groove at the bottom.

The following have been determined to improve efficacy:
Shallow and Gentle Entry for Flat Meniscus Shallower and gentler entry geometry to the spillway minimizes energy for spilling fluid into conduit groove. A radial groove in the source well directs meniscus and makes use of height increases to produce spilling events. When fluid film is present and spillways are conducting fluid, the step and V-cut features may not prevent volume displacement from transient tilting or siphoning. Therefore, for some embodiments, an entry step and a V-cut are eliminated to minimize fluid film disruption at this level. Step barriers may be used to prevent further fluid build-ups, as shown in FIG. 17 with a cross-sectional view of an exemplary entry without the V-cut shown in FIG. 18.

When gravity dominates and surface tension effects are negligible as in large wells with larger interconnecting spillways, V-cuts are effective in determining the exact height of self-levelling and breaking the connection. For smaller geometries, it is more effective to have a direct entry into the spillways (and in one embodiment, have a meniscus pinning groove) and take care of breaking the fluid contact by the use of spillway exit features.

Fluid-Pinning Groove

In some embodiments, the entry to the spillway additionally includes a "fluid pinning" groove, which can be a 20-, 30-, 40-, 45, 50-, or 60-degree circumferential groove 122, preferably 45-degree, in the fluid wells. This groove captures the fluid meniscus, which facilitates maintaining a defined fluid height and improves the dynamics of leveling and spillway operation. The bottom of this radial meniscus pinning groove aligns with the bottom of the spillway fluid flow channel as detailed in FIG. 13. The pinned meniscus is unstable, and thus will spill over, so that the fluid does not rise beyond the height of the radial meniscus pinning groove.

Insertion of Teflon Rings for Deterministic Fluid Level.

Placing Teflon rings at different heights relative to the spillway determines the maximum fluid height before spilling. An inserted Teflon ring captures meniscus, therefore securing the liquid level not to go pass it. The ring also helps prevent evaporation.

Embodiments

Figure 13:
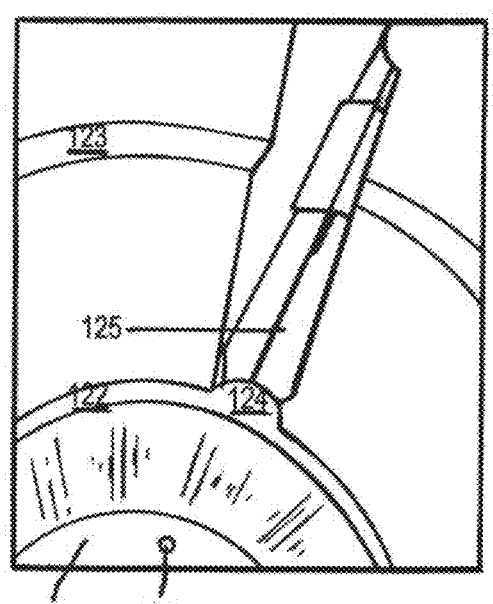
FIG. 13 is a side view of the entry geometry for a spillway from a source well 103i (containing an outlet hole 111b, e.g., for active pumping-induced recirculation). Radial meniscus pinning groove 122 aligns with a curved entry geometry 124 of the spillway, and the curved entry geometry aligns with the bottom of a conduit groove 125 of the spillway conduit. Transwell height is set by the vertical location of a step shelf 123 on which the outer rim of the transwell rests.
Figure 14:
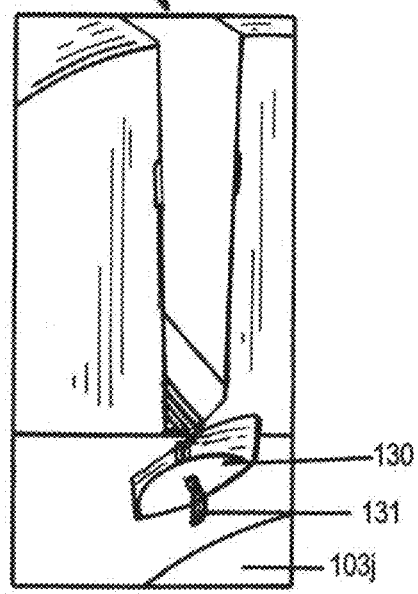
FIG. 14 is a side view of the exit geometry for a spillway 121 into a destination well 103j. The exit geometry of the spillway includes an undercut 130 in the wall of the destination well, below the edge of the spillway conduit, and a vertical groove 131 to guide along the wall of the destination well.
Figure 15:
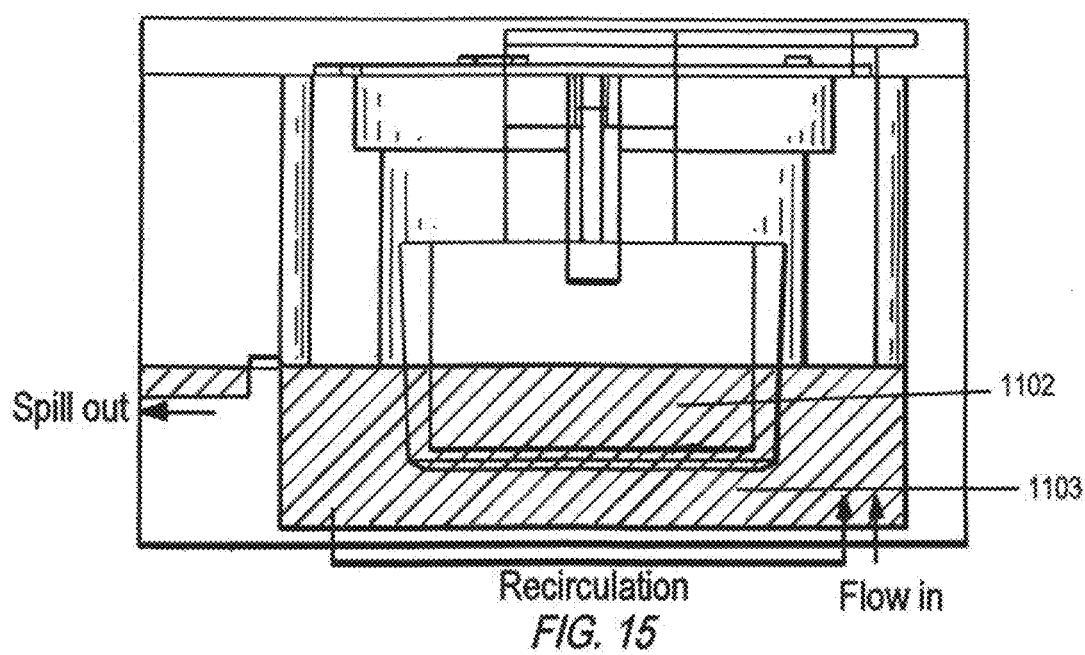
FIG. 15 is a cross-sectional side view of a perfusable scaffold in a perfused well of a device showing the apical volume 1102 in the scaffold and the basal volume 1103 in the well.

FIG. 13 shows one embodiment of the improved entry geometry for the spillway, in which a shallow and gentle entry of fluid via a radial meniscus pinning groove around the well, where the bottom of the meniscus pinning groove aligns with the bottom of a grooved fluid flow channel.

Figure 19:
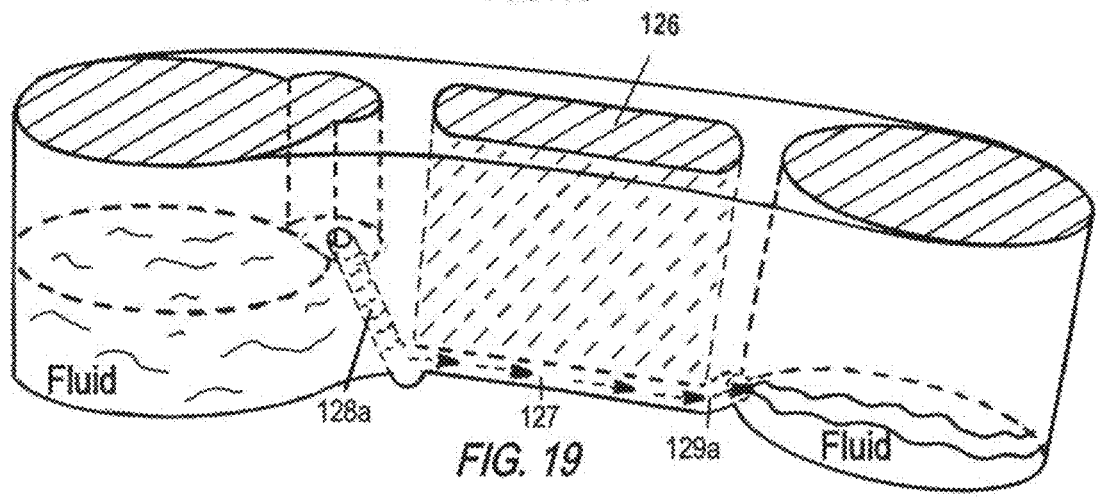
Figure 20:
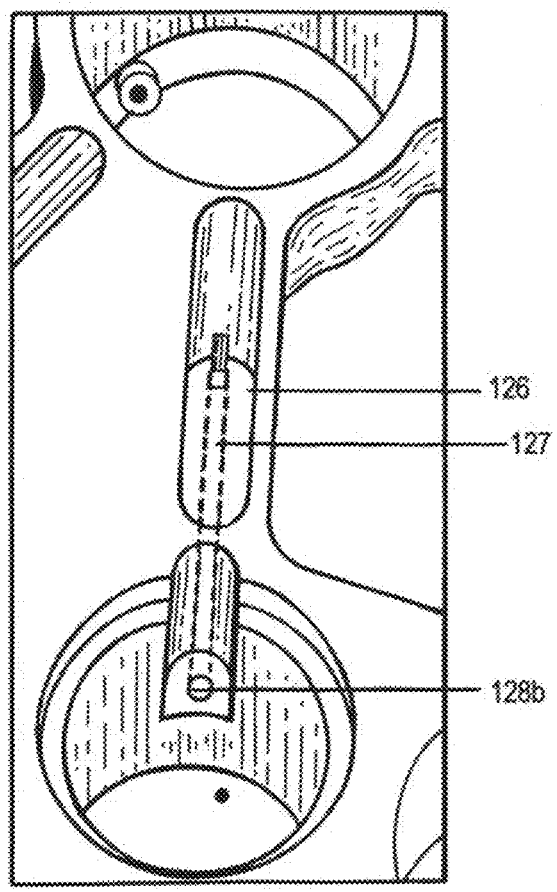
FIG. 20 is a schematic of a top view of the spillway shown in FIG. 19. The tower conduit has an opening, i.e., a hole 128b, on the surface of a step in the wall of the source well, which connects to the spillway conduit 127 in an open-fluid configuration 126.
Figure 21:
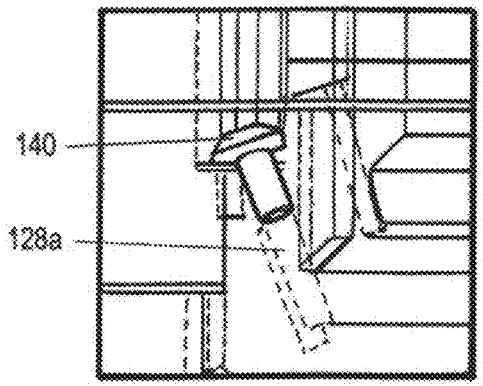
FIG. 21 FIG. is a schematic of a cross-sectional side view of the spillway shown in FIG. 19, where a screw 140 plugs the tower conduit 128a, preventing spillout flow from a source well.

FIGS. 19 and 20 show another embodiment of an improved entry geometry for an open conduit spillway in a cross-sectional side view and a top view, respectively. A slanted conduit tower 128a connects the source well to an open conduit 127, which may have a spontaneous capillary flow (SCF) groove at the bottom. The entry geometry utilizes a hole-in-the-wall design, where a hole 128b is created on a step surface to connect to the slanted conduit tower 128a. A screw seal 140 may be placed to plug the opening hole of the conduit 128a to isolate MPS interactions (FIG. 21). The screw seal generally has an O-ring next to the thread to create a good seal once plugged into the hole.

Conduit Allowing for Spontaneous Capillary Flow (SCF)

Figure 22A:
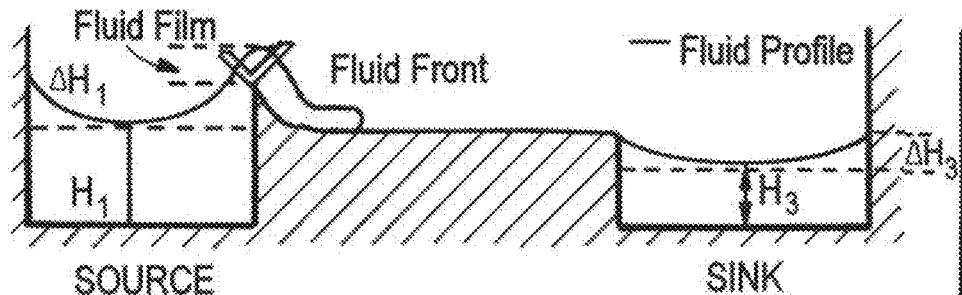
FIG. 22A, FIG. 22B, and FIG. 22C illustrate a successive time-course development of a spillway with a V-shaped entry geometry of (cross-sectional side view), from initial fluid front into the conduit (FIG. 22A), to migration of fluid front along the conduit (FIG. 22B), and fluid accumulation in conduit (FIG. 22C).
Figure 22B:
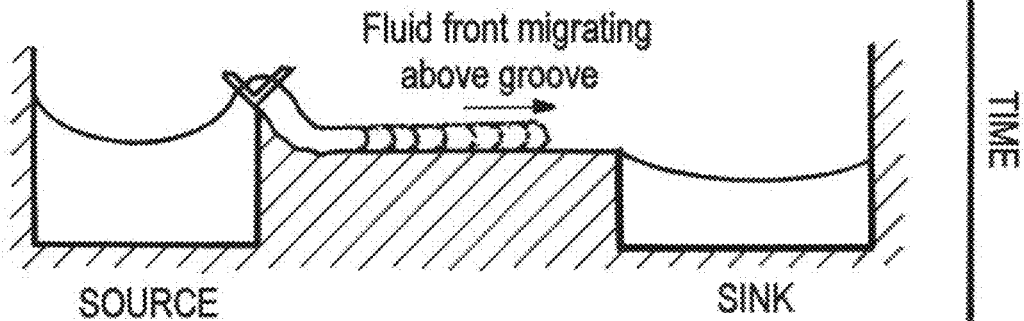
Figure 22C:
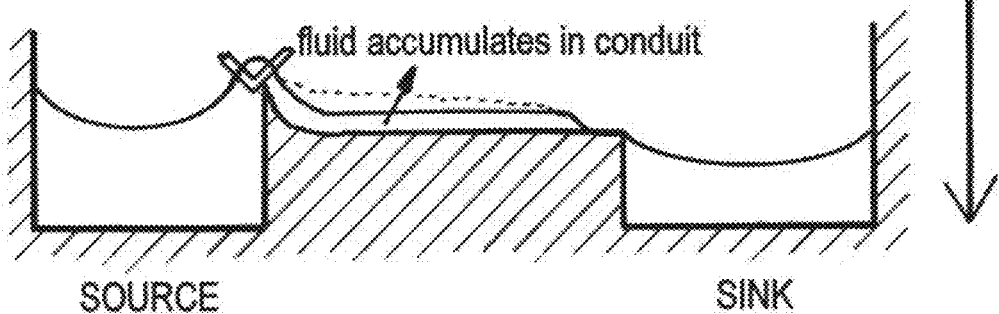

FIGS. 22A-22C illustrate a time-course development of fluid across the spillway conduit from a spillway with a V-shaped entry geometry. When the conduit has not been primed or when spillway conduit is dry due to evaporation or fluid film disruption, the front of a migrating fluid coming from the source well forms a meniscus within the wall of the conduit, which advances slowly and accumulates fluid above the groove of the conduit. This spillway conduit issue was first observed in dye testing on a 7-way alpha spillway, where the spillway was wetted by fluid front but the fluid migration along the conduit was slow and required substantial volume to wet the entire spillway.

The following represent means for improving flow by altering conduit geometry.

Geometry and Dimension to Allow Spontaneous Capillary Flow to Assure Robust Wetting in Channels.

The fluid movement efficiency along the channel was compared among a round-bottom, a V-shaped, and a rectangle-bottom open channel of a comparable small dimension. 2 µL of fluid droplet was added at one end of the open channel to measure the wetting distance without priming of the channel. A V-shaped channel was shown to exhibit a wetting distance of 103 mm; a rectangular shaped channel had a wetting distance of 44 mm, and a round-bottomed channel had a wetting distance of 7 mm. Both the V-shaped channel and the rectangle-bottom channel support Concus-Finn flow (Berthier J, et al., *AIMS Biophysics*, 1(1):31-48 (2014)). A greater wetting distance generally shows a greater wettability performance which maintains a continuous fluid flow in an open channel spillway.

Effect of Material Used to Form the Conduit

A conduit with spontaneous capillary flow (SCF) maintains a fluid film and thus fluidic communication with minimal volume requirements and without any particular priming or pumping rate. To achieve SCF, the cross-section of the conduit should satisfy the following relationship:

$$\frac{P_F}{P_W} < \cos\theta,$$

where
$P_F$=The free (in contact with air) perimeter
$P_W$=The wetted (in contact with wall) perimeter
$\theta$=The generalized Cassie angle (the average contact angle of the material).

SCF results when the energy reduction from wetting walls outweighs the energy increase from extending the free surface. Using Gibbs thermodynamic equation, the general criterion for spontaneous capillary flow in composite-wall and air systems is the generalized Cassie angle $\theta$ must be <90°. The generalized Cassie angle is the average contact angle of the material. In preferred embodiments where the fluidic plate is made with polysulphone, the contact angle for media-polysulphone-air has been measured to be 30°<$\theta_c$<113° for polysulfone with water or media. This wide range of contact angles is based on the effects of surface micro pattering and in lesser degree small differences in polysulfone hydrophobicity and thermal effects of incubation environments. To satisfy the SCF relationship, the range of perimeter ratios that allow for SCF in the embodiments described herein ranges from 0<$P_F/P_W$<0.866 (cos 30°≈0.886; negative perimeter ratios are not possible, thus not considered). This is an exemplary estimation, and it is to be understood that other implementations may utilize alternative ratios. Practically, the contact angle anywhere in a channel is reasonably assumed to be ≤80°, considering the meniscus effect and/or poorly wettable surface (which may be machined to generate a smooth finish to encourage higher wettability). Therefore in a scenario with a prominent meniscus effect, or with poorly wettable surfaces, such that the contact angle is about 80°, the perimeter ratio goes 0<$P_F/P_W$<0.18 (cos 80°≈0.174; arccosine 0.1866≈80°) in order to satisfy the SCF relationship.

Figure 23:
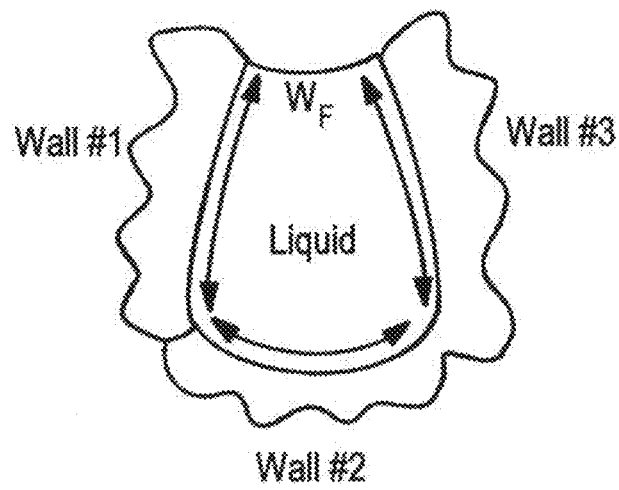
FIG. 23 is a schematic of the dimension of conduit geometry for calculation to determine spontaneous capillary flow (SCF). $W_F$ symbols the dimension of liquid-air interface.
Figure 24:
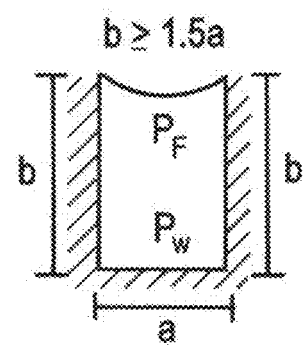
FIG. 24 is a schematic of the dimension of a rectangle conduit for calculation to determine SCF. The conduit has a depth of b and a width of a, totaling a cross-sectional conduit perimeter of Pw, whereas the liquid-air interface has a perimeter of $P_F$.

FIG. 23 and FIG. 24 provide a cross-section analysis of a channel of an arbitrary shape. Here, the perimeter of liquid exposed to air, $W_F$, would be the free perimeter, $P_F$, in the above relationship; and the sum of liquid perimeter in contact with three walls, $W_1+W_2+W_3$, would be the wetted perimeter, $P_W$, of the above relationship. FIG. 24 illustrates an exemplary rectangle shaped channel with a width of a and a height of b. To satisfy the SCF relationship, the perimeter ratio should follow:

$$\frac{P_F}{P_W} = \frac{1.5a}{(2b+a)} < \cos(80°).$$

When defining an aspect ratio, $\lambda=b/a$, therefore $b=\lambda a$, the relationship goes $$\frac{1.5a}{(2a\lambda+a)} < 0.18,$$

which can be calculated to derive a criterion for the aspect ratio to allow SCF by a poorly wettable surface and/or a channel surface with a prominent meniscus effect:

$$\lambda = \frac{b}{a} > 3.7 \approx 3.$$

Therefore, a small rectangle channel with an aspect ratio greater than 3 generally can achieve SCF.

In some embodiments considering manufacturing capabilities, the aspect ratios range is 2.5<$\lambda$<5 to support the SCF design principle.

In some embodiments, spontaneous capillary flow is achieved in a triangular horizontal channel with an aspect ratio of about 2, where the wall smoothness is such that the contact angle is about 60°. The calculation of $P_F/P_W$ for a triangular channel would be different compared to a rectangular channel, but the same principles hold.

Figure 25:
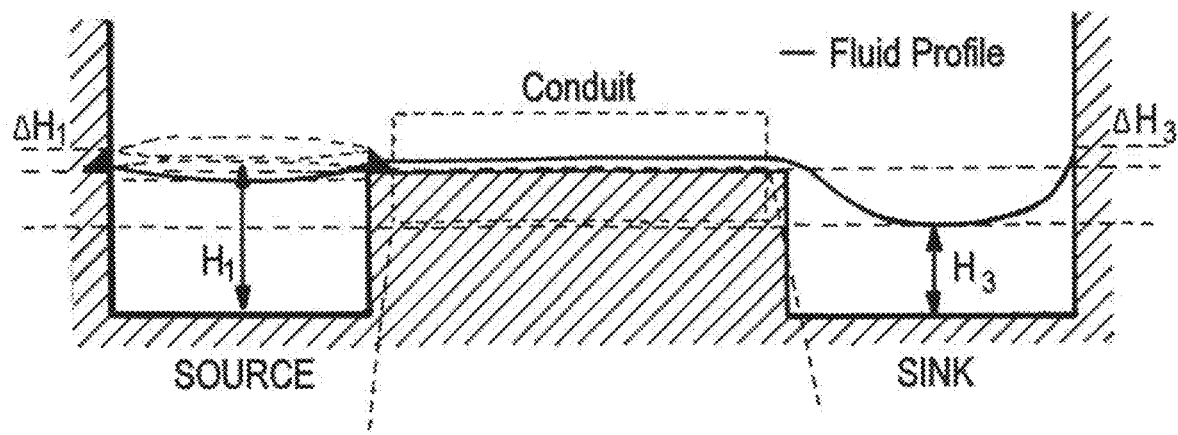
FIG. 25 is a schematic of a cross-sectional side of a spillway without a V-shaped entry geometry to support SCF.

In some embodiments, a preferred fluid path within the spillway conduit is a rectangle or V-shaped channel with an aspect ratio greater than 3, which is within microfluidic dimensions to allow for capillary flow to occur (FIG. 25 showing a continuous fluid film across the spillway). Upon an initial fluid contact with the conduit channel, a minimal volume of fluid in a channel with a geometry supporting SCF will quickly wet the entire geometry and produce a fluid film capable of efficiently transporting fluid from source to sink.

Capillary Length and Spillway Width to Assure Gravity Dependent Spilling.

According to Brakke et al., *Exp Math*, 1(2):141-165 (1992), for water in contact with acrylic (which has a similar hydrophobicity to polysulphone), the capillary length, [γ/(ρ*g)]$^{1/2}$ (where γ is the surface tension, ρ is the density of the liquid, and g is gravity acceleration), is 2.7 mm. If the distance between the two walls of a channel (i.e., width of the spillway channel) is less than the capillary length, gravity has a negligible effect. Therefore, a spillway width of 2.1 mm places the system in a regime where gravity is less dominant than capillarity.

In some embodiments where spilling is desired to be driven by gravity (e.g., in conduit tower 128a), the spillway width is greater than 3 mm.

Embodiments

FIG. 29 shows an exemplary spillway conduit geometry with a 3:1 aspect ratio rectangle-shaped groove to allow for spontaneous capillary flow. U-shaped channel above spillway is a relief cut to allow space for the drill bit collet.

In preferred embodiments, the surface tension spontaneously propagates once the liquid in the source well is leveled, and drives movement of fluid through the conduit to the target well.

Exit Geometry with Undercut Design

Figure 30A:
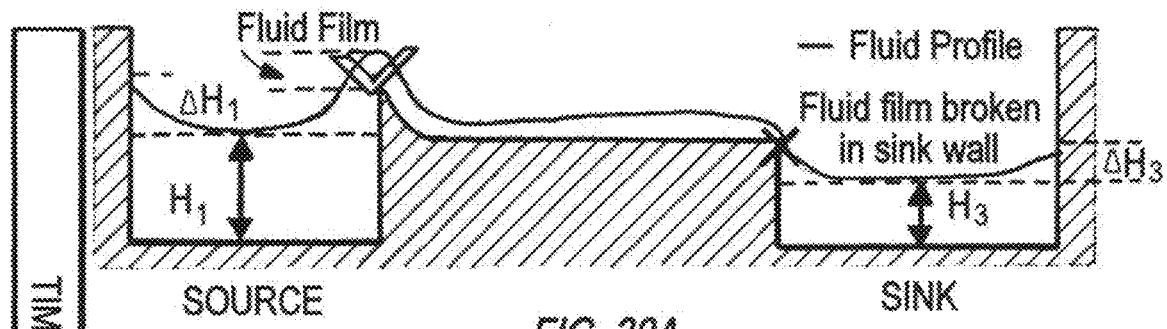
FIG. 30A, FIG. 30B, and FIG. 30C illustrate another successive time-course development of a spillway with a V-shaped entry geometry (cross-sectional side view), from initial continuous fluid film across the spillway (FIG. 30A), to fluid accumulation in the conduit (FIG. 30B), and syphon effect (FIG. 30C).
Figure 30B:
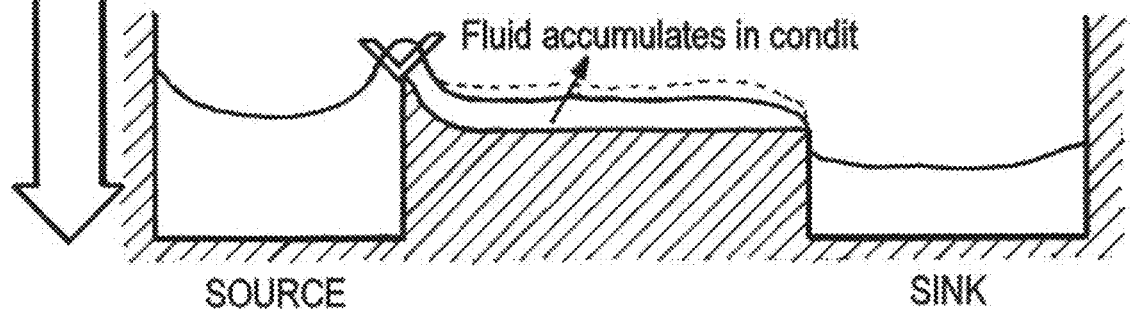
Figure 30C:
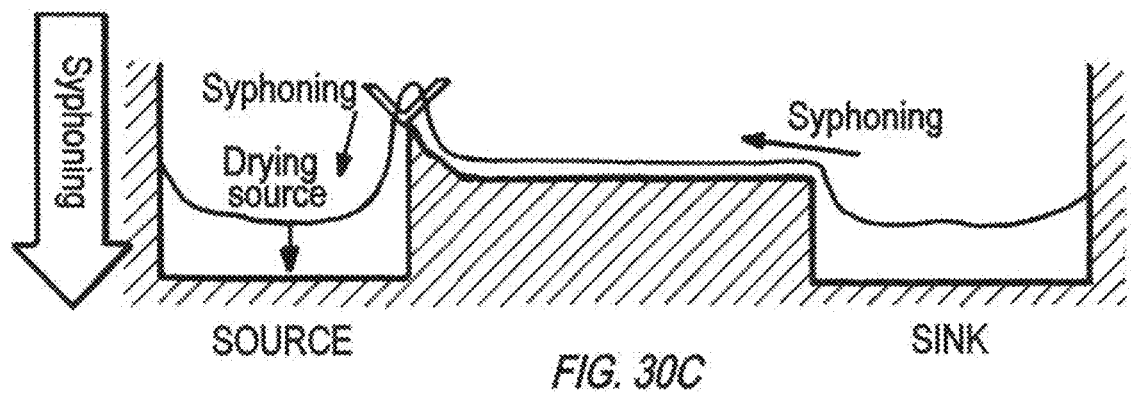

FIGS. 30A-30C illustrate spillway exit from a spillway with a V-shaped entry geometry and no additional exit geometry. When the spillway exit does not have a fluid film in the vertical wall, fluid starts accumulating in the conduit and leads to spilling bursts or even a stable meniscus at the exit geometry. This accumulation stops when the meniscus of fluid at the conduit makes contact with the meniscus at the sink, and a fluid film is reestablished. When fluid film is always present, a poor exit design may see the siphon effect even after the source fluid level is below the sink level.

This problem can be avoided or minimized using one or more of the following options:
Sharp Undercut Along a High Aspect Ratio Vertical Groove to Prevent Backward Flow.

Figure 31:
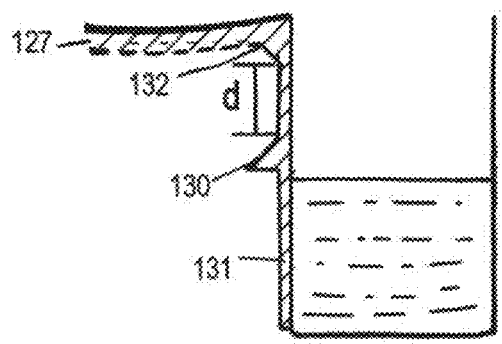
FIG. 31 is a schematic of a cross-sectional side view of a spillway exit geometry, where the spillway conduit 127 ends with a slope 132, and a distance of d below the conduit there is an undercut 130 in the wall of the destination well. A vertical groove 131 below the slope 132 and interrupted by the undercut 130 is present along the wall of the destination well.

FIG. 31 illustrates the spillway conduit 127 exits, via a slightly tapered, shallow slope (edge) 132, to connect with a vertical groove 131 along the wall of the sink/destination well. A sharp undercut 130, e.g., made with a milling machine, breaks the vertical groove 131 into two parts. The undercut is a cut into the wall of the sink well below the tapered, shallow slope 132, and has an angle from the vertical line of greater than about 30° (e.g., 30°, 35°, 40°, 45°, 50°, 55°, 60°, or more, and any continuous angle in between the exemplary numbers). In some embodiments, the distance between the undercut 130 and the spillway conduit exit, d, is between about 5 to about 10 times the width of the spillway conduit, in order to prevent the syphon effect. The vertical groove 131 is designed to exhibit spontaneous capillary flow (SCF) and to maintain a fluid film. The vertical groove runs continuously from top to bottom, except where the undercut is present. This geometry helps maintain a stable fluid film connecting the conduit and sink as long as there is forward fluid directionality. In case of reverse flow (e.g., the syphon effect), the undercut cuts the fluid film and generates a fluid meniscus that will only re-connect the fluid film when forward flow is reestablished.

In some embodiments, the spillway exit vertical groove is configured to exhibit spontaneous capillary flow (SCP) using the same design parameters described in the SCF groove in the conduit, e.g., a high aspect ratio greater than 3. The undercut and the high aspect ratio vertical groove have been tested in a series of experiments in 3×3 alpha spillways and machined polysulfone block, leading to a controlled fluid film breakage and anti-syphoning effect. A stable vertical fluid film on the improved exit geometry does not easily evaporate and allows for fluid film restoration and flow upon forward flow at spillway exit is resumed.
Rounded Slope Exit and Small-Width Groove to Break Film into Droplets.

Another improved feature is to introduce a rounded slope exit/edge at the end of the spillway conduit. When the small-width SCF groove of the spillway conduit "meets" an enlarged, round-curved area (FIG. 32), the stable liquid film in the small-width SCF groove (due to surface tension) becomes unstable at the enlarged round curved exit area, which is effectively broken into droplets and would fall ("sheds") into the sink well. This way, the source well becomes independent from the sink well, and unidirectionality of fluid flow is achieved.

In some embodiments, the entry geometry to the conduit from the source well has no slope, i.e., it drops from a sharp edge, while the exit geometry from the conduit encounters an enlarged, curved area, before liquid drops into the sink well.
Alternative Upward Exit from the Conduit In some embodiments where the SCF channel is below the desired liquid level in the sink well, an upward exit conduit with an exit hole is utilized, as shown by element 129a of FIG. 19.

Embodiments

FIG. 31 illustrates the spillway exit with a undercut beneath the exit, and vertical groove for anti-siphon effect.

Wall-bound drops that are pinned on an edge of a planar wall are generally referred to as wall-edge bound drops. Wall-Edge bound drops are typically found in nature as dew hanging from the leaves of plants until a sizable volume is reached and the drop falls. When drops are pinned on a pointed wall edge, they are referred to as wall-edge-vertex-bound drops. Wall-edge-vertex-bound drop simulations show liquid interfaces in contact with highly wetting solid walls (forming a spillway exit) tend to drip as the angle decreases. This is because the energy decrease from wetting the walls is greater than the energy of the liquid-air interface, such that the contact area wants to expand indefinitely in corners with smaller angles where thin fluid filaments form. The creation of a thin fluid filament is relevant and desirable in situations where accurate control of fluid leveling and flow is needed for open-channel fluidic systems, as the meta-stability of these filaments can provide means to allow or stop fluid transport.

(3) Recirculation

Passive self-leveling may contribute to return of flow as described in detail above.

Typically, recirculation is used to ensure that within a well, the concentrations are well distributed and uniform. Thus, recirculation flow-rates are typically higher than organ to organ flowrates.

Active recirculation, driven by within-well pumping, may increase oxygenation of the media. For example, recirculation may take place within each of lung, endometrium, gut, heart, CNS, liver, pancreas, and Mixer in a 7-way MPS platform. To reduce complexity in some embodiments, the recirculation within each of lung, endometrium, and gut may share one pump control for an identical recirculation flow rate; the recirculation within each of heart, CNS, and pancreas may share another pump control for an identical recirculation flow rate; and the recirculation within Mixer and within liver may share yet another pump control for an identical recirculation flow rate.

(4) Features to Encourage Oxygenation

Adequate perfusion rates to "meso-scale" tissues, commonly containing hundreds of thousands to many millions of cells, is difficult and critical to cell viability. Based on the oxygen consumption rate of liver, which has a high oxygen requirement, using cell culture medium as the circulating fluid, a flow rate between about 6 and 10 µL per second is needed per million of cells (Powers M J, et al., *Biotechnol Bioeng* 78, 257-69 (2002); Domansky K, et al., *Lab on a Chip* 10, 51-58 (2010); Ebrahimkhani M R, et al., *Advanced Drug Delivery Reviews* April, 132-57 (2014)). Because gas exchange can occur at the air-liquid interface in the open fluidic system in the disclosed apparatus, the platform material itself, though optional, does not need to be oxygen permeable.

Oxygenation Tail

A tail in addition to the main well for cell cultures is preferably designed for organs such as liver that higher levels of oxygenation for survival. The oxygenation tail has features supporting better diffusion and mixing of oxygen into the media such as shallow walls, faster recirculation, and independent inflow and outflow lines.

Exemplary layouts of the oxygenation tail includes a guiding groove tail (FIG. 33), a tail that is vertically rounded (e.g., and deepening), a flat tail with pinning columns, and a flat tail with meniscus pinning groove tail.

The tail preferably includes a slanted surface such that the depth of liquid can be as thin as 5 mm, 4 mm, 3 mm, 2 mm, or 1 mm, for sufficient aeration/oxygenation. In preferred embodiments, the apparatus supports cell culture survival for up to a month, two months, or longer.

In addition to the surface roughness and geometry of patterns on the tail surface, tortuosity of the tail as well as the width of the tail may be modified to enhance oxygenation. For example, zig-zag shaped, tortuous tails provide a means to enhance oxygenation requiring a reduced liquid volume for the liver module. Each turning loop or point is where meniscus can pin to. FIG. 34 illustrates a zig-zag tail layout for the liver module. A total tail length of about 225 mm may support a total tail volume of about 80 µL, for enhanced passive oxygenation, i.e., increasing the surface area of liquid exposed to air. FIG. 35 illustrates a phase-guiding geometry that is repeatedly present along the oxygenation tail. This tail has alternating maximum width and minimum width, $W_1$ and $W_2$, respectively ($W_1 > W_2$), in a repeated manner throughout the zigzag tail. Generally, within each segment of the tail between two U-shaped loops, there are two, three, four, or more repeats of the alternating maximum and minimum width. The alternated widths each has its own length, e.g., every maximum width $W_1$ has a length of $L_1$, and every minimum width $W_2$ has a length of $L_2$. Generally, $L_1$ is greater than $L_2$ to accommodate more volume. The phase guiding feature is attributable to the angled increase of the width. As shown in FIG. 35, the angle, α, represents the increase of tail width relative to the forward direction of fluid flow in the tail. The angled increase of tail width, i.e., the narrowing of tail width in the direction of the forward fluid flow, provides for better guidance for fluid directionality. $W_1$ may be in the range between 0.1 mm and 10 mm, for example between about 0.5 mm and about 1 mm. $W_2$ may be in the range between 0.05 mm and 5 mm, for example between about 0.3 mm and 0.5 mm. $L_1$ may be in the range between 0.5 mm and 10 mm. $L_2$ may be in the range between 0.1 mm and 10 mm. The angle, α, may be in the range of between 90° and 180°. In one embodiments, $W_1$ is 0.8 mm, $W_2$ is 0.45 mm, $L_1$ is 1 mm, $L_2$ is 0.5 mm, and α is 150°. The depth of the zig-zag oxygenation tail may be a fixed depth or a gradually varying depth in the range between about 0.05 mm and 5 cm, for example between about 0.1 mm and about 10 mm. In one embodiment, the depth of the tail is fixed at 0.5 mm.

Active Oxygenation Pumping Systems

Another means to enhance oxygenation is to utilize active oxygenation pumping system both ways between the liver well and the tail.

In some embodiments, the liver culturing well has within itself a recirculation pumping system, such that it has bottom-to-top flow of oxygenated media. The oxygenation tail, generally containing liquid of a shallow depth, is recirculated within itself, such that the required oxygen concentration is reached in steady state. Active pumping allows the media from the well with scaffold (generally low on oxygen due to metabolic consumption) to be pumped to the oxygen-rich tail portion. The oxygenated media from the tail is then pumped back to the well.

(5) Removable Insert

Removable Scaffold Integrable for Perfusion

Removable scaffolds may be used for MPS of choice, e.g., liver and pancreas, allowing off-platform seeding, manipulation, and assaying of the perfused tissues. Previous scaffolds by others are difficult to remove from the platform without causing damage or contamination. In some embodiments, the removable scaffolds hold the filters and retaining rings that are a standard size, e.g., compatible with the disclosed platform and/or commercially available LIVER-CHIP®.

Scaffolds are configured to allow gentle insertion and removal via rotation and sliding along a sloped guide ramp. Some MPS compartments designed for use with these scaffolds include a sloped ramp to guide the insertion and/or removal of the scaffold. A radial seal with the platform is established with a low-binding o-ring (e.g., VITON® o-ring), allowing perfusion of the entire removable device.

Figure 36:
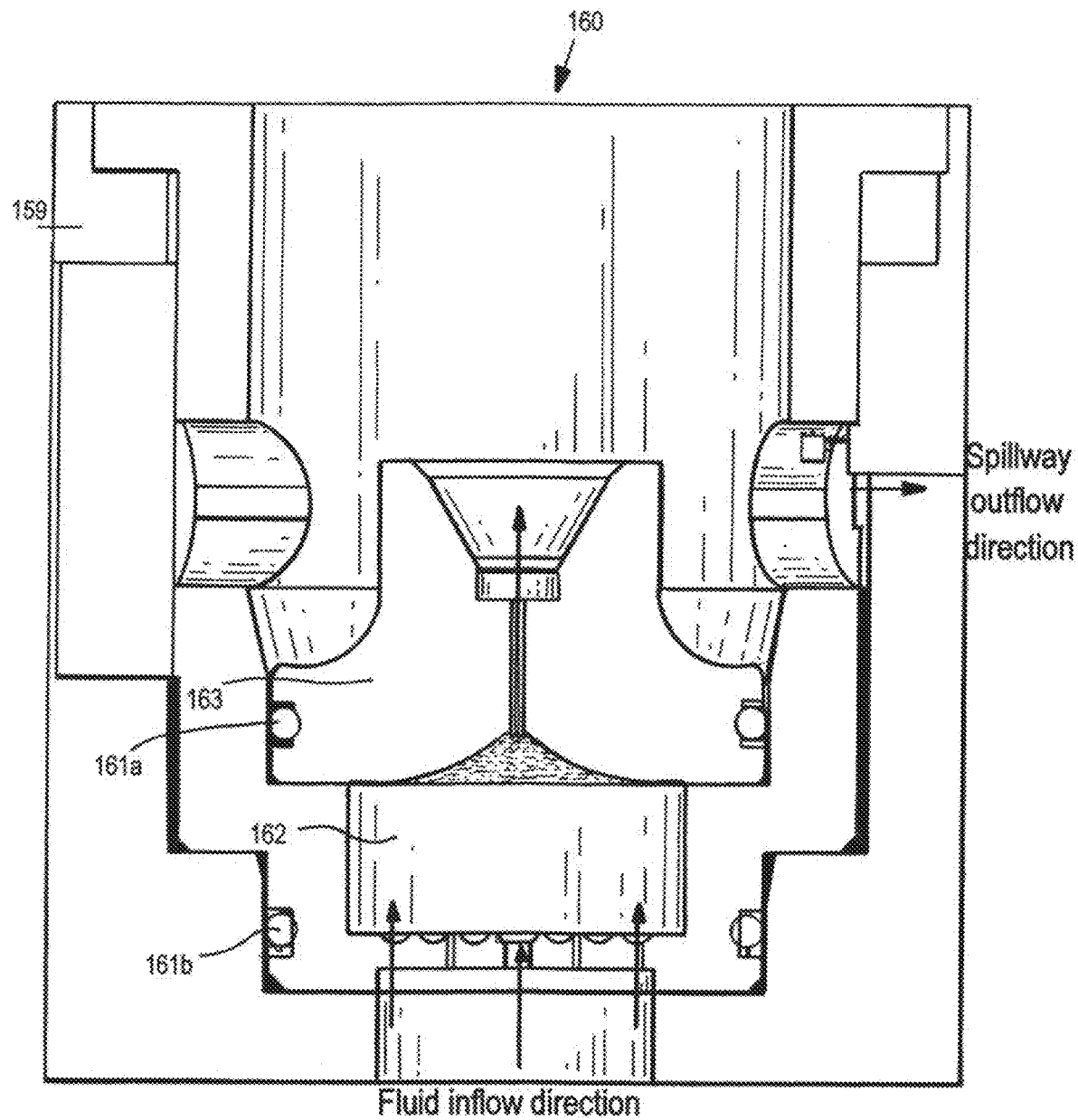
FIG. 36 is a schematic of the cross-sectional side view of a removable, perfused scaffold 160 inserted into a well on platform, which shows a ramp area 159 for securing (e.g., turn by screw thread) the scaffold, radial seals 161a and 161b (e.g., O-rings), a cell culture region 162 in the scaffold, and a fluid aggregation lid 163 useful for non-contact oxygen sensing.

FIG. 36 illustrates an exemplary modular, removable perfusion scaffold that allows perfused cell constructs to be gently removed from the surrounding platform. The device includes a cup-like shell with radial o-ring seals 161a/161b and a flow-diffusing support structure at its base. Cells with or without biomaterials can grow on top of this support 162. On the sides of the device in the upper body or the extension arm of the scaffold, two holes allow for manipulation with sterile tweezers and small flanges help to guide it along a ramped thread. The ramp 159 allows gentle insertion and removal via rotation, rather than vertical force. Torqueing the scaffold into place minimizes the fluid pressure experienced by the cells during insertion and removal.

Portability permits a number of functions that improve the usability of a multi-well bioreactor. For example, constructs can be cultured in isolation, in unique cell media, and then selected for health and viability before they are joined together for a human-on-a-chip experiment. A removable scaffold also allows complete isolation of one cell population from the multi-well bioreactor, allowing external assays of cell health and metabolism to be performed without tainting the shared media with potentially harmful reagents.

The scaffold supports fluid inflow from below, i.e., the bottom surface of the well, and spillway outflow to other wells on the platform.

In some embodiment, a fluid aggregation device 163 is optionally added on the removable, perfused scaffold to collect flow into a narrow orifice. Fluid is mixed, and aggregated fluid is collected past a fixed location. At the outflow location, the oxygen tension or other fluid properties can be queried by a small probe resting inside the top of the device. This way, sensors for average $O_2$ measurement do not require dipping into the media or a part of the culture.

In some embodiments, a thin scaffold with a thin bottom/wall thickness between about 0.05 mm and about 5 mm, preferably between about 0.1 mm and about 1 mm, or about 0.25 mm, situated on a membrane, is utilized to seed liver-associated cells for enhanced oxygenation, where the scaffold is perforated with an array of channels (e.g., ~0.3 mm diameter) and is maintained in a re-circulating flow multi-well plate bioreactor. Liver cells seeded into the scaffold form 3D tissue-like structures, which are perfused at flow rates sufficient to create a physiological oxygen tension drop across the scaffold without excessive shear (Yates C, et al., *Adv. Cancer Res.* 97, 225-246 (2007)) and which can be maintained in a functional state for weeks in serum-free culture medium.

TRANSWELL®

The apparatus can contain wells that are compatible to hold multiple insert vehicles for cell culture, such as commercially available TRANSWELL® inserts or custom biomaterial scaffolds to support cells or organoids.

(6) Moat to Reduce Evaporation

Additionally or alternatively, some embodiments of the apparatus include a humidity moat (element 104 in FIG. 5) to increase local humidity and reduce evaporation from the cell culture media. The moat may be connected to external fluid source or fluid pumped in via build-in fluid channels in the fluidic plate. Monitoring and pumping of fluid into the moat may be needed to compensate for loss of liquid due to evaporation, which is generally dependent on flow variations in the organ culture wells. The in-platform moats or micro evaporation chambers can be placed in any region of the fluidic plate to increase the moat area to minimize evaporation from the wells, allowing for the creation of a humid microenvironment around the microphysiological well zones. Local heating in the moats may also be used so most of the evaporation to maintain the high relative humidity above the platforms comes from the moats.

(7) Means for Addition or Withdrawal of Agent/Specimen

The apparatus may be connected to or used with one or more auto-sampling devices. For example, the auto-sampling devices may be fluidically connected to a low wetting sample collection tube.

(8) Pneumatic Actuation

On-board pumping saves dramatically on space and cost compared to commercial syringe or peristaltic pumps, is more scalable, and allows closed-loop operation with very low dead volumes. Dynamic control of flow rates and directionality enables precise modulation of concentration profiles, allowing experimental operation to be scaled to match clinical/physiological distributions. Flow partitioning is controlled by imposing specific pumping frequency in the individual microphysiological systems, leading to specific flow-rates and; therefore, "partitioning" of flow.

Pneumatic Manifold/Plate

Figure 37A:
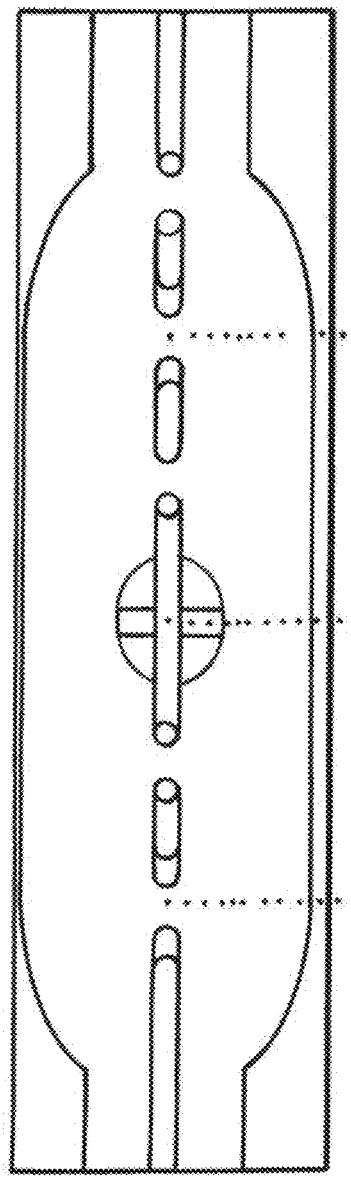
FIG. 37A is a schematic showing the top view of a three-chamber unit on the surface of a pneumatic plate.
Figure 37B:
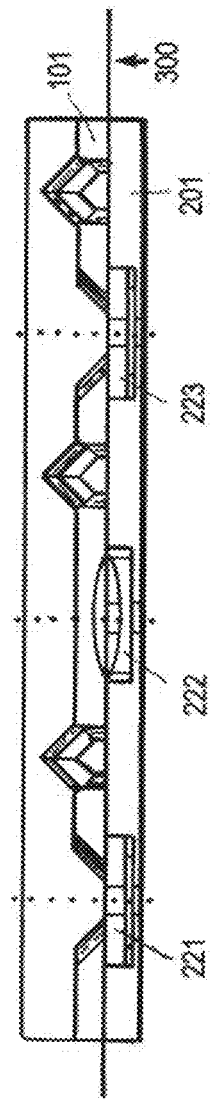
FIG. 37B is a schematic showing the side view of a three-chamber unit corresponding to FIG. 37A. A barrier membrane 300 separates a fluidic plate (containing a fluid path 101) and a pneumatic plate. The pneumatic plate has protruding features 201 on which holes create chamber spaces that are connected to internal channels (air actuation lines) of the pneumatic plate (not shown in this Figure). Here the chamber 221 serves as a valve, chamber 222 as a pump, and chamber 223 as another valve.

Pneumatically controlled fluid flow in the fluidic plate is generally achieved via a three-chamber unit e.g., 220*a*, 220*b*, or 220*c* of FIG. 4. FIGS. 37A and 37B illustrate the details of an exemplary three-chamber unit containing a pump in the center and two valves, each on a side. When actuated sequentially, this valve arrangement can provide directionality in flow by preventing backflow while allowing for forward fluid displacement. The well-characterized, reliable valve-pump-valve units provide fixed strokes of fluid, which generate deterministic fluid flow. This supports a broad, dynamic pumping range between about 1 µL/day and about 10 mL/minute. In some embodiments, one or more or all of the pumping channels have reversible flow, supporting priming, sampling, and/or media/drug delivery configurations.

Generally, the pneumatic layer uses a pass-through design, where air-conducting actuation lines with air inlets and air outlets 210*a* and 210*b* (entry and exit being relative to the orientation of the plate) pass horizontally through the pneumatic plate, preferably in straight paths. Straight paths of air-conducting actuation lines occupy less of the total platform footprint, and they support a faster pneumatic response (e.g., fast pressure change due to a low volume). Symmetrical air inlets and air outlets allow platforms to be daisy chained to run simultaneously, connecting the outlets of one plate directly to the next with short lengths of tubing.

The pneumatic manifold generally employs a single bonded layer of material that allows for the creation of internal pneumatic channels. The pneumatic actuator membrane is generally a single layer polymeric material, e.g., polyurethane, that may be pressed between the pneumatic plate and the fluidic plate, or attached to one of the plates. The fluidic side in this case contains fluidic channels with micron range resolution geometries that allow for direction and evacuation of fluid. Higher resolution of the fluidic channel generally leads to a slower speed of fluid movement, but it may allow for smaller death volumes.

4-Lane Dual-Channel Pump

In addition to the valve-pump-valve (V-P-V) pneumatic actuation configuration, a pump-pump-pump (P-P-P) configuration can be added to allow for a peristaltic movement of fluid.

Figure 38:
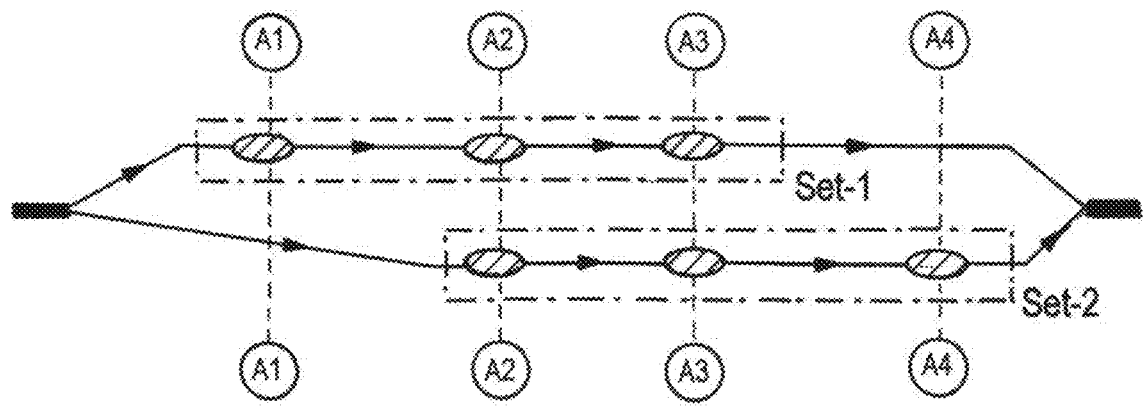
FIG. 38 is a schematic of a top view of split fluid flow on top of dual three-chamber units that are controlled by four air actuation lines.

Two or three sets of the three-chamber units may share one or two air-conducting actuation lines, as shown in FIG. 38. When a fluidic channel (of the fluidic plate) splits into two channels that are pneumatically regulated by both a set of V-P-V pump and a set of P-P-P pump, which are placed one actuation line off and are 180° out-of-phase, the overall fluid combined from these two pulsating strokes has a smooth volume profile. Four actuation lines for these two sets of pumps accounts for four degrees of freedom, which requires only one more pneumatic line than the V-P-V configuration.

One or more x-chamber units (x>=3) may be placed with one or more air-conducting actuation lines off, in a similar principle to that shown in FIG. 38, to have a customized smoothness of flow volume.

Modular Pumping

Independent pumping allows for a different, e.g., higher, flow rate than that offered by the shared pumps. The incorporation of the fluid wells into the plate can reduce or eliminate the need for tubing, but the pump designs can be amenable to driving external flows as well. Connections, such as ferrule connections, can be used to interface the built-in pumps with external tubing, allowing a pumping manifold to drive a large number of flows simultaneously and in a compact package.

Pump Block for Single-Pass or Recirculation Perfusion

The top, or fluidic layer, contains the MPS compartments and the pumps and channels that interconnect them. Below the fluidic layer, a thin membrane such as a polyurethane membrane provides a sealing surface for the channels and functions as the actuation layer for the pumps. The bottom layer is a manifold (e.g., an acrylic manifold) that provides pneumatic actuation of the pumps by routing compressed air to the base of each pump chamber. When vacuum is applied, the membrane is pulled down toward the pneumatic layer, filling the pump with fluid. Conversely, when pressure is applied, the membrane is forced up into the fluidic plate, driving fluid out of the pump. By actuating three chambers in series, a fixed displacement peristaltic pump is formed, allowing fluid to be moved linearly and against head pressure without backflow (Domansky K, et al. *Lab Chip* 10(1):51-58 (2010); Walker I, et al. *Journal of Micromechanics and Microengineering* 17(5):891 (2007)).

Geometry to Reduce Membrane Stress

Different geometries of the pump other than one shown in FIG. 37B may be used. An alternative form includes designs where the horizontal channels connecting the pump to the valves has been removed, leaving only the V-shaped connection that directly links two adjacent chambers. The rational behind these V-geometries is that these features pneumatically isolate one chamber from the other when the membrane deflects such that when one valve is actuated, its adjacent valve doesn't respond. Alternative configurations of pump geometry may reduce membrane stress and increase longevity of the actuation system and its consistency.

In some embodiments, further modifications to pump cavity geometries are created to render one concave contact and one convex contact between the membrane and the different V-shaped bridges, such that to prevent membrane deformation and breakage.

Validation of Pumping

Parity between the intended and actual flow rates enables well-mixing and intended molecular biodistribution among MPSs on a platform. Validation of the hardware may include direct measurements of pump rates using a capillary flow measurement tool. In some embodiments, the tool is interfaced with the outlets in each MPS compartment such that flow may be measured as a function of time required to fill a fixed length of tubing. Deviations of flow rates from one fluidic plate to another may be attributable to slight machining differences in the depth of the pump chamber. Nevertheless, software calibration factors calculated from the measurements may be entered to correct the pumping rates to within about ±5%, ±4%, ±3%, ±2%, or ±1% of the target flow rates to adjust individual pumps. Generally, a small margin of error still allows for reliable and deterministic operation, and accurate data interpretation.

(9) Means for Non-Contact Fluid Level Sensing

Capacitive Sensing with a Three-Electrode Design

Figure 39:
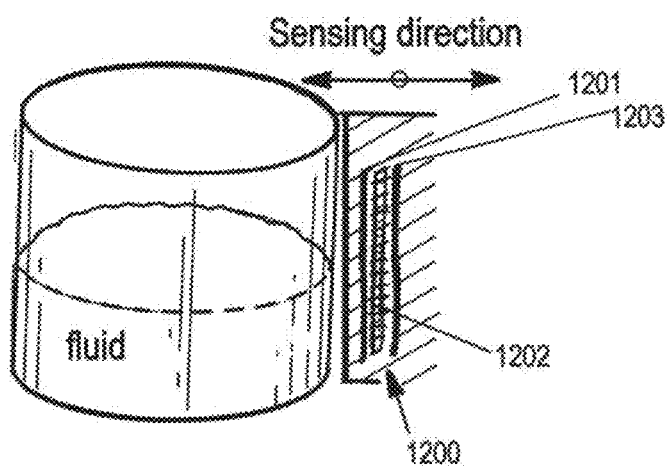
FIG. 39 is a cross-sectional side view schematic of an in-wall fluid level sensing capacitor 1200, including front electrodes 1201 and back electrodes 1203 that are on opposing sides of a board 1202 (e.g., polychlorinated biphenyl (PCB) board).
Figure 40:
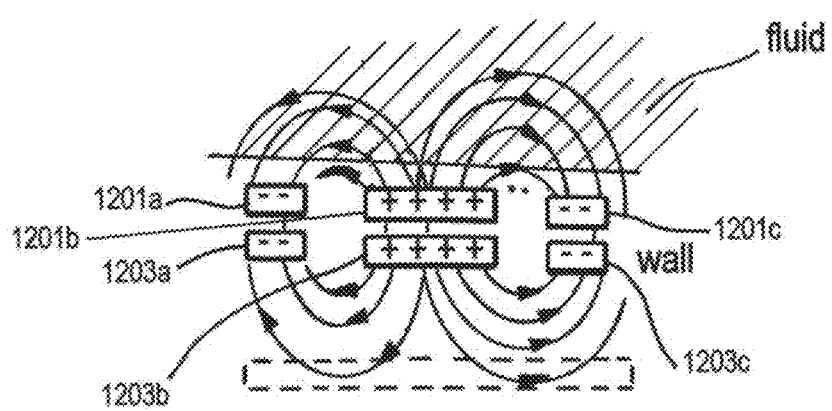
FIG. 40 is a top view schematic of the electrodes of the in-wall fluid level capacitive sensor shown in FIG. 39, showing a front sensing electrode 1201b with a front reference electrode 1201a coplanar on one side and another front reference electrode 1201c coplanar on the other side, as well as a back sensing electrode 1203b with a back reference electrode 1203a coplanar on one side and another back reference electrode 1203c coplanar on the other side.

The fluid level in a MPS well may be measured in a non-contacting manner using capacitance sensing. Electric charges go through plastic, such that probe can be placed next to the well but not in contact with the media/culture of the well to avoid possible contamination. A capacitive sensing probe may be embedded in the wall material of wells (e.g., made from plastic). The circuit senses capacitance through the wall without fluid contact. Capacitive sensing electrodes sit behind the layer of plastic isolated from fluid. As shown in FIG. 39, front electrodes 1201 measure capacitance close to the fluid, while back electrodes 1203 measure capacitance of plastic only (as reference). Front electrodes and back electrodes may be built on two sides of, therefore backed by, a polychlorinated biphenyl (PCB) board 1202 or a flex backing. The front electrodes have a sensing electrode in the middle and two reference electrodes, one on each side, which are coplanar to the central sensing electrode (FIG. 40). This organization of reference electrodes and the sensing electrodes allows for good matching. Mirror opposing electrodes provide self-guarding.

Previous designs places one negative (reference electrode) conductive plate side-by-side and coplanar to the one positive (sensing electrode) in an attempt to measure liquid level from within the well wall in a non-contact manner. This causes the reference capacitor, Cref, to be in the wrong place and results in inaccurate measurement of fluid level.

The apparatus utilizes an improved design containing three electrodes of symmetry, i.e., two reference electrodes coplanar to and symmetrical about a central sensing electrode, coupled with a mirror set of electrodes on the back side of a PCB board. This results in Cref in the right place for self-guarding and better matching.

Optical Measurement

Light illumination of the fluid surface may indicate the depth of liquid in a well.

Pressure Sensing

In some implementations it may be advantageous to use a pressure sensor to determine the height of fluid in a well. This is possible given the well-known relationship between pressure and height given by $P=\rho*g*h$, where P is pressure, rho is fluid density, g is the acceleration of gravity, and h is the fluid height. A pressure sensor of known types in the art may be incorporated in fluidic connection to a well such that the pressure sensor is measuring pressure in the well at a known reference height.

Feedback Control of Pumps for Volumes and Flow Rates

Measurements of a fluid level in a well can be transmitted to the control unit that regulates the flow rates of liquid pumped into one or more MPS wells. With a capacitive sensing measurement of the fluid height in a well, the volume of liquid in that well can be calculated with a known surface are of the well. A real-time measurement of a fluid level therefore provides information of the volume flow rate (i.e., difference in the fluid heights over the period of time). The feedback facilitates control of a set-point volume and pumping flow rate to MPS wells.

(10) Means for Temperature and Pressure Sensing and Control

Temperature is controlled by placing these platforms in an incubator, which maintains the global temperature within to 37±0.5 deg. Pressure sensing can be done with any of the static pressure sensing sensor types known in the art and give an indication of fluid height in the wells. Incorporating sensors to measure the well fluid height, using capacitive fluid level sensors or pressure sensors, in a feedback loop can help in actively controlling the well fluid volumes.

(11) Assembly of Integrated Components

Securing the Pneumatic Side with the Fluid Side

In some embodiments, bolting through alignment pins may be used as the means to assemble the pneumatic side with the fluid side of the bioreactor. Insufficient sealing may result in fluid leakage.

Clamping may be used as an alternative means for securing the pneumatic side with the fluid side of the bioreactor. Mechanical, as well as magnetic, clamps may be used to clamp the fluidic plate, the actuation membrane, and the pneumatic plate together.

Whippletree pressure distribution mechanism may be utilized in distributing pressure across different air actuation lines or across platforms.

Daisy Chain of Multiple Bioreactors

In some embodiments, two or more multi-organ MPS platforms are chained one after another at the air inlets and outlets. With the pass-through, straight-path design of air-conducting actuation lines across the pneumatic plate, two or more platforms share pneumatics and a same set of controller. No additional hardware is needed to scale up the number of platforms in a group. With symmetrical air inlets and outlets on each bioreactor, daisy chaining is easy to set up and disassemble. This feature saves time, cost, and space for operating several bioreactors/MPS platforms at a same time.

Multilayered Organ-On-Chip Fluidic and Pneumatic Plates

Figure 41:
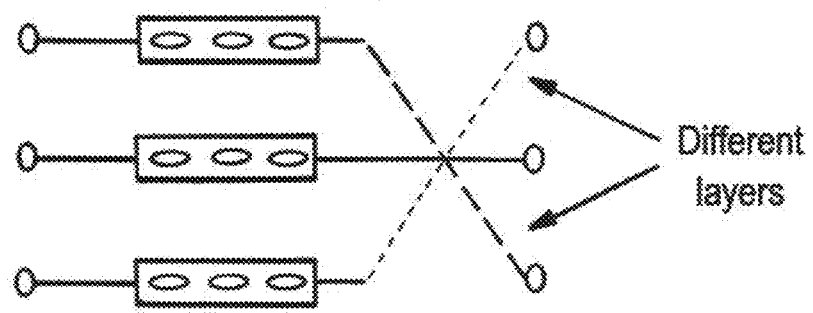
FIG. 41 is a schematic of three layers of pneumatic lines for stacked platform.

FIG. 41 illustrates a criss-cross design of pumping system for multilayer stacking configurations of platforms.

Multilayered organ-on-chip plates may be assembled via internal channels, made by either bonding of independent layers or 3D printing. The connections between pumps can overlap for this higher density of fluidic plates. It is also compatible with different pumping and valving configurations (e.g., such as those described in pneumatic actuation). The ability to have multilayered plates enables internal channels, which may replace the V-cuts in the valves, which reduces the pressure spike due to valve operation and improves the performance for more deterministic pumping profiles.

Multilayered plates may have several benefits over single-layer clamped plates. Higher density of pumps and channels generally allows for better sealing, reduction of overall device footprint, no cleaning needed for disposable manifolds, and an increased capability to multiplex controls with crossing channels. It is also easier to divert channels around areas where imaging is desired, or where sensors need to be inserted for measurement, in a multilayer plate configuration that the single-layer chain configuration. It provides more freedom in the layout of culture wells and the capability to incorporate new pump configurations.

External Connection

The multi-layer bioreactor apparatus may be connected to a microcontroller and an external pneumatic solenoid manifold to provide a source of pumping from outside. For incubation of the bioreactor apparatus, a pneumatic solenoid manifold is connected that controls 36 or a customized number of channels of tubing running through the back of the incubator to intermediary connectors. Inside the incubator, tubing is attached to the platform/bioreactor through valved breakaway couplings to allow easy removal from the incubator for media changes and sampling. The connectors and software architecture allow the setup to be compatible with the 2-way, 3-way, 4-way, 5-way, 6-way, 7-way, or a customizable number of multi-organ platforms, as well as many future platform variants, with minimal modification to the software configuration. Pump flow rates and calibration factors are set through a graphical user interface on a laptop, and can be sent to a customized microcontroller (e.g., National Instruments myRIO-1900) over USB or WiFi. Both manual and pre-programmed control of pump rates are available depending on the experimental needs, and the microcontroller can run independently of the laptop.

In some embodiments, a multi-organ MPS platform is connected to a local reservoir between controller and pump. In other embodiments, it is connected to external microfluidic device for import of external supply and export of waste.

Computerized Operation

Control software is configured to be instantiated/installed on or with an appropriate device, such a microcontroller (e.g., a NATIONAL INSTRUMENTS MYRIO microcontroller) to allow continuous operation of a physiomimetic platform without the need for a dedicated laptop or desktop computer, although it is to be understood that some embodiments may utilize such a dedicated computer. The software operates the pneumatic pumps contained in the platform for the purposes of: fluid replenishment and mixing (which provides nutrients and oxygen to the cells); introduction of fresh media from an internal or external source (feeding); removal of media to an internal or external collection vessel (sampling and waste collection); and/or dosing of test compounds, growth factors, drugs, or other chemicals/proteins of experimental interest (dosing).

By providing a graphical user interface for the control of mixing, feeding, sampling, and dosing, this software facilitates the execution of complex experiments meant to replicate physiological interaction of compartmentalized organs.

The components and/or software also provide real-time feedback from pressure and vacuum sensors integrated into the hardware, which can contain the microcontroller, pneumatic solenoids, pressure sensors, and/or power distribution electronics. In some embodiments, there is also the capability to add an alarm for drift of pressure and vacuum out of acceptable ranges, and long-term data logging of these values can be implemented.

In some embodiments, individual and global correction factors are incorporated in the software to allow correction for manufacturing variability in pumps on the platform. For example, two pumps operating at the same frequency (e.g., 2 Hz) will not always pump at exactly the same rate if one is machined slightly deeper than the other. By determining a correction factor (iteratively and/or experimentally), the rate of the pump can be tuned to be very exact, where pumps were measured, calibrated, and re-measured to target 1 µL/s at 2 Hz. The software correction factors improve the performance of the pumps and minimize manufacturing variations across platforms.

In some embodiments, the microcontroller is WiFi compatible. The software can be configured with a web UI and backend (e.g., LabView backend) to control the pumps. This allows the user to access the control panel of the software in a web browser without having to connect physically to the microcontroller, allowing remote control and monitoring of experiments from across the room or across the world.

An exemplary information flow from user to output includes the following. A user accesses webUI over the local network or via VPN remotely. Control changes are passed from the WebUI to the backend, which adjusts the timing of the solenoid actuation to meet the desired flow rates (accounting for individual and global pump calibration factors). The microcontroller then outputs a 3V digital on/off signal to a control board that amplifies that signal to a 12V analog actuation of the desired solenoids.

In some embodiments, there is a debug mode that allows manual operation of every single solenoid, for the purposes of finding malfunctioning solenoids or manually opening/closing individual pumps and valves of the platform.

Depending on different platform hardware design, the software is implemented in a number of different ways, including: 4-way platform software—controls pumping and calibration factors, displays pressure/vacuum data for 4 organ platform; 7-way platform software—controls pumping and calibration factors, displays pressure/vacuum data for 7 organ platform, a program mode to define automated flow rate changes over time, and automated feeding and sampling controls from external ports on the platform; 3×GL platform software—controls pumping and calibration factors, displays pressure/vacuum data for 3 organ platform, includes a program mode to define automated flow rate changes over time, controls automated feeding and drug dosing (controlled volumes) to organs.

Also, a computer may have one or more input and output devices, including one or more displays as disclosed herein. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In some embodiments, the disclosed software to operate the multi-MPS platforms is embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects as discussed above.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments. Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The acts performed as part of the method may be ordered in any suitable way. Accordingly, embodiments may be constructed in which acts are performed in an order different than illustrated, which may include performing some acts simultaneously, even though shown as sequential acts in illustrative embodiments.

III. Fabrication of Apparatus

The apparatus described above may be fabricated through molding, machining, and sterilization processes. A monolithic surface micromachined fluidic plate is preferred. It provides reliable performance and it is easy to clean. All fluid contacting surfaces are accessible for cleaning. All components have relatively long life time, and no delamination occurs in sterilization processes such as autoclave. Pneumatics can be easily cleared of condensation. Generally, the apparatus uses only two plate components bonded together, such that all pneumatic channels occupy the same plane within the plate. Inlets may be stacked by interleaving their channels and using drilled features to connect the inlets at different vertical positions to the channel layer, thus packing them more densely on the side face of the manifold.

The turnaround cycle for modularized computer-aided design (CAD) and machining is relatively quick. It is easy and rapidly customizable according to researcher's individual needs.

A. Materials

The organs-on-a-chip systems may be fabricated from polydimethylsiloxane (PDMS), polysulfone, and other materials. PDMS is a versatile elastomer that is easy to mold (and thus highly amenable for prototyping), has good optical properties, and is oxygen permeable. In some embodiments, hydrophobic compounds including steroid hormones and many drugs exhibit strong partitioning into PDMS, thus precluding quantitative analysis and control of drug exposures (Toepke M W, et al., *Lab Chip* 6, 1484-1486 (2006)).

In preferred embodiments, the fluidic plate is fabricated from polysulfone (PSF). PSF is a rigid, amber colored, machinable thermoplastic with food grade FDA approval (21CFR177.1655) and USP Class VI biocompatibility. It is generally resistant to a wide range of chemical solvents, can be autoclaved, and is commonly used for instrumentation and medical devices. PSF also has dramatically lower surface adsorption and almost no bulk absorption of hydrophobic and lipophilic compounds (Ng S F, et al., *Pharmaceutics* 2, 209-223 (2010)).

All fluidic surfaces of the disclosed apparatus may be passivated prior to each experiment using serum albumin to further reduce the binding of biological molecules or drugs in the platform. The fluidic plate can also be cleaned and reused as many times as needed.

The top fluidic plate may be machined from a monolithic block of selected material, e.g., polysulfone (PSF) plastic, to include compartments to accommodate each MPS and an interconnecting chamber (called mixer or mixing chamber) to integrate and mix return flows, representing systemic circulation. Microfluidic channels and pumps are machined into the underside of the fluidic plate to convey fluid from the mixing chamber to each MPS. The individually addressable micro-pumps are fabricated in-line with the built-in fluid channels, and may be based on a 3-chamber, peristaltic pump-pump-pump design or a valve-pump-valve design. Additional pumps under each well provide recirculation flow, reducing nutrient and oxygen gradients within each compartment.

B. Techniques for Assembly and Bonding

The fluidic plate, pneumatic plate, and membrane (in sterilization bags) are generally assembled in a biosafety cabinet. Before assembly, a sterile microplate lid is generally taped onto the fluidic plate to protect the sterility of the cell culture region. The layers can then be assembled upside down to aid with visual alignment through the acrylic plate. Once the alignment pins mate with the fluidic plate, the platform can be carefully removed from the hood, keeping pressure to maintain the seal between the plates. Screws can be inserted and tightened in a nonsterile environment as long as the plates are not separated. Two fully assembled platforms can be daisy chained by connecting them with short lengths of tubing connecting straight across to the corresponding ports. Daisy chained platforms are most easily transported with a large metal tray.

Platforms are assembled at a few days (e.g., 4 days) prior to the start of cell-culture experiment of interest. Surface passivation (priming) of sterile platforms can be conducted with 1% BSA and penicillin-streptomycin in PBS in volumes appropriate to each compartment. Pump function and tubing connections can generally be visually confirmed by pumping from the mixer to each dry compartment, then by running the recirculation pumps backwards to clear all air from the channels. Spillways can be manually wetted with small volumes to ensure spillway operation. Platforms are usually run overnight in the incubator to passivate and confirm full operation before the addition of cells.

In some embodiments, fluidic plates are bonded to create closed fluidic paths using a sintering method between plastic plates of specific pointedness.

Figure 42:
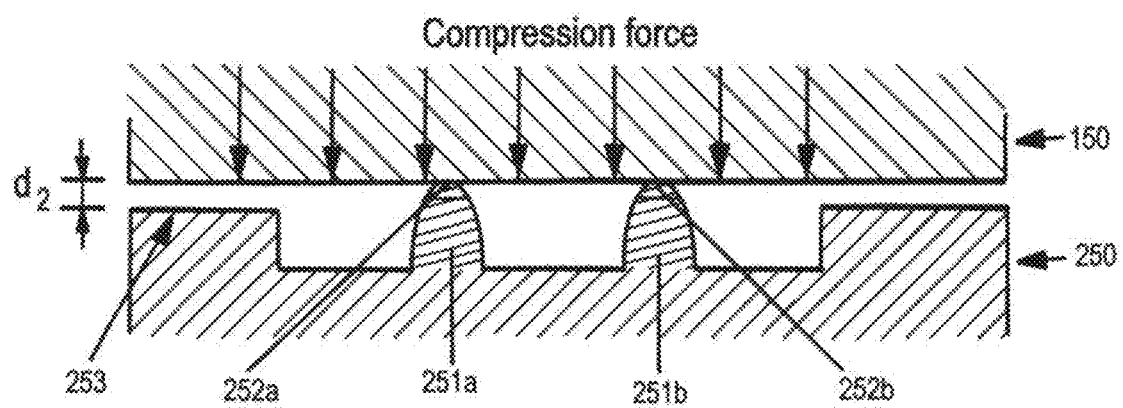
FIG. 42 is a cross-sectional side view schematic of a top plate 150 and a bottom plate 250, with geometries supporting sintering between the two plates. The bottom plate 250 has protruding pillars 251a and 251b with narrowed vertices 252a and 252b, respectively, and flat surfaced protrusion 253 lower than the protruding pillars by a height of $d_2$.
Figure 43:
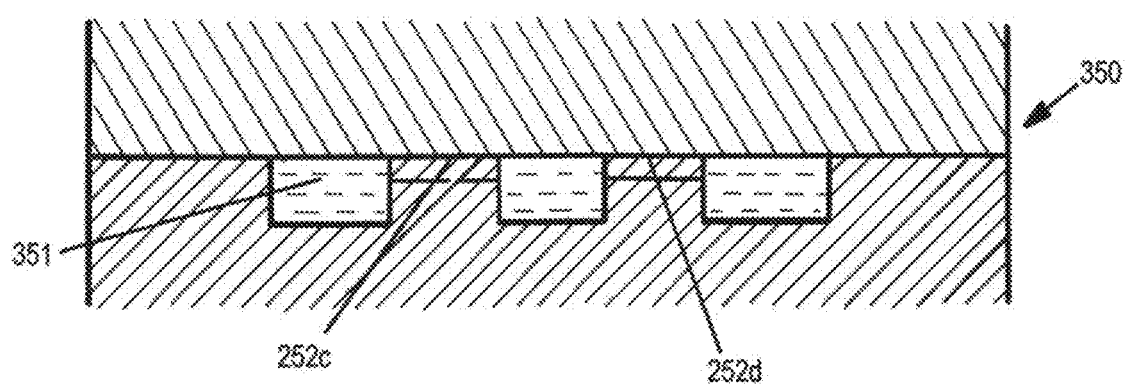
FIG. 43 is a cross-sectional side view schematic of a fused, one-piece construct 350, sintered from the top plate 150 and bottom plate 250 of FIG. 42. The vertices of protruding pillars in FIG. 42, after sintering (forced compression between the top plate and the bottom plate under heat), have deformed into sintered surfaces 252c and 252d and attached with the top plate. Space between protrusions of a bottom plate before sintering has become space (e.g., channel) for fluid 351.

FIGS. 42 and 43 illustrate a sintering method to bond multiple components, where a bottom plate 250 has one or more small (e.g., pointed) contact areas 251*a*/251*b* with a top plate 150 and some flat surface areas 253 that are shorter in height by a difference of $d_2$ than the vertices of the small contact areas 251*a*/251*b*. Following force and treatments to sinter the top plate with the bottom plate, previously small surface areas are deformed and fused with the flat bottom surface of the top plate, to a height set by the joint height of the contacted flat surfaces 253, resulting in a fused component 350 having internal space/volume 351 for passage of fluid.

In some embodiments, polyurethane (PU) membranes between about 20 and 200 microns thick, preferably between 50 and 100 microns thick, such as 50 microns thick, may be stretched on tension rings to maintain a constant tension. They can be laser cut with the corresponding pattern of screw holes on the pneumatic plate, if screw holes are present to align the top plate with the pneumatic plate.

A membrane diaphragm (optionally containing elastomer in regions corresponding to the pump and valve of the pneumatics) can be stretched between the pneumatics plate and the plate for the fluidic culture, and pressed to adhere to the pneumatic plate. In some embodiments, automation is used to attach the membrane to the fluidic plate.

Alternatively, elastomer patches may be used on the membrane layer to create seals and hermetic pathways in fluidic plates. Elastomer material may be used only at regions of a membrane or a patch corresponding to pneumatic pump and valves. Membranes containing elastomer patches can be prepared ahead of time and kept sterile for assembly of the chip. This would facilitate the assembly and operation of organonchip plates where an elastomer is deflected to create a pumping action only in very localized regions of the plate. A wide range of elastomer types and thicknesses may be applicable.

C. Surface Treatment to Control Wettability

Surface patterning may be used to control wettability of open fluidic passages in the organ-on-chip plates. Machining patterns include zebra (linear), shark, concentric, and smooth surfaces.

The use of different machining processes and micro texturization can dramatically affect wettability of culture plates for organs-on-chips. Surface finish may significantly modify polysulfone wettability up to about a 40° change in the contact angle with water or a cell-culture media. Incubator conditions may also increases wettability to a slight extent of about 2-3° difference. It may be preferable for mesofluidic devices to have an increased wettability in order to improve the performance.

In general, dark polysulfone is more hydrophobic than light polysulfone. Selection of different grades of polysulfone provides another means to vary the wettability of the plates.

D. Sterilization

One or more sterilization procedures may be performed on the cell-culturing fluidic plate, the actuation membrane, and optionally the pneumatic plate. Sterilization techniques include gas treatment (e.g., ethylene oxide), ionizing radiation, sonication, surface treatment (e.g., surfactant), and autoclave.

Generally before use, the top plate (e.g., polysulfone top plate) is cleaned and sterilized. First, the plate can be submerged in about 10% bleach for about 30 to 60 minutes, followed by a short rinse in distilled water. A residue-free surfactant was then used to remove any remaining contaminants by sonicating, submerged in about 10% solution (e.g., 7× solution, MP Biomedicals #MP0976680HP) for about 15 minutes. Two subsequent 15-minute sonication cycles in fresh deionized water follow to remove all surfactant before a final deionized water rinse. The plate can then be air dried, sealed in a sterilization bag, and autoclaved.

Generally, the pneumatic plate does not require formal sterilization, but prior to assembly it may be wiped thoroughly with a kimwipe sprayed with 70% ethanol to remove any dust or particles from the sealing areas that contact the membrane.

Pneumatic actuator membranes may be rinsed in about 10% 7× solution and with excess deionized water. Generally, an ethylene oxide gas sterilization step follows after the membranes are air dried, and the membrane is allowed 24 hours to degas in a chemical fume hood.

E. Cells

Differentiated cell types and specialized cell types such as stem cells and paneth cells, as well as microbiome for some embodiments such as gut MPS, may be added to the platform.

The microphysiological systems (MPSs) supported by the platform may comprise primary cells, cell lines, pluripotent stem cells, progenitor cells, organoids, or any combination of mammalian or non-mammalian cells. For example, epithelial monolayers formed on transwell inserts from Caco2 cells or Caco-2 cells mixed with HT29 cells is one model of the gut, where circulation in the basal compartment (beneath the transwell) serves to improve the mixing and thus transport of drugs and other agents from the apical side of the epithelial layer to the basal side of the epithelial layer; the mixing facilitates the rapid distribution of drugs and other compounds in the basal compartment, and thus improves overall mixing between different MPS units on the platform. This model can be made more sophisticated by adding a source of immune cells (e.g. dendritic cells or macrophages from human peripheral blood monocytes or other sources) to the basal side of the membrane. It can be made even more sophisticated by culturing the epithelium on top of stroma encapsulated in an extracellular matrix gel; a similar arrangement can be used with primary intestinal cells. A second type of flow module is exemplified by the Liverchip-type arrangement, where flow is pumped through a scaffold containing 3D tissues comprising multiple cell types on a scaffold designed to distribute flow through the tissue. In another configuration, a closed microfluidic device with flow channels on either side of a central gel region may support tissues like 3D islets or lymph nodes, where endothelial cells seeded into the gel with the islets or lymph nodes form 3D vessels that allow perfusion of the islets or lymph nodes through the channels. Islets or lymph nodes may also be maintained in a gel in a transwell insert, and the basal side of the transwell insert can be covered with endothelial cells. Finally, cells may be added to the central circulation unit or any of the individual MPS circulation units to allow cell trafficking. For example, PBMC added to the basal compartment of the gut can traffic to the stroma across the membrane under inflammatory signals.

In some embodiments where triple negative breast cancer (TNBC) (i.e., lacking expression of estrogen, progesterone, and Her2 receptors) micrometastases in liver is modeled in the disclosed apparatus, MDA-MB-231 cells along with primary human hepatocytes and non-parenchymal cells may be cultured.

In some embodiments where gut and liver MPS are modeled to assess inflammatory-related stimulation of dormant micrometastases, absorptive enterocytes (e.g., CC2BB/e1 line) and mucin-secreting goblet cells (e.g., HT29-MTX line) may be seeded on the apical surface generally at a number ratio between 20:1 and 5:1, more preferably between 13:1 and 7:1, or about 9:1; whereas dendritic cells, obtained from in vitro differentiation of human PBMCs-derived monocytes, may be seeded on the lower side of the membrane of a TRANSWELL® in one well of the apparatus.

Other cell lines or cell types may be added dependent on use.

IV. Applications

In vitro to in vivo translation (IVIVT) is an interpretive step that compares and validates MPS results to clinically-relevant outcomes. The disclosed apparatus may be applied with the IVIVT method in assessing additional factors such as endogenous growth factor, inflammatory and hormone signals in the prediction of pharmacokinetics and pharmacodynamics (PK and PD). Compared with in vivo to in vitro correlation (IVIVC) and in vivo to in vitro extrapolation (IVIVE) methods in the prediction of PK, IVIVT goes a step further to include analysis of these additional factors and thus additionally predict PD, clinical toxicology, biomarkers, and patient stratification using information from MPS technologies. Combined with physiologically-based PK (PBPK) models for IVIVT, the disclosed apparatus provides an improved quantitative forecast on human responses to test agents, taking into accounts missing organs, organ and media size mismatches, and drug exposure.

In some embodiments, the system can also be used to exemplify diseases or disorders. For example, the apparatus may be used to establish micro-metastases in the context of a relatively large (≥1 million cells) mass of liver cells, and then to analyze complex cell-cell communication network signatures using both measurements that can be routinely made in patients (on the circulating medium) as well as measurements that cannot also be made on patients—the kinetics of tumor cell growth and death.

A. Preclinical Drug Discovery

MPS supports survival and functional culture of one or more organs on the chip for an extended period of time such as two, three, four, five weeks, two months, three months, or longer. Long-term multi-organ cultures are particularly advantageous for studying the pharmacology of low-clearance drugs, supporting repeated drug exposures, analyzing drug-drug interactions, and modeling chronic diseases.

The platform can be used for target identification and validation, target-based screening, phenotypic screening, and other biotechnological applications.

Cell and media volumes provide enough signal for commercial assays such as ELISAs and high-content, multi-plexed assays.

Multiple-omics measurements across the scales of information flow in cells, from DNA to RNA to protein, protein activity states, and metabolites, as well as similar types of analysis of patient-derived immune cell function.

Although standard culture systems are reasonably effective for most small molecule drug PK assays, a vast number of diseases lacking adequate therapies have inflammation implications and are not well represented or modeled in standard culture systems. The apparatus may be particularly suitable for later stages of drug development that generally involves the immune system. The apparatus has been shown to recapitulate a complex immunologically-based drug-drug interaction between the anti-IL6 receptor antibody, tocilizumab, and the metabolism of simvastatin—a phenomenon that could not be reproduced in standard cultures (Long T, et al., *Drug Metab Dispos* 44, 1940-1948 (2016)).

A wide range of drug agents (small molecules, peptide, proteins, nucleic acid, etc.) may be tested in the disclosed apparatus for medicinal, cosmetic, or scientific applications. Generally addition to the mixing well mimicks an intravenous dosage, and addition to the gut well mimicks an oral dosage.

Agents are selected based on the disease or disorder to be treated or prevented.

B. Disease and Disorder to be Modeled

The multi-organ apparatus is a useful tool for disease modeling and drug development, especially in identifying and defining the appropriate "minimal set" of interacting organ systems to represent a disease state.

Drug development for a variety of diseases and/or disorders may be improved utilizing the disclosed multi-organs on a chip apparatus by culturing relevant tissues or cell types for systemic studies. Complex individual organs-on-chips that capture the local features of disease, especially inflammation, are preferably applicable for modeling systemic diseases or diseases that are associated with multiple organs or involve multiple types of cells. The diseases and/or disorders that may be modeled in the disclosed bioreactor include but are not limited to cancers/tumors (e.g., tumors in the breast, bones, liver, lungs, and brain), chronic inflammatory diseases (e.g. diabetes, arthritis, endometriosis, and Alzheimer's), non-malignant growth of endometrium outside the uterus (endometriosis) or displaced into the uterine muscle (adenomyosis), abnormal liver functions such as those caused by non-alcoholic fatty liver disease, The system provides a means for exposing the cells to an agent to determine its effect on the cells administering the agent in different dosages, in a different dosing regimen, or in combination with one or more other agents and determining its effect on the cells, as well as wherein the agent is administered to different cell types or cell types associated with one or more diseases or disorders. This allows one to test agents in vitro with human cells under conditions mimicking a human, at least in part, under controlled conditions, looking for effects on other cell types, as well as on the cells one wants to monitor for an effect. This is more rapid, more controlled, and yet not restricted to a single class of cells or tissues.

EXAMPLES

The present invention will be further understood by reference to the following non-limiting examples.

Example 1. Perfused, Single-Organ Microphysiological Systems (MPSs) on the Chip

(1) Liver: Perfused, Coculture of Hepatocyte-Kupffer to Three Weeks

Materials and Methods

Metabolic and immunologically competent 3D cryopreserved human hepatocytes and kupffer cells were cocultured. Multiple hepatocyte and Kupffer cell donors have been qualified in the MPS. Co-cultures were responsive to Lipopolysaccharide (LPS) stimulus down to 0.01 µg/ml.

Results

Table 1 shows the comparison of hepatocytes only and coculture of hypatocyte and Kupffer cells at a 10:1 ratio over 7 days in a perfused MPS platform.

TABLE 1

Biological function of liver cells vs. immune-competent liver MPS.

| Function at Day 7 (n = 3) | Hepatocyte Only | Hepatocyte + Kupffer (10:1) |
|---|---|---|
| Albumin (µg/day/mg) | 35 ± 11 | 53 ± 32 |
| Urea (µg/day/mg) | 175 ± 75 | 184 ± 25 |
| CYP3A (pmol/min/mg) | 2.9 ± 0.5 | 2.0 ± 0.7 |

The secretions of interleukin 6 (IL-6) and tumor necrosis factor alpha (TNFα) of the cocultured liver MPS were measured. The reproducibility of IL-6 response to LPS stimulus was determined. A physiologically-relevant (relatively low) level of cortisol was used in the common media. Hydrocortisone (cortisol) enhanced differentiated function, but suppressed inflammatory response.

The duration of cryopreserved human hepatocytes and kupffer cell co-cultures on the perfused MPS platform was extended to 3 weeks.

Expression of 84 hepatic genes remained stable between day 7 and 21. Kupffer cells remained inactivated for 21 days, until stimulated with LPS. Cell death marker LDH declined after seeding and remained at a low constant level. Hepatic phenotypic activity, including albumin and CYP450 remained measurable and superior to 2D cultures for 21 days. CYP450 activity was sensitive to hydrocortisone levels in the cultures.

(2) Lung: Primary Human Tracheobronchial Epithelium Differentiation

Materials & Methods

A tracheobronchial module was developed in a TRANSWELL on the MPS platform. Primary basal epithelial cells (all CK5+) were differentiated at the air-liquid interface into a full subset of epithelial cell types. Different metrics were evaluated including transepithelial electrical resistance (TEER), mucus production, differentiated cell populations, and basal IL-8 production.

Results

Fluorescent microscopic images were taken and confirmed the expressions of differentiation and functional markers: Tubulin (ciliated), Ck5 (basal), Muc5Ac (goblet), and phalloidin (actin).

TABLE 2

Comparison of estimated and measured percentages of differentiated cells on the lung MPS platform.

| Cell Sub-type | Physiological Estimates | MIT - Donor Z Lung MPS |
|---|---|---|
| Basal | 20% | 28 ± 3% |
| Goblet | 1-5% | 1 ± 0.5% |
| Ciliated | 30-50% | 46 ± 11% |
| Clara | <1% | Not Determined |

Table 2 confirms the lung MPS model supported differentiation of cells, to a degree that aligned well with physiological estimates, which was indicative of its function of primary human tracheobronchial epithelial model.

(3) Endometrium: Half-Primary Coculture of Epithelium-Stroma is Stable and Functionally Secretes Glycoprotein Materials & Methods In a menstrual cycle, human endometrium undergoes a proliferative phase, marked by an increased level of estrogen, and a secretory phase, marked by an increased level of progesterone. In the secretory phase, endometrium secretes characteristic proteins such as glycodelin, prolactin, and insulin-like growth factor-binding protein 1 (IGF-BP1).

An exemplary endometrium model of cell culture system in a TRANSWELL® on the MPS platform includes hydrogel encapsulating stromal cells and epithelial cells on top surface of the hydrogel were cultured on the apical side of the TRANSWELL®. The epithelial cell source was primary human endometrial epithelial cells, which were readily obtained from endometrial biopsies, had limited expansion and lifespan in culture, exhibited functional differences between harvest in proliferative and secretory phase, and supported robust glycodelin secretion (secretory phase cells). The cell line used was Ishikawa human stage 1 adenocarincoma cell line, which were estrogen and progesterone receptor positive, polarized in matrigel (Chitcholtan et al., *Exp Cell Research*, (2013)) or functionalized PEG gels, and had low/variable secretion of glycodelin. The stromal cell source was primary human endometrial stromal cells, which were readily obtained from human biopsies, had well-established in vitro expansion protocols, and showed functional difference between harvest in proliferative and secretory phase. The cell line used was human tert-immortalized cell line (tHESC), which was highly proliferative and stable, had low/variable secretion of prolactin or IGF-BP1 without strong decidualization cues, and could be quiesced in PEG gels.

Results

With Ishikawa epithelial cells, the apical medium contained estradiol and progesterone. Ishikawa glycodelin secretion was below detection limit. Off-platform culture of tHESC had produced IGF-BP1 right at the detection limit and a borderline detectable amount of prolactin (PRL) from primaries (likely due to a dilution effect). On-platform co-culture of these "half-primary" cell lines were stable and had detectable functions from apical sampling.

(4) Gut/Immune: Coculture for Two Weeks Forming Intact Barrier, and Drug-Induced Leakiness Triggering Immune Response Materials & Methods Physiological gut system features absorption and metabolism, intestinal immune system, interactions between microbiome and mucosal interactions, immune interaction between cell and microbiome, and drug-immune interactions. An exemplary immune-competent gut model with cell culture in a TRANSWELL® on the MPS platform included enterocytes and goblet cells were cocultured on the apical side of the TRANSWELL and immune cells on basal side of the TRANSWELL membrane. The cell lines used were Caco2 (enterocytes), HT29-MTX (goblet cells), and dendritic cells (immune cells), where enterocytes: goblet cells were cultured at a 9:1 ratio (mimicking small intestine) to maturation off platform for 2 weeks and transferred to perfusion platform with added immune cells on the basal side of the TRANSWELL membrane.

Results

When cultured off-platform (static medium), immune cells at 14 days had much less survival than were cultured on-platform with basolateral flow, as confirmed via immunofluorescent microscopy. On-platform cultures at 14 days supported the function of gut barrier cells and their differentiation.

Example 2. Assessment of Drug Toxicity in Individual or 2-Way MPS on the Chip (1) Liver/Immune: Toxicities of Diclofenac and Tolcapone An immune-competent liver MPS model was prepared and studied. Diclofenac impaired liver functions while cell death was minimal. Tolcapone decreased mitochondrial activity and caused cell death.

(2) Gut/Immune: Toxicities of Diclofenac and Tolcapone

An immune-competent gut MPS model was prepared and studied. Diclofenac reduced epithelial barrier integrity, causing leaky gut with a minimal cell death. Tolcapone led to severe cellular death, hence a complete loss of epithelial function.

(3) Endometrium MPS: Toxicities of Diclofenac and Tolcapone

An endometrium MPS model was prepared and studied. Diclofenac-induced loss of function correlating with cellular death. Tolcapone induced loss of function correlating with cellular death.

(4) Gut-Liver 2-Way: Administration of Tolcapone to Gut ("Oral") Results in Gut-Specific Toxicity Materials & Methods An immune-competent gut-liver interacted MPS model was prepared (details similarly shown in Example 3) and studied. Tolcapone was added to the gut MPS to mimick "oral" administration. Metrics were an volume-weighted average from the 3 media compartments: $Signal_{systemic} = Signal_{apical, gut} * V_{apical, gut} + Signal_{basal, gut} * V_{basal, gut} + Signal_{liver} * V_{liver}$.

Results

In the presence of tolcapone, gut and liver suffered MPS-specific loss of function, which was indicative of MPS-specific toxicity of tolcapone even delivered "orally". Gut and liver also suffered from MPS-specific cell death markers whereas generic marker was insensitive to tolcapone, which indicated site of toxicity of tolcapone. Intestinal Fatty Acid Binding Protein (I-FABP) was used as a clinical biomarker of enterocyte damage for various disease states.

Example 3. Inflammatory Cytokine/Chemokine Crosstalk in Gut-Liver 2-Way MPS

Immune-competent human liver (hepatocytes and Kupffer cells) combined with intestinal (enterocyte, goblet cells, and dendritic cells) microphysiological systems is studied in this in vitro platform, to examine gut-liver interactions under normal and inflammatory contexts.

The liver is situated downstream from the gut; as such, it is constantly exposed to gut-derived factors, including metabolites, microbial antigens and inflammatory mediators. However, a quantitative understanding of how these multicellular tissues communicate and contribute to overall (patho)physiology is limited.

Background

Gut-liver crosstalk is an integral part of normal physiology and their dysregulation is a common denominator in many disease conditions (Marshall J C, *Host Defense Dysfunction in Trauma, Shock and Sepsis: Mechanisms and Therapeutic Approaches*, eds Faist E, Meakins J L, & Schildberg F W (Springer Berlin Heidelberg, Berlin, Heidelberg), 243-252 (1993)). Furthermore, gut and liver are major organs involved in drug absorption and metabolism; changes to their functional interaction can impact their response to therapeutic intervention (Morgan E T, *Drug Metab Dispos* 29(3):207-212 (2001); Deng X, et al., Pharmacological Reviews 61(3):262-282 (2009); Long T J, et al. *Drug Metabolism and Disposition* 44(12):1940-1948 (2016)). Gut and liver functions are intimately linked by virtue of their anatomical proximity. The liver receives 70% of its blood supply from the gut via portal circulation; as such, it is constantly exposed to gut-derived factors, including metabolites, microbial antigens and inflammatory mediators. The gut-liver axis contributes considerably to the overall immunological state of the body, with the gut being the largest immune organ and the liver harboring over 70% of the total macrophage population in the body. Interspecies differences often hinder the accurate prediction of human responses in animal models; the discrepancy is especially evident in processes involving the immune system (Mestas J, et al., *The Journal of Immunology* 172(5):2731-2738 (2004); Giese C et al., *Adv Drug Deliver Rev* 69:103-122 (2014)). For instance, few of the clinical trials for sepsis treatment have led to drug approval (Seok J, et al. *Proc Natl Acad Sci USA* 110(9):3507-3512 (2013). Fink M P Virulence 5(1):143-153 (2014)). In sepsis, gastrointestinal and hepatic injury have been associated with increased disease severity (Rowlands B J, et al., British Medical Bulletin 55(1):196-211 (1999); Nesseler N, et al., Crit Care 16(5):235 (2012)). Acute liver failure in the first 72 hours following onset of sepsis was highly correlated with poor prognosis in septic patients. However, the lack of specific and predictive biomarkers precludes early diagnosis and patient stratification for effective intervention (Pierrakos C et al., *Crit Care* 14(1):R15 (2010)). Though the gut-liver axis has been implicated in the escalation of a septic response, the mechanisms and molecular players involved are poorly defined. Therefore, a fundamental understanding of gut-liver crosstalk is critical not only to the prediction of drug disposition, efficacy and toxicity, but also the elucidation of (patho)physiological mechanisms.

Materials & Methods

In vivo, the liver receives a dual blood supply, from the hepatic artery and the portal vein (Liaskou E, et al., *Mediators Inflamm* 2012:949157 (2012); Brown R P, et al., Toxicol Ind Health 13(4):407-484 (1997)). Correspondingly, the flow from the mixer well was partitioned into the gut and liver compartments to be 75% and 25%, respectively, scaled proportional to physiological cardiac output and hepatic blood flow, as shown below in Table 3 and Table 4. Output from the gut module fed into the liver, representing portal circulation. A systemic recirculation flow rate of 15 mL/day was used to ensure efficient distribution of exogenous and endogenous factors.

TABLE 3

Exemplary controlled flow rates in gut-liver MPS.

| Compartments | | Flow rates (μL/s) |
| --- | --- | --- |
| Mixer | self-circ | 1.0 |
| | mixer-gut | 0.13 |
| | mixer-liver | 0.043 |
| Liver | self-circ | 1.0 |
| Gut | self-circ, basal | 0.25 |

TABLE 4

Exemplary controlled volume in gut-liver MPS.

| Compartments | | Volume (mL) |
| --- | --- | --- |
| Mixer | | 1.0 |
| Liver | | 1.6 |
| Gut | Apical | 0.5 |
| | Basal | 1.5 |

The liver and gut tissue constructs in this study were multicellular and (innate) immune-competent, designed to encompass multiple key functions, including metabolic, barrier and immune functions. The liver microtissue comprised a co-culture of human primary cryopreserved hepatocytes and Kupffer cells at physiological 10:1 ratio, maintained in a culture medium permissive for retention of inflammation responses, as previously described (Long T J, et al. *Drug Metabolism and Disposition* 44(12):1940-1948 (2016); Sarkar U, et al. *Drug Metabolism and Disposition* 43(7):1091-1099 (2015)). The gut tissue was engineered to mimic the small intestine, with the epithelial monolayer derived from 9:1 ratio of absorptive enterocytes (Caco2-BBE) and mucus-producing goblet cells (HT29-MTX), and the immune compartment containing primary monocyte-derived dendritic cells.

Human primary hepatocytes and Kupffer cells were purchased from Life Technologies (HMCPMS, HUKCCS). Scaffolds were washed 15 min in 70% EtOH, rinsed twice in PBS, incubated for 1 hour @RT in 30 ng/mL rat tail collagen in PBS, left to dry overnight at room temperature, and punched into platforms (filter under scaffold under retaining ring). At day(−3) to experiment start, 10:1 ratio of hepatocytes and Kupffer cells were thawed into warm Cryopreserved Hepatocyte Recovery Medium (CHRM, Invitrogen), spun at 100 g for 8 min, and seeded at $6*10^5$ and $6*10^4$ cells/well, respectively, in cold hepatocyte seeding medium (250 mL Advanced DMEM+9 mL Gibco Cocktail A+12.5 mL FBS). After one day, the media was changed to D(−2) medium (250 mL Advanced DMEM+10 mL Cocktail B). After two more days, the medium was changed to common medium for the duration of the interaction experiment.

The common medium used in this study consisted of 500 mL Williams E medium+20 mL Gibco Cocktail B+100 nM hydrocortisone+1% Penicillin-Streptomycin (P/S)).

Caco2 (clone: C2BBe1, ATCC, passage 48-58) and HT29-MTX (Sigma, passage 20-30) cell lines were used for the intestinal epithelial cultures. Both cell lines were passaged twice post thawing before their use for TRANSWELL seeding. Cell lines were maintained in DMEM (Gibco™ 11965-092) supplemented with 10% Fetal Bovine Serum (Atlanta Biologicals S11150, heat inactivated (HI) at 57° C. for 30 minutes), 1x GlutaMax (Gibco™ 35050-061), 1× Non-Essential Amino Acids (Gibco™ 15140-148), and 1% Penicillin-Streptomycin (Gibco™ 15140-148). Caco2 at ~70-80% confluence and HT29-MTX at ~80-90% confluence were harvested using 0.25% Trypsin-EDTA (Gibco™ 25200-056) and mechanically broken up into single cells for TRANSWELL seeding. In seeding the cells into TRANSWELL®, the apical and basal side of TRANSWELL membrane were coated with 50 μg/mL Collagen Type I (Corning 354236) overnight at 4° C. The inserts were washed with PBS−/− to remove unbound protein. 9:1 ratio of C2BBe1 to HT29-MTX was seeded onto 12-well 0.4 μm pore size TRANSWELL® inserts (Costar 3460) at a density of $10^5$ cells/cm$^2$. Seeding media contained 10% heat-inactivated FBS, 1× GlutaMax, 1% P/S in Advanced DMEM (Gibco™ 12491-015). The apical media was replaced 1 day post seeding to remove any unattached cells. The top and bottom compartments of the TRANSWELL plate are fed with 0.5 mL and 1.5 mL of seeding medium every 2-3 days. After 7 days, medium was switched to a serum-free gut medium by replacing FBS with Insulin (5 μg/ml)-Transferrin (5 μg/ml)-Sodium Selenite (5 ng/ml) (Roche 11074547001).

To evaluate long-term functional viability in the gut-liver interaction, corresponding single tissue controls on platform were assayed with identical media volumes, flow rates and flow partitioning. All conditions were tested in a defined, serum-free common media that supported maintenance of gut and liver functions. The liver cells (10:1 hepatocyte: Kupffer cell) were seeded on platform 3 days prior to the start of the interaction experiment to allow for tissue formation and recovery from seeding-related stress responses. The gut MPS was differentiated for 3 weeks off-platform prior to the start of the interaction experiment. During long-term operation, the common culture medium in the system was replaced every 3 days.

To evaluate the health of the liver, samples from all compartments were taken at every media change (every 72 hours) and assayed for albumin via ELISA (Bethyl Laboratories, E80-129).

Various Cytochrome P450 (CYP) enzyme activities were measured using a developed CYP cocktail assay (Pillai V C, et al., *J Pharm Biomed Anal* 74:126-132 (2013)). Briefly, a cocktail of CYP substrates was added to liver compartment for a one hour incubation, and the supernatant was collected for downstream processing. Substrate-specific metabolite production was analyzed using mass spec.

Monocyte-derived dendritic cells were used as the immune component of the gut MPS. Briefly, peripheral blood mononuclear cells (PBMCs) were processed from Leukopak (STEMCELL Technologies, 70500) and stored in liquid nitrogen. For each experiment, PBMCs were thawed and monocytes were isolated using the EasySep Human Monocyte Enrichment Kit (STEMCELL Technologies, 19058). The monocytes were differentiated to dendritic cell in Advanced RPMI medium (Gibco™ 12633-012) supplemented with 1× GlutaMax, 1% P/S, 50 ng/mL GM-CSF (Biolegend 572903), 35 ng/mL IL4 (Biolegend 574004) and 10 nM Retinoic acid (Sigma R2625). After 7 days of differentiation (at day 19-20 of gut epithelial cell maturation), immature dendritic cells were harvested using Accutase (Gibco™ A11105-01) and seeded on to the basal side of the inverted gut TRANSWELLs® for 2 hours. After 2 hours, cells were returned to culture plate and fed with gut media.

One-day post dendritic cell seeding, gut barrier function was assessed. Gut MPS with transepithelial electrical resistance values of at least 250 Ohm*cm$^2$ were considered acceptable for experiment. For all interaction experiments on platform, the gut MPS was maintained in common media.

TEER measurement was performed using the EndOhm-12 chamber with an EVOM2 meter (World Precision Instruments). The samples and the EndOhm chamber were kept warm at ~37° C. on a hot plate. Temperature was rigorously maintained during TEER measurement to minimize variability.

Secreted mucin was measured in apical gut compartment using an Alcian Blue assay. The mucin quantification protocol was adapted from (5). Briefly, media from apical was collected in low-binding tubes, and spun down at 10,000 g for 5 minutes, and the supernatant was collected and stored at −80° C. for subsequent analysis. Mucin secretion was quantified against a standard of mucin (Sigma-Aldrich M3895) dissolved in culture medium. Samples and standards were incubated in a 96-well plate in a 3:1 mix of sample to Alcian Blue solution (Richard Allen Scientific) for two hours. After incubation, plates were centrifuged at 1640 g for 30 minutes at room temperature. Supernatant was removed by inverting the plates. Samples were rinsed twice with wash buffer (40% (v/v) of ethanol and 60% (v/v) of 0.1M sodium acetate buffer containing 25 mM $MgCl_2$ at pH 5.8), with a 10-minute centrifugation step after each rinse. After second spin, supernatant was removed and samples were dissolved with 10% SDS in distilled water. Plates typically required shaking or pipetting to fully resuspend samples. If bubbles formed during resuspension, plates were centrifuged again for about 5 minutes prior to absorbance measurement on a Spectramax m3/m2e at 620 nm.

Cytokine levels were measured using multiplex cytokine assays, 37-plex human inflammation and 40-plex panel chemokine panels (Bio-Rad Laboratories, Inc., Hercules, Calif., USA). Briefly, media samples were collected in low-binding tubes, spun down at 10,000 g for 5 mins to remove cell debris, and the supernatant was stored in −80° C. Samples were measured at multiple dilutions to ensure the measurements were within the linear dynamic range of the assay. To minimize non-specific binding to beads, bovine serum albumin (BSA) was added to achieve a final concentration of 5 mg/mL in all samples. The protein standard was reconstituted in the same media and the protein stock serially diluted to generate an 8-point standard curve. Assays were run on a Bio-Plex 3D Suspension Array System (Bio-Rad Laboratories, Inc.). Data were collected using the xPONENT for FLEXMAP 3D software, version 4.2 (Luminex Corporation, Austin, Tex., USA). The concentration of each analyte was determined from a standard curve, which was generated by fitting a 5-parameter logistic regression of mean fluorescence on known concentrations of each analyte (Bio-Plex Manager software).

To obtain the total production amount per platform, the concentration values were normalized by compartmental volume and added up across all compartments (mixer, gut, liver) in each platform.

For both the baseline and inflamed conditions (at Day 3, n=4), intestinal and hepatic tissues were taken out of the platforms, and mRNA was extracted using the PureLink RNA mini kit (ThermoFisher, 12183018A). Total RNA was analyzed and quantified using the Fragment Analyzer (Advanced Analytical), and cDNA was generated using the SMART-Seq v3 kit (Clontech). After cDNA fragmentation (Covaris S2), cDNA was end-repaired and adaptor-ligated using the SPRI-works Fragment Library System I (Beckman Coulter Genomics). Adaptor-ligated cDNA was then indexed during PCR amplification, and the resulting libraries were quantified using the Fragment Analyzer and qPCR before being sequenced on the Illumina HiSeq 2000. 40-50 nt single-end read with an average depth of 15-20 million or 5 million reads per sample were sequenced for the baseline and inflamed conditions respectively.

The FASTQ files were generated from the sequencing runs. The resultant reads were aligned to the human reference genome (GRch37/hg 19) using Tophat (version 2.0.12) (Kim D, et al. *Genome Biol* 14(4):R36 (2013)) to identify reads that map to known transcripts, accounting for splice junctions. HTSeq was used to determine the number of read counts uniquely overlap with known genomic features (Anders S, et al., *Bioinformatics* 31(2):166-169 (2015)).

To identify significantly altered genes in isolation vs interaction conditions, differential gene analysis of count data was performed using DESeq2 (Version 1.12.3) in R (Love M I, et al., *Genome Biol* 15(12):550 (2014)). Only genes with greater than 1 cpm (count per million) in at least 4 replicates, were included in the analysis. Multiple testing correction was performed using the procedure of Benjamini and Hochberg. Genes with an adjusted P-value below a FDR cutoff of 0.05 were considered significant.

GOSeq R packages (Young M D, et al., *Genome Biol* 11(2):R14 (2010)) was used to determine the over-represented biological of the differentially expressed genes (FDR-adjusted P-values<0.05).

GSEA (version 2.2.3) was performed to identify differentially regulated gene sets in isolation versus interaction, as describe in (Subramanian A, et al. (2005) *Proceedings of the National Academy of Sciences* 102(43):15545-15550). To stabilize variance, the normalized count data were processed using a regularized logarithm transformation in DESeq2. The signal-to-noise metric was used to generate the ranked list of genes. Canonical pathway gene sets from Molecular Signatures Database (c2.cp.v5.2) were used, which is a collection of curated genes sets from multiple databases (e.g., Reactome, KEGG, BioCarta, PID). The empirical P-values for each enrichment score were calculated relative to the null distribution of enrichment scores, which was computed via 1000 gene set permutations. Gene sets with nominal P-value <0.01 and q-value <0.05 were considered significant. Enrichment map (11), a Cytoscape plugin, was used to visualize the overlaps between significant gene sets and to facilitate the systematic interpretation of the interdependencies among different biological processes.

Results

1. Baseline Liver- and Gut-Specific Functions were Maintained for a Relatively Long Term (>2 Weeks) in Gut-Liver Interactome.

Hepatic and intestinal functions assessed over two weeks of culture were comparable for MPS maintained in communication or in isolation, as assessed by measurements of albumin production, gut barrier integrity, and gut mucus production. To evaluate liver metabolic function at the end of the 2-week experiment, the liver tissues from isolation and interaction conditions (in the absence of gut) were dosed with a cocktail of drug substrates targeting specific CYP450 enzymes. Drug-specific metabolite production in the media was measured using mass spectrometry to determine the cytochrome P450 activity of the different isoforms. Overall, the liver metabolic function was largely maintained, with modulation of select cytochrome P450 activities observed in gut-liver interaction. In particular, Cyp2C9 activity was significantly enhanced, while Cyp3A4/5 activity was depressed. Gut-specific functions, including barrier integrity and mucus production, were not sizably altered between interaction and isolation controls. Subtle but significant modulation of cytochrome P450 activities (e.g., CYP3A4 and CYP2C9) were observed after 2 weeks of interaction.

2. Bile Acid Synthesis Pathway was Modulated in Bi-Directional Gut-Live Crosstalk.

RNA sequencing was performed to profile the global transcriptomic changes in the gut and liver tissues after 3 days of interaction, with corresponding isolation controls (i.e., gut-only and liver-only). 105 genes were significantly (FDR-adjusted P<0.05) altered in the liver during interaction relative to isolation controls, of which 70 were upregulated and 35 were downregulated. For the gut, 6 genes were significantly differentially expressed, of which 2 were upregulated and 4 were downregulated. To understand the functional implications of these molecular changes, Gene Ontology (GO) analysis was performed to identify overrepresented biological processes that were altered under interaction. Only significantly altered genes (FDR-adjusted P<0.05) were used for GO analysis. The up-regulated biological processes in the liver primarily involved cell division-related processes (Table 5).

TABLE 5

Biological processes up-regulated in liver under gut-liver interaction.

| GO ID | Biological Processes | P-value | Adj. P-value |
|---|---|---|---|
| GO:0051302 | regulation of cell division | 0.0E+00 | 0.0E+00 |
| GO:0000070 | mitotic sister chromatid segregation | 0.0E+00 | 0.0E+00 |
| GO:0007059 | chromosome segregation | 0.0E+00 | 0.0E+00 |
| GO:0007049 | cell cycle | 9.6E−18 | 1.1E−14 |
| GO:0006996 | organelle organization | 7.3E−10 | 3.6E−07 |
| GO:0008283 | cell proliferation | 3.4E−09 | 1.4E−06 |
| GO:0007017 | microtubule-based process | 4.9E−08 | 1.4E−05 |

Induction of cell cycle genes in liver may indicate an adaptive response to gut-derived signals, although the soluble factors involved are unknown. On the other hand, the down-regulated biological processes in the liver were mainly metabolic processes including bile acid biosynthesis, lipid metabolism and xenobiotic metabolism (Table 6).

TABLE 6

Biological processes down-regulated in liver under baseline gut-liver interaction.

| GO ID | Biological Processes | P-value | Adj. P-value |
|---|---|---|---|
| G0:0006694 | steroid biosynthetic process | 2.2E−05 | 1.5E−01 |
| GO:0006579 | amino-acid betaine catabolic process | 2.8E−05 | 1.5E−01 |
| GO:0008202 | steroid metabolic process | 4.7E−05 | 1.5E−01 |
| GO:1901617 | organic hydroxy compound biosynthetic process | 1.0E−04 | 2.6E−01 |
| G0:0044283 | small molecule biosynthetic process | 1.8E−04 | 3.8E−01 |
| GO:0015914 | phospholipid transport | 2.2E−04 | 3.9E−01 |
| GO:0044281 | small molecule metabolic process | 3.3E−04 | 4.8E−01 |

Specifically, a mediator of the bile acid metabolism, CYP7A1, was down-regulated, which was indicative of a physiological coupling of gut-liver functions, e.g., bile acide-mediated enterohepatic crosstalk. CYP7A1 is an enzyme central to bile acid synthesis; and its feedback inhibition via FGF19 enterohepatic communication is well established (Ding L, et al., *Acta Pharm Sin B* 5(2):135-144 (2015)). The result on CYP7A1 was consistent with previous findings that perfusion of precision-cut rat intestinal and hepatic tissues in a microfluidic device for 7 hours resulted in bile acid-mediated CYP7A1 inhibition (van Midwoud P M, et al., *Lab Chip* 10(20):2778-2786 (2010)). Though the number of significant genes in the gut samples was insufficient for GO analysis, PCSK9, one of the differentially expressed genes, was found to play a key role in cholesterol and lipid homeostasis. In fact, cholesterol and various types of bile acids have been shown to suppresses PCSK9 mRNA expression in Caco2 intestinal cultures (Leblond F, et al. *Am J Physiol Gastrointest Liver Physiol* 296(4):G805-815 (2009)). The studies showed the convergence on cholesterol and bile acid metabolism pathways was indicative of transcriptional rewiring due to inter-MPS communication.

3. Coordinated Transcriptomic Changes and Tissue-Specific Transcriptomic Changes were Observed in Inflammatory Gut-Liver Crosstalk.

A large number of immune cells reside in the gut and liver during homeostasis and their activation in disease can contribute to systemic pathophysiology. Liver dysfunction associated with idiosyncratic adverse drug reactions has been linked to inappropriate immune activation (Cosgrove B D, et al. *Toxicology and Applied Pharmacology* 237(3):317-330 (2009)). This study complemented parenchymal tissue models with immune cells in both the gut and liver to provide a more physiologically-relevant culture platform for disease modeling and drug testing. Reciprocal immune-epithelial cell communication drives systemic inflammation.

In an inflammatory context mimicking endotoxemia, 2 ng/mL lipopolysaccharide (LPS) was added in the circulating media from day 0 (Gut MPS on platform) to day 3 (RNAseq was performed) while the operation of the system and the isolation controls were tested in a similar way to the baseline studies above. The LPS concentration was chosen based on clinically-relevant range of plasma endotoxin (2-10 ng/mL) reported in patients with inflammatory diseases (Guo S, et al, *Am J Pathol* 182(2):375-387 (2013)).

RNA sequencing was performed to assess the global molecular changes associated with inflammatory gut-liver crosstalk. For the liver, 2548 genes were significantly altered in the interaction, of which 1137 genes were upregulated and 1411 genes were downregulated. GO analysis of the differentially expressed genes showed upregulation of cytokine response and antigen processing and presentation pathways, and downregulation of lipid and xenobiotic metabolism pathways (Table 7).

TABLE 7

Biological processes up-regulated in liver under inflammatory gut-liver interaction.

| GO ID | Biological Processes | P-value | Adj. P-value |
|---|---|---|---|
| GO:0006955 | immune response | 1.7E−28 | 2.3E−24 |
| GO:0006952 | defense response | 1.5E−27 | 1.0E−23 |
| GO:0019221 | cytokine-mediated signaling pathway | 2.5E−25 | 4.6E−22 |
| GO:0060337 | type I interferon signaling pathway | 2.0E−25 | 4.4E−22 |
| GO:0051707 | response to other organism | 8.8E−22 | 7.6E−19 |
| GO:0019882 | antigen processing and presentation | 3.1E−06 | 2.9E−04 |
| GO:0002250 | adaptive immune response | 1.0E−07 | 1.2E−05 |
| . . . see further list in Table 11 and below. | | | |

TABLE 8

Biological processes down-regulated in liver under inflammatory gut-liver interaction:

| GO ID | Biological Processes | P-value | Adj. P-value |
|---|---|---|---|
| GO:0044281 | small molecule metabolic process | 7.8E−97 | 1.0E−92 |
| GO:0006082 | organic acid metabolic process | 5.4E−78 | 1.8E−74 |
| GO:0055114 | oxidation-reduction process | 5.4E−69 | 1.4E−65 |
| GO:0044710 | single-organism metabolic process | 2.3E−56 | 5.0E−53 |
| GO:0032787 | monocarboxylic acid metabolic process | 4.0E−54 | 7.4E−51 |
| GO:0006629 | lipid metabolic process | 7.4E−53 | 9.7E−50 |
| GO:0006805 | xenobiotic metabolic process | 1.3E−23 | 5.7E−21 |
| . . . see further list in Table 12 and below. | | | |

For the gut, 780 genes were significantly altered during interaction, of which 290 genes were upregulated and 490 genes were downregulated. Similarly, GO analysis revealed upregulation of defense response, antigen processing and presentation pathways and protein translation; down-regulated pathways included alcohol biosynthesis, steroid and lipid metabolism (Table 9).

TABLE 9

Biological processes up-regulated in gut under inflammatory gut-liver interaction.

| GO ID | Biological Processes | P-value | Adj. P-value |
|---|---|---|---|
| GO:0006952 | defense response | 4.5E−20 | 5.3E−16 |
| GO:0060337 | type I interferon signaling pathway | 1.2E−19 | 5.3E−16 |
| GO:0002376 | immune system process | 1.4E−13 | 2.2E−10 |
| GO:0034097 | response to cytokine | 9.2E−13 | 1.1E−09 |
| GO:0006082 | organic acid metabolic process | 9.8E−10 | 3.5E−07 |
| GO:0019882 | antigen processing and presentation | 6.0E−07 | 1.4E−04 |
| GO:0006418 | tRNA aminoacylation for protein translation | 6.6E−10 | 2.7E−07 |
| . . . see further list in Table 11 and below. | | | |

TABLE 10

Biological processes down-regulated in gut under inflammatory gut-liver interaction.

| GO ID | Biological Processes | P-value | Adj. P-value |
|---|---|---|---|
| GO:0046165 | alcohol biosynthetic process | $5.5 \times 10^{-16}$ | $7.0 \times 10^{-12}$ |
| GO:0008202 | steroid metabolic process | $2.6 \times 10^{-14}$ | $1.0 \times 10^{-10}$ |
| GO:1901615 | organic hydroxy compound metabolic process | $3.2 \times 10^{-14}$ | $1.0 \times 10^{-10}$ |
| GO:0044281 | small molecule metabolic process | $4.4 \times 10^{-12}$ | $4.3 \times 10^{-09}$ |
| GO:0032787 | monocarboxylic acid metabolic process | $4.8 \times 10^{-11}$ | $3.8 \times 10^{-08}$ |
| GO:0006629 | lipid metabolic process | $7.8 \times 10^{-11}$ | $5.9 \times 10^{-08}$ |
| GO:0055114 | oxidation-reduction process | $5.0 \times 10^{-08}$ | $2.4 \times 10^{-05}$ |
| . . . see further list in Table 12 and below. | | | |

In addition to gene-based GO analysis that focused only on the significantly altered genes determined by an arbitrary statistical cut-off, Gene Set Enrichment Analysis (GSEA) was also performed to uncover coordinated changes in groups of genes that are functionally related. GSEA can reveal more nuanced pathway regulation that might have been masked by strict cut-offs in gene-based approach. Generally, GSEA results were largely consistent with GO analysis outcomes, but with greater interpretability and generality. Consensus clusters of gene sets from different databases were obtained, which contained overlapping but distinct groups of genes that define major biological processes. Specifically, inflammation-related pathways centered around IFNα/β/γ signaling were up-regulated whereas metabolic processes involving cholesterol and lipid metabolism were down-regulated in both the gut and liver in interaction (Table 11). The pronounced alteration in inflammatory processes and lipid metabolism was characteristic of a sepsis response.

TABLE 11

Gene sets commonly up-regulated in both gut and liver in the gut-liver MPS

| Pathways | | Liver: q-val | Gut: q-val |
|---|---|---|---|
| IFN signaling | Reactome_Interferon_alpha_beta_signaling | 0.0 + 00 | 0.0 + 00 |
| | Reactome_Interferon_gamma_signaling | 0.0 + 00 | 0.0 + 00 |
| | Reactome_Interferon_signaling | 0.0 + 00 | 0.0 + 00 |
| Cytokine | Reactome_cytokine_signaling_in_immune_system | 0.0 + 00 | $3.0 \times 10^{-03}$ |
| Antigen processing | Kegg_antigen_processing_and_presentation | $1.0 \times 10^{-03}$ | $1.0 \times 10^{-03}$ |
| | Reactome_antigen_presentation_folding_assembly_and_peptide_loading_of_class_I_MHC | $2.0 \times 10^{-03}$ | $30 \times 10^{-03}$ |
| | Reactome_antigen_processing_cross_presentation | $6.0 \times 10^{-03}$ | $2.5 \times 10^{-02}$ |
| | Reactome_ER_phagosome_pathway | $7.0 \times 10^{-03}$ | $4.0 \times 10^{-03}$ |
| Immune processes | Kegg_intestinal_immune_network_for_IGA_production | $1.8 \times 10^{-02}$ | $2.5 \times 10^{-02}$ |
| | Reactome_immunoregulatory_interactions_between_a_lymphoid_and_a_non_lymphoid_cell | $4.0 \times 10^{-03}$ | $2.4 \times 10^{-02}$ |
| | Kegg_allograft_rejection | $1.0 \times 10^{-03}$ | 0.0 + 00 |
| | Kegg_autoimmune_thyroid_disease | $2.0 \times 10^{-03}$ | 0.0 + 00 |
| | Kegg_viral_myocarditis | $2.0 \times 10^{-03}$ | $4.0 \times 10^{-03}$ |
| | Kegg_graft_versus_host_disease | $3.0 \times 10^{-03}$ | 0.0 + 00 |
| | Kegg_Type_I_diabetes_mellitus | $7.0 \times 10^{-03}$ | 0.0 + 00 |

TABLE 12

Gene sets commonly down-regulated in both gut and liver in the gut-liver MPS.

| Pathways | | Liver: q-val | Gut: q-val |
|---|---|---|---|
| Endogeneous and xenobiotic metabolism | Reactome_cytochrome_p450_arranged_by_substrate_type | 0.0 + 00 | $3.3 \times 10^{-02}$ |
| | Reactome_phase_I_functionalization_of_compounds | 0.0 + 00 | $4.4 \times 10^{-02}$ |
| | Kegg_metabolism_of_xenobiotics_by_cytochrome_p450 | 0.0 + 00 | $4.6 \times 10^{-02}$ |
| Lipid metabolism | Kegg_PPAR_signaling_pathway | 0.0 + 00 | $4.0 \times 10^{-03}$ |
| | Reactome_lipid_digestion_mobilization_and_transport | $4.0 \times 10^{-03}$ | $3.9 \times 10^{-02}$ |
| | Reactome_lipoprotein_metabolism | $1.0 \times 10^{-02}$ | $4.3 \times 10^{-02}$ |
| | Reactome_metabolism_of_lipids_and_lipoproteins | $1.0 \times 10^{-03}$ | $8.0 \times 10^{-03}$ |
| Steroid and bile acid metabolism | Kegg_steroid_hormone_biosynthesis | $1.1 \times 10^{-02}$ | 0.0 + 00 |
| | Reactome_bile_acid_and_bile_salt_metabolism | 0.0 + 00 | $3.2 \times 10^{-02}$ |

In addition to the co-modulated pathways, tissue-specific regulation was also identified. Pathways involved in hypoxia and TGFβ/SMAD signaling were exclusively upregulated in the liver in interaction, suggestive of a pro-fibrotic response. Although the current study focused on acute inflammation, chronic liver inflammation has been linked to liver fibrosis.

In the gut, PI3K-mediated ERBB2 and ERBB4 signaling was upregulated, which was indicative of a wound healing or anti-apoptotic response, possibly serving as a protective mechanism. Previously, ERBB2 (Yamaoka T, et al. *Proc Natl Acad Sci USA* 105(33):11772-11777 (2008); Zhang Y, et al., *Lab Invest* 92(3):437-450 (2012)) and ERBB4 (Frey M R, et al., *Gastroenterology* 136(1):217-226 (2009)) signaling have been shown, in vitro and in vivo, to protect against TNF-induced apoptosis in intestinal epithelial cells and provide pro-survival and pro-healing effects following intestinal injury.

Complete lists of gene sets involved in tissue-specific modulation are shown below:

Gene sets up-regulated uniquely in liver during inflammatory gut-liver crosstalk included Biocarta_TNFR2_pathway, St_tumor_necrosis_factor_pathway, PID_TNF_pathway, Reactome_chemokine_receptors_bind_chemokines, Kegg_cytokine_cytokine_receptor_interaction, Kegg_rig_i_like_receptor_signaling_pathway, Kegg_cytosolic_dna_sensing_pathway, Reactome_negative_regulators_of_rig_i_MDA5_signaling, Naba_secreted_factors, PID_CD40_pathway, PID_hif1_tfpathway, PID_hif2pathway, PID_il23_pathway, Kegg_primary_immunodeficiency, Reactome_antiviral_mechanism_by_ifn_stimulated_genes, Reactome_)O.o_linked_glycosylation_of_mucins, Reactome_regulation_of_hypoxia_inducible_factor_hif_by_oxygen, Reactome_rig_i_mda5_mediated_induction_of_ifn_alpha_beta_pathways, Reactome_signaling_by_tgf_beta_receptor_complex, Reactome_smad2_smad3_smad4_heterotrimer_regulates_transcription, Reactome_traf6_mediated_irf7_activation, Reactome_transcriptional_activity_of_smad2_smad3_smad4_heterotrimer, and St_fas_signaling_pathway.

Gene sets up-regulated uniquely in gut during inflammatory gut-liver crosstalk included PID_IL12_2pathway, Kegg_abc_transporters, Reactome_amino_acid_synthesis_and_interconversion_transamination, Kegg_aminoacyl_trna_biosynthesis, Reactome_cytosolic_trna_aminoacylation, Reactome_trna_aminoacylation, Kegg_cell_adhesion_molecules_cams, Kegg_histidine_metabolism, Reactome_activation_of_genes_by_atf4, Reactome_perk_regulated_gene_expression, Reactome_PI3K_events_in_erbb2_signaling, and Reactome_PI3K_events_in_erbb4_signaling.

Gene sets down-regulated uniquely in liver during inflammatory gut-liver crosstalk included Biocarta_ami_pathway, Biocarta_intrinsic_pathway, Kegg_alanine_aspartate_and_glutamate_metabolism, Kegg_arachidonic_acid_metabolism, Kegg_arginine_and_proline_metabolism, Kegg_beta_alanine_metabolism, Kegg_biosynthesis_of_unsaturated_fatty_acids, Kegg_butanoate_metabolism, Kegg_citrate_cycle_tca_cycle, Kegg_complement_and_coagulation_cascades, Kegg_drug_metabolism_cytochrome_p450, Kegg_drug_metabolism_other_enzymes, Kegg_fatty_acid_metabolism, Kegg_glycine_serine_and_threonine_metabolism, Kegg_glycolysis_gluconeogenesis, Kegg_ropanoate_metabolism, Keggglyoxylate_and_dicarboxylate_metabolism, Kegg_histidine_metabolism, Kegg_linoleic_acid_metabolism, Kegg_lysine_degradation, Kegg_oxidative_phosphorylation, Kegg_parkinsons_disease, Kegg_peroxisome, Kegg_proximal_tubule_bicarbonate_reclamation, Kegg_pyruvate_metabolism, Kegg_retinol_metabolism, Kegg_tryptophan_metabolism, Kegg_tyrosine_metabolism, Kegg_valine_leucine_and_isoleucine_degradation, PID_hnf3b_pathway, Reactome_biological_oxidations, Reactome_branched_chain_amino_acid_catabolism, Reactome_citric_acid_cycle_tca_cycle, Reactome_fatty_acid_triacylglycerol_and_ketone_body_metabolism, Reactome_formation_of_fibrin_clot_clotting_cascade, Reactome_metabolism_of_amino_acids_and_derivatives, Reactome_peroxisomal_lipid_metabolism, Reactome_phase_ii_conjugation, Reactome_pyruvate_metabolism_and_citric_acid_tca_cycle, Reactome_respiratory_electron_transport, Reactome_respiratory_electron_transport_atp_synthesis_by_chemiosmotic_coupling_and_heat_production_by_uncoupling_proteins_, Reactome_synthesis_of_bile_acids_and_bile_salts, Reactome_synthesis_of_bile_acids_and_bile_salts_via_7alpha_hydroxychol esterol, and Reactome_tca_cycle_and_respiratory_electron_ transport.

Gene sets down-regulated uniquely in gut during inflammatory gut-liver crosstalk included Biocarta_TNFR2_pathway, Kegg_DNA_replication, Kegg_pantothenate_and_coa_biosynthesis, Kegg_pentose_and_glucuronate_interconversions, Kegg_steroid_biosynthesis, Kegg_terpenoid_backbone_biosynthesis, PID_aurora_b_pathway, PID_hif1_tfpathway, Reactome_activation_of_atr_in_response_to_replication_stress, Reactome_activation_of_the_pre_replicative_complex, Reactome_cholesterol_biosynthesis, Reactome_deposition_of_new_cenpa_containing_nucleosomes_at_the_centr omere, Reactome_DNA_strand_elongation, Reactome_e2f_mediated_regulation_of_dna_replication, Reactome_fatty_acyl_coa_biosynthesis, Reactome_formation_of_tubulin_folding_intermediates_by_cct_tric, Reactome_g1_s_specific_transcription, Reactome_g2_m_checkpoints, Reactome_transport_of_vitamins_nucleosides_and_related_molecules, and Reactome_triglyceride_biosynthesis.

4. Systemic Inflammation Suppressed Hepatic Detoxification Function.

Hepatic clearance of endogenous and xenobiotic compounds is mediated by two mechanisms, i.e., metabolism and bile elimination. The results revealed inflammatory crosstalk negatively affected both of these pathways and might lead to the buildup of toxic by-products. Collectively, CYP1A2, CYP2C9, CYP2C19, CYP2D6, an CYP3A4 and 3A5 are responsible for the metabolism of over 90% of known drugs (Jacob A, et al., Int J Clin Exp Med 2(3):203-211 (2009); Ebrahimkhani M R, et al., Adv Drug Deliv Rev 69-70:132-157 (2014)). All of these were suppressed in the liver in the integrated system, likely due to accumulation of inflammatory mediators, such as IL6, TNFα, and/or type I interferons (Long T J, et al. *Drug Metabolism and Disposition* 44(12):1940-1948 (2016); Huang S M, et al. *Clin Pharmacol Ther* 87(4):497-503 (2010)).

In short, lipid metabolism and inflammation were the dominant pathways altered during gut-liver interaction. Lipoprotein binding to LPS can redirect the LPS uptake from Kupffer cells to hepatocytes, thereby attenuating immune activation and facilitating bile clearance of LPS (Khovidhunkit W, et al., *J Lipid Res* 45(7):1169-1196 (2004)). Peroxisome proliferator-activated receptors (PPARs), master regulators of lipid metabolism, have been shown to exert anti-inflammatory effects (Varga T, et al., *Biochim Biophys Acta* 1812(8):1007-1022 (2011)). Taken together, the suppression of apolipoprotein synthesis and PPAR signaling observed during inflammatory gut-liver crosstalk indicates a potential loss of a protective mechanism, thereby intensifying inflammation in immune and epithelial cells. The complexities in systemic response to perturbations motivate the need for multi-cellular and multi-organ experimental models.

Sepsis patients are susceptible to adverse drug reactions due to inflammation-induced suppression of liver metabolic function, specifically the activity of cytochrome P450 enzyme system (Kim T H, et al., *Febs J* 278(13):2307-2317 (2011)). The results demonstrated altered mRNA expression of Phase I and Phase II metabolic enzyme in inflammatory gut-liver crosstalk. Thus, accurate prediction of drug pharmacokinetics and pharmacodynamics necessitates the consideration for multi-organ interaction as well as the physiological context (ie., health vs. disease). This is especially pertinent for drugs with a narrow therapeutic window because even modest changes to cytochrome P450 activities can precipitate toxicity.

5. Cytokine Levels in the Gut-Liver Integrated System Deviates from the Linear Sum of Individual, Isolated Systems.

The levels of secreted cytokines and chemokines were measured in the media at 6, 24, and 72 hours post stimulation to examine the temporal evolution of the inflammatory response. Pairwise hierarchical clustering was performed on the 72 hr cytokine measurement to explore the correlations of cytokine responses among the analytes and conditions. Unsupervised principal component analysis (PCA) revealed that the over 96% of the covariance in the cytokine dataset can be captured by the first 2 principal components. PC1 accounted for 76.5% of the variability in the data, segregating the interaction versus isolation controls; PC2 accounted for 19.8% of the total variability and discriminated the gut and liver only conditions. The loading plot depicted the relative contribution of each analyte to the $1^{st}$ and $2^{nd}$ principal components. All analytes were positively loaded on PC1 and contributed to the cytokine level in the integrated system, whereas loadings on PC2 can help infer the primary tissues of origin of the circulating cytokines/chemokines in the integrated system. While none of the soluble factors were unique to gut or liver, multivariate cytokine patterns can reveal tissue-specific signatures.

In order to accurately assess the contribution of inter-MPS crosstalk to the integrated inflammatory response, the measured cytokine levels in the interacting system were compared to the theoretical linear sum of the isolated conditions. The cytokine level observed in isolation accounted for cytokine output due to direct TLR4 activation and intra-MPS paracrine signaling. The actual (measured) cytokine levels in the integrated systems deviated significantly from the linear sum of the isolated systems, revealing non-linear modulation of cytokine production as a result of inter-MPS communication. Approximately 58% of the analytes were linearly additive, 23% were less than additive, and 19% were more than additive, some very markedly so. Interestingly, several cytokines exhibited similar temporal dynamics as CXCL6, which was linearly additive up to 24 hr, and then diverged from linear sum and became more than additive. This may suggest a threshold-dependent regulation, where cytokine production is dependent on the accumulation of upstream inducer molecules during organ crosstalk.

6. Inflammatory-Related CXCR3 Ligand was Greatly Amplified in Gut-Liver Interaction.

Table 12 showed a notable more than additive amplification of CXCR3 ligands, where CXCL10 (IP10) and CXCL11 (I-TAC) were most significantly more than additive and CXCL9 (MIG) was borderline significant. The fractions of total analytes that were additive, subadditive, and more than additive in terms of the level in the gut-liver MPS, compared to the linear sum of the levels in individual gut and individual liver, were 58%, 23%, and 19%, respectively. CXCR3 signaling has been implicated in autoimmunity, transplant rejection, infection, and cancer (Groom J R, et al., *Immunol Cell Biol* 89(2):207-215 (2011); Singh U P, et al., *Endocr Metab Immune Disord Drug Targets* 7(2):111-123 (2007)).

TABLE 12

Cytokines/chemokines statistically different from linear sum (Adj. P-value < 0.05) and the corresponding receptors.

| | Cytokines/chemokines | Receptors | Target cells |
|---|---|---|---|
| Sub-additive | CCL21 | CCR7, CCR11 | thymocytes & activated T cells |
| | CCL1 | CCR8, CCR11 | monocytes, NK cell, B cells & DCs |
| | CCL11 | CCR3 | leukocytes, eosinophils |
| | CXCL12 | CXCR4, CXCR7 | lymphocytes, endothelial progenitors |
| | CHI3L1 | — | — |
| | CCL22 | CCR4 | lymphocytes, monocytes, DCs, NK cells |
| | MIF | CXCR2, CXCR4 | most hematopoetic cells & endothelial cells |
| | IFN-γ | IFNγ-R | immune cells & epithelial cells |
| | CCL27 | CCR10 | memory T lymphocytes |
| | CXCL13 | CXCR5 | B lymphocytes |
| Synergistic | CXCL10 | CXCR3 | Th 1 cells, NK cells |
| | CXCL11 | CXCR3, CXCR7 | Th 1 cells, NK cells, monocytes, neutrophils |
| | CXCL6 | CXCR1, CXCR2 | neutrophils |
| | CCL20 | CCR6 | lumphocytes, DCs |
| | CCL2 | CCR2 | monocytes, basophils |
| | CX3CL1 | CX3CR1 | leukocytes |
| | CCL19 | CCR7 | lymphocytes, DCs, hematopoetic progenitors |
| | CXCL9 | CXCR3 | Th1 cells, NK cells |

These results showed that consideration of gut-liver crosstalk may be important for assessing systemic inflammatory processes and their potential influence on disease development.

RNA sequencing data showed activation of IFNα/β/γ signaling pathways in both the gut and liver during organ crosstalk. TNFα can magnify IFN-dependent production of CXCR3 ligands. PCA loadings revealed that TNFα was predominately gut-derived and IFNγ was produced at comparable levels by both the gut and the liver. It was plausible that gut (dendritic cells)-derived TNFα interacted with tissue-specific IFNγ signaling to drive CXCR3 ligand production in both the gut and liver. However, the relative contribution of epithelial and immune compartment to the integrated response was difficult to ascertain. Although immune cells are the principal responders to endotoxin due to higher expression of TLR4 as shown in Table epithelial cells also contribute to inflammation indirectly via activation by immune cell-derived cytokines, such as TNFα and IL-1 (Nguyen T V, et al. *Drug Metab Dispos* 43(5):774-785 (2015); Yeruva S, et al., *Int J Colorectal Dis* 23(3):305-317 (2008); Dwinell M B, et al., *Gastroenterology* 120(1):49-59 (2001)).

TABLE 14

TLR expression (Log10, normalized to GAPDH)

| Cell types | TLR1 | TLR2 | TLR3 | TLR4 | TLR5 |
|---|---|---|---|---|---|
| Primary human hepatocytes (thawed) | 179.6 | 48.0 | 332.0 | 12.0 | 13.7 |
| Primary human hepatocyte after 4 days in culture | 299.2 | 104.2 | 314.4 | 50.4 | 13.2 |
| Primary Kupffer cells (thawed) | 3496.4 | 10713.5 | 83.7 | 2753.7 | 24.5 |

Exposure of rat hepatocytes to TNFα and IFNγ in vitro promoted CXCL10 mRNA and protein expression (Hassanshahi G, et al., *Iran J Allergy Asthma Immunol* 6(3):115-121 (2007)). Combinations of IL-1α/β, TNFα and IFNγ have been shown to induce CXCR3 ligand gene expression and protein secretion in intestinal cell lines and human intestinal xenografts. To assess the epithelial contribution to the cytokine response, 5 ng/mL TNFα, 5 ng/mL IFNγ, or both, was added for presence of 24 hours to stimulate the gut epithelium (Caco2-BBE/HT29-MTX) basally. Co-treatment of TNFα and IFNγ on the gut epithelium, in the absence of immune cells, resulted in marked amplification of 4 out of the 8 chemokines identified in the integrated system, including CXCL9, CXCL10, CXCL11 and CX3CL1 (Table 11).

These results corroborated with the RNAseq findings and demonstrated that IFNγ and TNFα signaling crosstalk was central to the chemokine production in the integrated system. These results showed epithelial cells are not passive bystanders during inflammatory gut-liver crosstalk, but contribute considerably to the overall immune milieu via paracrine interactions with immune cells.

Under inflammatory gut-liver interaction, more than additive amplification of chemokine production was detected from the disclosed integrated gut-liver MPS. This amplification was in part mediated by TNFα and IFNγ signaling. Although immune cells were normally considered as the primary sensor of endotoxin, the results here showed epithelial cells responded to immune cells-derived signals to influence CXCL9/10/11 and CX3CL1 chemokine production. Exposure to TNFα and IFNγ did not result in the amplification of CCL19, CCL20, CXCL6 and CCL2 in intestinal epithelial cells, which indicated the involvement of additional mechanisms, likely in different cell types.

The chemokine production observed in the integrated system can target cells of the innate and adaptive immune system (Table 12). Potential immune cell recruitment can be inferred based on the chemokines and the corresponding receptors profile. Although adaptive immunity was not represented in the system, regulation of pathways linking innate and adaptive immunity were evident during organ crosstalk. For example, enrichment of the CD40 costimulatory process was identified. CD40 is a surface receptor ubiquitously expressed on immune cells as well as non-immune cells. CD40L is predominantly expressed by CD4+ T cells and CD40-CD40L engagement mediates heterologous cellular communication (Danese S, et al., Gut, 53(7):1035-1043 (2004)). Taken together, CXCR3 chemokine production and CD40-CD40L regulation implicates a bias toward Th1 signaling.

Example 4. 4-Way MPS on the Chip for Pharmacokinetic/Pharmacodynamic (PK-PD) Prediction (1) 4-Way MPS Survival and Functional for at Least 2 Week Materials & Methods Validation: Flow rates in thirteen 4-MPS platforms (n=9 pumps per platform) averaged from 0.82 to 1.12 µL/s without calibration, and had an average standard deviation of 0.07 µL/s. Software calibration factors were calculated from the flow rate measurement and entered to correct the pump rates to within ±5% of the target flow rates.

A systemic interaction flow rate of $Q_{mix}$=5 mL/day was used for the duration of the experiment. Flow was partitioned to each MPS from the mixer based on the relative percentages of cardiac output to each tissue type in humans; these numbers can be easily modified on the platform for different scaling strategies and MPS modules. Additionally, intra-MPS basal recirculation rates of 0.25 µL/s (gut, lung, and endometrium MPSs) and 1 µL/s (liver MPS and mixer) were used to provide well-mixed basal media in each compartment and oxygenate the liver tissue. Complete media changes were conducted every 48 hours. During media changes, samples were taken from each compartment to assess MPS function throughout the two-week interaction study. Biomarker metrics of healthy cell function were measured during a 2-week co-culture of 4-way MPS: liver, gut, lung, and endometrium, with a partitioning of flow. Every two days, secreted albumin and IGFBP-1 were measured from conditioned media. Barrier integrity of the Gut and Lung MPSs was quantified with trans-epithelial electrical resistance (TEER), measured off-platform using the commercial EndOhm systems. Simultaneously, functionality of each MPS in isolation was monitored.

Results 1. 4-Way MPS Supports Cell Viability and Functions for at Least Two Weeks.

Continuous functionality metrics from 4-MPS platform studies indicated the multi-organ MPS viability during the 2-week culture. Transient albumin secretion kinetics was observed of an initial increase in albumin secretion followed by a gradual decline by the conclusion of the experiment. Barrier integrity of the Gut and Lung MPSs was quantified with trans-epithelial electrical resistance (TEER). TEER values from the Gut MPS fluctuated in the early days of interaction studies before settling into a 150-250 Ω·cm² range for the remainder of the experiment. Lung MPS TEER values followed a similar trend of high TEER during the first few days, but eventually established stable values in the 600-800 Ω·cm² range. Endometrium MPS functionality, evaluated by secretion of insulin-like growth factor-binding protein 1 (IGFBP-1), remained in the 20-30 pg/day range throughout the study. Similar trends for each phenotypic metric in the isolation studies were observed, but IGFBP-1 secretion rate in the isolated endometrium MPS (off-platform) was lower than that of interaction studies.

2. Endogenously Produced Albumin from One Organ was Uniformly Distributed to Each Compartment with the Controlled Systemic Flow Rate.

In the 4-MPS platform, the effect of systemic flowrate ($Q_{mix}$) on albumin (endogenously produced by liver MPS) secretion and distribution kinetics was characterized via collecting samples from each compartment and, then, the results were computationally model to assess the accuracy of the distribution. The albumin concentrations in each compartment and the mixing chamber were at day 2 ($Q_{mix}$=5 ml/day), day 4 ($Q_{mix}$=15 ml/day), and day 6 ($Q_{mix}$=30 ml/day).

With an increasing systemic flow rate, albumin was distributed more uniformly as demonstrated by experimental measurements, where the deviation between MPSs was considerably lower with higher flow rates. Similarly, the calculated albumin secretion rates show smaller standard deviations. However, one platform showed considerably lower albumin in all compartments for days 2-4. Furthermore, computationally generated albumin distribution profiles was compared with experimentally measured albumin concentrations. The ratios of both values indicated that the higher flowrate resulted in more deterministic molecular biodistribution in the 4-way MPS platform.

(2) Gut-Liver/Lung/Endo 4-Way Platform: Independent Flow Rate Control Improves PK-PD Prediction for Complex Physiology Background In the study of modern medicine for human, interpretation of results from animal studies for the prospect of human treatment generally employs allometric scaling; and the interpretation of in vitro results for the prospect of in vivo efficacy is commonly referred to IVIV Correlation and Extrapolation. In vitro studies OF liver MPS pharmacokinetics (PK) is characterized by accounting for binding in media, drug uptake, and elimination. In vivo studies use known clinical data and physiological-based PK (PBPK)/absorption/binding models to calculate comparable parameters.

Clinical PK data of seven drugs from Manvelian et al. 2012, Shimamoto et al. 2000, Yilmaz et al. 2011, Willis et al. 1979 were compared with in vitro liver data gathered from LIVERCHIP™ to assess the prediction accuracy of in vitro results from LIVERCHIP™. While PBPK in vivo for free diclofenac elimination per cell has a rate constant of $1.76 \times 10^{-10}$ (cell*min)$^{-1}$, scaled liver MPS from LIVERCHIP™ was studied to show a diclofenac elimination rate constant of $5.66 \times 10^{-9}$ (cell*min)$^{-1}$. Hence, in vitro drug PK data from LIVERCHIP™ overestimated in vivo drug elimination rate.

Materials & Methods

Following a diagram and flow partitioning (total Qmixing=1 µL/s; liver/mixer recirculation=1 µL/s; gut/lung/endometrium recirculation rate=0.5 µL/s) (9 pumped flows: 5 self-circ, 4 mixing;
6 independent flow rates: 5 self-circ flows collapsed to 2 independent pneumatic duty cycles; 6 pump sets=18 DOF), 4-way MPS interactome was studied, where addition of agents to the mixing chamber accounted for an intravenous dosage while addition to the gut chamber accounted for an oral dosage. Drug was added to the apical side of gut chamber for the experiment.

Results

Uniform drug distribution was calculated as time for downstream (Endometrium) MPS to reach 90% of the concentration in mixing chamber. Drug exposure was calculated as area under curve (AUC) from 0-48 hr in downstream (Endometrium) MPS. Drug exposure and distribution were able to strongly drive selection of useful operational ranges: Qmixing>15 mL/day for drug permeability greater than $10^{-6}$ cm/s, and Qmixing>40 mL/day for AUC0-48 hr of greater than $2*10^4$ ng/L*hr.

Example 5. Operation of 7-Way MPS on the Chip

Materials & Methods

Validation: Flow rates in ten 7-way platforms (n=17 pumps per platform) averaged 1.12±0.10 µL/s. Software calibration factors were calculated from the flow rate measurement and entered to correct the pump rates to within ±5% of the target flow rates (0.99±0.056 µL/s).

A 7-way MPS platform was utilized and operated in a similar manner to the 4-MPS platform described in Example 4. The 7-way platform include gut (immune-competent), liver (immune-competent), lung, endometrium, cardiac, brain, and pancreas MPSs, and was assessed for survivability and function over a 3-week period. Each MPS was differentiated or matured in isolation prior to the interaction study. Platforms were run at a systemic flow rate of $Q_{mix}$=10 mL/day, with flow partitioning. During the medium changes, a basal common medium was used for the gut, lung, liver, and endometrium MPSs, while the new MPS were supplied with their preferred maintenance media. Each basal medium was then allowed to mix throughout the course of the interaction, with media changes at 48-hour intervals. Functionality of each MPS was evaluated every 2-4 days up to 3 weeks, in comparison to isolated MPSs to benchmark the non-interacting MPS functions. Due to the dramatic reduction in the functionality of isolated pancreas MPS, islets were replaced with the fresh islets at day 12 for both interaction and in-isolation studies.

Results 1. 7-Way MPS Supports Cell Viability and Functions for at Least Three Weeks.

Transient albumin secretion kinetics, sustained gut and lung TEER values, and IGFBP-1 secretion profiles were established. The functionality of cardiac MPS, which was monitored by beat frequency, was well maintained during the study. N-acetyl aspartate (NAA) and c-peptide release profiles revealed that both the brain MPS and the pancreas were also functional up to 3 weeks. The comparison of the interaction results with the isolation results showed no negative effect of interaction on the MPS functionality. Increased NAA secretion and more sustained c-peptide secretion were observed during the interaction. The long-term MPS viability and functionality could be maintained in the 7-MPS platform for at least extended culture periods of three weeks.

2. "Orally" Administered Drug and its Metabolite were Distributed Across MPSs in Concentrations Consistent with Model Pharmacokinetics Predictions.

Exogenous drug studies with clinically-relevant concentrations are important to translate in vitro results to clinical outcomes. Pharmacokinetics of diclofenac (DCF), a non-steroidal anti-inflammatory drug, was analyzed in the 7-MPS platform. The maximum measured plasma concentration, Cmax, of oral diclofenac in vivo varies between 2-6 µM (Davies N M, et al., *Clin. Pharmacokinet.* 33, 184-213 (1997)). 4'-hydroxy-DCF (4-OH-DCF) is the common metabolite of DCF.

To recapitulate clinically observed Cmax from oral delivery in the platform, diclofenac was added to the apical side of the gut MPS. The measured concentrations of DCF and 4'-hydroxy-DCF media across different MPS compartments fitted respective pharmacokinetic model predictions. The DCF dose was absorbed across the gut epithelial barrier, distributed to the liver MPS and subsequently to the mixing chamber and all the other MPS compartments. Metabolite 4-OH-DCF was produced in the liver MPS, circulated across the 7-way MPS platform, and was detected in all the others MPS compartments. Physiologically based pharmacokinetic (PBPK) model predictions on both DCF and 4-OH-DCF concentrations aligned well with the measured data, which indicated the platform functions in a deterministic manner consistent with biology predictions. The unbound intrinsic clearance (CL_int(u); i.e., the ability of liver to remove drug in the absence of flow) was estimated to be 13.90 µL/min, and approximately 19% of this clearance was estimated to be towards the formation of the 4-OH-DCF metabolite.

We claim:

1. A self-leveling spillway in a flat multi-well cell culture system of horizontally arranged wells, the spillways comprising
   a source well in the flat multi-well cell culture system, and
   a conduit with at least one horizontal portion and a geometry that causes capillary flow across the spillway for unidirectional fluid connectivity and self-level of fluid in the source well.

2. A fluidic multiwell device with an on-board pumping system comprising the self-leveling spillway of claim 1, the device further comprising:
   a) a first plate comprising:
      two or more wells comprising
         a three-dimensional space in each well defined by a bottom surface and a circumferential wall; and
         an inlet and an outlet in each well;
      a network of fluid paths providing fluid connectivity between at least two of the wells through the inlet and the outlet of each of the two wells;
   b) a detachable second plate comprising:
      a plurality of internal channels, each with an inlet opening and an outlet opening on opposing sides of the second plate, and
      one or more holes on the surface of the second plate in connection with each of the internal channels; and c) a barrier membrane positioned between the fluid paths of the first plate and the one or more holes on the surface of the second plate,
  wherein the barrier membrane is optionally bonded to the first plate,
  wherein the barrier membrane is at least partially flexible,
wherein applying a pressure to the internal channels of the second plate causes the membrane to move, thereby obstructing or clearing a portion of the fluid paths of the first plate.

3. The device of claim 2 further comprising a pneumatic manifold.

4. The device of claim 3 wherein the membrane is connected to the pneumatic manifold.

5. The spillway of claim 1 comprising a step entry geometry.

6. The spillway of claim 1 comprising a V-cut to minimize fluid film disruption.

7. The spillway of claim 1 comprising a radial meniscus pinning groove around the source well.

8. The spillway of claim 1 comprising a small-width and/or high aspect ratio groove at the bottom along the conduit effective to cause spontaneous capillary flow through the spillway.

9. The spillway of claim 8 wherein the conduit comprises an enlarged curved area to break fluid film into drops.

10. The spillway of claim 9 comprising a destination well, wherein the conduit comprises an inlet, an outlet, and a vertical groove along the wall and toward the bottom of the destination well, optionally comprising an undercut into a wall of the destination well positioned sufficiently from the outlet of the conduit to prevent back flow and syphoning.

11. The spillway of claim 9 comprising rings that prevent adhesion of fluid.

12. The spillway of claim 1 in a system comprising a fluidic multi-well device for culturing cells comprising an internal humidity sensor and/or a fluid moat to maintain humidity.

13. The spillway of claim 1 in a system comprising a fluidic multi-well device comprising fluidic pumping channels, a central modular pump, and manifold.

14. The system of claim 13 comprising a pump for pulsating flow.

15. The system of claim 13 comprising a pump for smooth flow in combination with parallel fluid channels.

16. The system of claim 13 comprising pumping means with a flow rate between zero and hundreds of milliliters per day, optionally with a controlled volume flux between 0.1 and 10 microliter/stroke, and frequencies between about 0.1 Hz and 20 Hz.

17. The system of claim 13 comprising an oxygen or fluid level sensor or optical means for determining fluid levels.

18. The system of claim 13 further comprising a fluid aggregation lid.

19. The system of claim 12 comprising a symmetrical front and back electrode capacitor for use as a monitor.

20. The system of claim 12 comprising a perfusion-enabled removable scaffold for a fluidic multi-well device.

21. A system comprising fluidic multi-well devices comprising the spillway of claim 1.

22. The system of claim 12 further comprising organ or tissue specific cells in the wells of the multi-well device.

23. The system of claim 22 wherein the cells are of a different origin in each of the wells of the multi-well device.

24. The system of claim 21 further comprising organ or tissue specific cells in the multi-well devices, wherein the cells are of a different origin in the same device.

25. The system of claim 24 wherein the cells are selected from the group consisting of liver cells, intestinal cells, pancreatic cells, muscle cells, bladder cells, kidney cells, pluripotent cells, and hematopoietic cells.

26. The spillway of claim 1, wherein the source well is horizontally arranged and the conduit connects the source well to a horizontally arranged destination well in the flat multi-well cell culture system.

27. The spillway of claim 1, wherein the conduit connects the source well to a destination well at below the top of the source well to below the top of the destination well.

28. The spillway of claim 1 comprising a groove at the bottom and along the conduit.

29. The spillway of claim 28, wherein the conduit comprises a round bottom, knife edge, or v-cut geometry.

30. The spillway of claim 28, the conduit has a height to width aspect ratio between about 1.5 and 5.

31. The spillway of claim 1, wherein the conduit has an exit geometry comprising a slope, an enlarged step, or an upward exit.

32. The spillway of claim 1, wherein the conduit has at least two horizontal portions.

33. A method of culturing cells comprising seeding the devices of any of claims 2, 3, 1, 12, 13, and 20 with cells.

34. The method of claim 33 further comprising exposing the cells to an agent to determine its effect on the cells.

35. The method of claim 34 further comprising administering the agent in different dosages, in a different dosing regimen, or in combination with one or more other agents and determining its effect on the cells.

36. The method of claim 35 wherein the agent is administered to different cell types or cell types associated with one or more diseases or disorders.

* * * * *

UNITED STATES PATENT AND TRADEMARK OFFICE
CERTIFICATE OF CORRECTION

| | |
|---|---|
| PATENT NO. | : 10,876,088 B2 |
| APPLICATION NO. | : 15/425858 |
| DATED | : December 29, 2020 |
| INVENTOR(S) | : Linda Griffith et al. |

It is certified that error appears in the above-identified patent and that said Letters Patent is hereby corrected as shown below:

On the Title Page

Item (72) replace "Mohan Brij Bhushan" with -- Brij Mohan Bhushan --

Signed and Sealed this
Fourth Day of April, 2023

Katherine Kelly Vidal
*Director of the United States Patent and Trademark Office*